(12) United States Patent
Oberboersch et al.

(10) Patent No.: US 7,968,591 B2
(45) Date of Patent: Jun. 28, 2011

(54) 1,3-DISUBSTITUTED 4-METHYL-1H-PYRROLE-2-CARBOXAMIDES AND THEIR USE IN MEDICAMENTS

(75) Inventors: Stefan Oberboersch, Aachen (DE); Bernd Sundermann, Aachen (DE); Corinna Sundermann, Aachen (DE); Edward Bijsterveld, CB Nijmegen (NL); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/331,011

(22) Filed: Dec. 9, 2008

(65) Prior Publication Data

US 2009/0137573 A1 May 28, 2009

Related U.S. Application Data

(63) Continuation of application No. PCT/EP2007/005098, filed on Jun. 8, 2007.

(30) Foreign Application Priority Data

Jun. 9, 2006 (DE) .......................... 10 2006 027 229

(51) Int. Cl.
*A61K 31/551* (2006.01)
*A61K 31/55* (2006.01)
*A61K 31/541* (2006.01)
*A61K 31/5377* (2006.01)
*A61K 31/4439* (2006.01)
*A61K 31/4545* (2006.01)
*A61K 31/454* (2006.01)
*A61K 31/433* (2006.01)
*A61K 31/4178* (2006.01)
*A61K 31/404* (2006.01)
*A61K 31/4025* (2006.01)
*A61K 31/40* (2006.01)
*C07D 417/12* (2006.01)
*C07D 413/04* (2006.01)
*C07D 405/04* (2006.01)
*C07D 407/04* (2006.01)
*C07D 401/14* (2006.01)
*C07D 401/12* (2006.01)
*C07D 401/06* (2006.01)
*C07D 403/12* (2006.01)
*C07D 207/34* (2006.01)

(52) U.S. Cl. ........ 514/423; 514/422; 514/361; 514/343; 514/414; 514/326; 514/254.01; 514/237.2; 514/399; 514/218; 514/316; 514/217.08; 514/227.8; 514/292; 548/127; 548/518; 548/527; 548/537; 548/530; 548/467; 548/314.7; 540/575; 540/602; 544/60; 544/141; 546/87; 546/187; 546/208; 546/279.1

(58) Field of Classification Search .................. 514/423, 514/422, 361, 343, 414, 326, 254.01, 237.2, 514/399, 218, 316, 217.08, 227.8, 292; 540/575, 602; 544/60, 141; 546/87, 187, 208, 279.1; 548/127, 518, 527, 537, 530, 467, 314.7
See application file for complete search history.

(56) References Cited

U.S. PATENT DOCUMENTS

| | | | | |
|---|---|---|---|---|
| 5,189,055 A | * | 2/1993 | Thal et al. ...................... | 514/422 |
| 5,698,581 A | * | 12/1997 | Kleemann et al. ............ | 514/447 |
| 7,250,443 B2 | * | 7/2007 | Desai et al. ................... | 514/422 |
| 2005/0014765 A1 | * | 1/2005 | Mailliet et al. ........... | 514/254.02 |
| 2007/0135494 A1 | | 6/2007 | Merla et al. | |

FOREIGN PATENT DOCUMENTS

| | | |
|---|---|---|
| EP | 0 957 099 A2 | 11/1999 |
| WO | WO 90/02733 A1 | 3/1990 |
| WO | WO 2004/018455 A1 | 3/2004 |
| WO | WO 2004/108685 A1 | 12/2004 |
| WO | WO 2005/113497 A1 | 12/2005 |

OTHER PUBLICATIONS

Alazard et al. Bulletin de la Societe Chimique de France, 1993, 130, 779-87.*
Registry Database for Registry No. 172458-72-9, entered STN on Jan. 19, 1996.*
Alazard, J.P., et al., "Composés interagissant avec la tubuline. Partie I: synthèse de phénylpyrroles *ortho-ortho'* substitués en rotation libre ou empêchée", Bull. Soc. Chim. Fr., 1993, vol. 130, No. 6, pp. 779-787. XP009090907.
German Search Report dated Dec. 19, 2006 including portions translated in English (Eight (8) pages).
International Search Report dated Oct. 22, 2007 including portion translated in English (Seven (7) pages).
PCT/ISA/237 including English translation (Nine (9) pages), Jan. 12, 2009.

* cited by examiner

*Primary Examiner* — Joseph R Kosack
*Assistant Examiner* — Matthew P Coughlin
(74) *Attorney, Agent, or Firm* — Crowell & Moring LLP

(57) ABSTRACT

1,3-disubstituted 4-methyl-1H-pyrrole-2-carboxamides corresponding to formula I

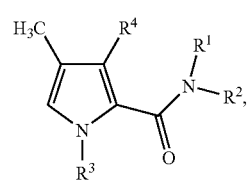

methods for their production, pharmaceutical compositions containing them, and the use thereof for noradrenalin receptor regulation, particularly for inhibiting noradrenalin reuptake, and/or for 5-HT receptor regulation, particularly for inhibiting 5-hydroxy tryptophan reuptake, and/or for opioid receptor regulation and/or for batrachotoxin (BTX) receptor regulation and/or for treating or inhibiting pain and other conditions.

19 Claims, No Drawings

1,3-DISUBSTITUTED 4-METHYL-1H-PYRROLE-2-CARBOXAMIDES AND THEIR USE IN MEDICAMENTS

CROSS REFERENCE TO RELATED APPLICATIONS

This application is a continuation of international patent application no. PCT/EP2007/005098, filed Jun. 8, 2007, designating the United States of America, and published in German on Dec. 13, 2007 as WO 2007/141039, the entire disclosure of which is incorporated herein by reference. Priority is claimed based on Federal Republic of Germany patent application no. DE 10 2006 027 229.3, filed Jun. 9, 2006.

BACKGROUND OF THE INVENTION

The present invention relates to 1,3-disubstituted 4-methyl-1H-pyrrole-2-carboxamides, a method for the manufacture thereof, medicaments containing these compounds and use thereof for the manufacture of medicaments.

Pain is a basic clinical symptom. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Conventional opioids, such as for example morphine, are effective in the treatment of severe to very severe pain, but they often lead to unwanted side effects, such as for example respiratory depression, vomiting, sedation, constipation or the development of tolerance. Moreover, they are frequently insufficiently effective in the case of neuropathic pain, suffered in particular by tumor patients.

SUMMARY OF THE INVENTION

It was one object of the present invention to provide new compounds which are suitable in particular as pharmaceutical active ingredients in medicaments.

Another object of the invention was to provide compounds useful in the treatment and/or inhibition of pain.

A particular object of the invention was to provide new compounds suitable for use in the treatment and/or inhibition of acute pain, chronic pain and/or neuropathic pain.

It has now surprisingly been found that disubstituted 4-methyl-1H-pyrrole-2-carboxamides corresponding to formula I set forth hereinafter are suitable for noradrenalin receptor regulation, in particular for inhibiting noradrenalin reuptake (noradrenalin uptake) and/or for 5-HT receptor regulation, in particular for inhibiting 5-hydroxy tryptophan reuptake (5-HT uptake) and/or for opioid receptor regulation and/or for batrachotoxin (BTX) receptor regulation and may therefore be used in particular as pharmaceutical active ingredients in medicaments for the treatment and/or inhibition of disorders or diseases associated with these receptors or processes.

The present invention accordingly provides 1,3-disubstituted 4-methyl-1H-pyrrole-2-carboxamides corresponding to formula I,

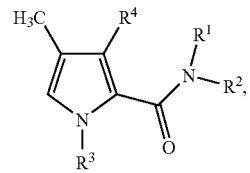

in which
$R^1$ denotes unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; phenyl, which is unsubstituted or substituted with 1, 2, 3, 4 or 5 substituents independently selected from the group consisting of F, Cl, Br, I, —CN, —CH$_2$—CN, —NO$_2$, —OH, —SH, —NH$_2$, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, —N(C$_{1-5}$-alkyl)$_2$, —C(=O)—H, —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, —S(=O)$_2$—NH$_2$, —S(=O)$_2$—NH—C$_{1-5}$-alkyl, —S(=O)$_2$—N(C$_{1-5}$-alkyl)$_2$, —S(=O)$_2$—NH-phenyl, [1,2,3]-thiadiazolyl, cyclopropyl, cyclobutyl, cyclopentyl, cyclohexyl, piperazinyl, pyrrolidinyl, piperidinyl, pyrazolyl, phenyl, furyl (furanyl), thiazolyl, thiadiazolyl, thiophenyl (thienyl), benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F; an unsubstituted or at least monosubstituted residue selected from the group consisting of naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl; unsubstituted or at least monosubstituted-(alkylene)-aryl, -(alkenylene)-aryl, -(alkynylene)-aryl, -(heteroalkylene)-aryl or -(heteroalkenylene)-aryl; unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl or —NH—C(=O)—$R^5$;

$R^2$ denotes H; unsubstituted or at least monosubstituted alkyl, alkenyl or alkynyl; unsubstituted or at least monosubstituted heteroalkyl, heteroalkenyl or heteroalkynyl; unsubstituted or at least monosubstituted aryl; or unsubstituted or at least monosubstituted-(alkylene)-aryl, -(alkenylene)-aryl, -(alkynylene)-aryl; or $R^1$ and $R^2$ together with the nitrogen atom to which they are bound denote heterocycloalkyl or heterocycloalkenyl, which is unsubstituted or substituted with at least one residue $R^6$;

$R^3$ denotes unsubstituted or at least monosubstituted alkyl, alkenyl or alkynyl; unsubstituted or at least monosubstituted heteroalkyl, heteroalkenyl or heteroalkynyl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^4$ denotes phenyl, which is in each case unsubstituted or substituted with 1, 2, 3, 4 or 5 substituents independently selected from the group consisting of F, Cl, Br, I, —CN, —$CH_2$—CN, —OH, —SH, —$NH_2$, —C(=O)—OH, —$C_{1-5}$-alkyl, —($CH_2$)—O—$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$-alkyl, —S(=O)—$C_{1-5}$-alkyl, —NH—$C_{1-5}$-alkyl, —N($C_{1-5}$-alkyl)$_2$, —C(=O)—O—$C_{1-5}$-alkyl, —C(=O)—H, —C(=O)—$C_{1-5}$-alkyl, —$CH_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—$NH_2$, —C(=O)—NH—$C_{1-5}$-alkyl, —C(=O)—N($C_{1-5}$-alkyl)$_2$, —S(=O)$_2$—$NH_2$, —S(=O)$_2$—NH—$C_{1-5}$-alkyl, —S(=O)$_2$—N($C_{1-5}$-alkyl)$_2$, —S(=O)$_2$—NH-phenyl, [1,2,3]-thiadiazolyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —$NO_2$, —OH, —SH, —$NH_2$, —C(=O)—OH, —$C_{1-5}$-alkyl, —($CH_2$)—O—$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$; or a residue selected from the group consisting of naphthyl, benzimidazolyl, triazinyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, isoindolyl, benzo[b]furanyl, benzo[b]thiophenyl, benzo[d]thiazolyl, benzodiazolyl, benzotriazolyl, benzoxazolyl, benzisoxazolyl, thiadiazolyl, oxadiazolyl, pyridazinyl, quinoxalinyl, quinazolinyl, quinolinyl, naphthridinyl and isoquinolinyl, which is in each case unsubstituted or optionally substituted with 1, 2, 3, 4 or 5 substituents independently selected from the group consisting of F, Cl, Br, I, —CN, —$CH_2$—CN, —$NO_2$, —OH, —SH, —$NH_2$, —C(=O)—OH, —$C_{1-5}$-alkyl, —($CH_2$)—O—$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$-alkyl, —S(=O)—$C_{1-5}$-alkyl, —NH—$C_{1-5}$-alkyl, —N($C_{1-5}$-alkyl)$_2$, —C(=O)—O—$C_{1-5}$-alkyl, —C(=O)—H, —C(=O)—$C_{1-5}$-alkyl, —$CH_2$—O—C(=O)-phenyl, —C≡C(=O)-phenyl, —NH—S(=O)$_2$—$C_{1-5}$-alkyl, —NH—C(=O)—$C_{1-5}$-alkyl, —C(=O)—$NH_2$, —C(=O)—NH—$C_{1-5}$-alkyl, —C(=O)—N($C_{1-5}$-alkyl)$_2$, —S(=O)$_2$—$NH_2$, —S(=O)$_2$—NH—$C_{1-5}$-alkyl, —S(=O)$_2$—N($C_{1-5}$-alkyl)$_2$, —S(=O)$_2$—NH-phenyl, [1,2,3]-thiadiazolyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —$NO_2$, —OH, —SH, —$NH_2$, —C(=O)—OH, —$C_{1-5}$-alkyl, —($CH_2$)—O—$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$;

$R^5$ denotes unsubstituted or at least monosubstituted alkyl, alkenyl or alkynyl; unsubstituted or at least monosubstituted heteroalkyl, heteroalkenyl or heteroalkynyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^6$ denotes —OH; F; Cl; Br; I; —SH; —$NO_2$; —$NH_2$; —NH—C(=O)—O—$R^7$; —C(=O)—O—$R^8$; —C(=O)—$R^9$; denotes unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl; and $R^7$, $R^8$ and $R^9$ each independently denote unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates. Preferably, $R^4$ may not denote a 1,4-dihydroxynaphthyl residue.

For the purposes of the present invention, the term "alkyl" covers acyclic saturated hydrocarbon residues, which may be branched or straight-chain and unsubstituted or at least monosubstituted with, as in the case of $C_{1-12}$ alkyl, 1 to 12 (i.e. 1, 2, 3, 4, 5, 6, 7, 8, 9, 10, 11 or 12) C atoms or with, as in the case of $C_{1-6}$ alkyl, 1 to 6 (i.e. 1, 2, 3, 4, 5 or 6) C atoms. If one or more of the substituents denote an alkyl residue or comprise an alkyl residue which is mono- or polysubstituted, this may preferably be optionally substituted with 1, 2, 3, 4 or 5, particularly preferably with 1, 2 or 3, substituents independently selected from the group consisting of F, Cl, Br, I, —$NO_2$, —CN, —OH, —SH, —$NH_2$, —N($C_{1-5}$-alkyl)$_2$, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —NH—C(=O)—O—$C_{1-5}$-alkyl, —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—O—$CH_2$-phenyl, —C(=O)—$NH_2$, —C(=O)—NH—$C_{1-5}$-alkyl, —C(=O)—N($C_{1-5}$-alkyl)$_2$, —C(=O)—NH-phenyl, —C(=O)—N($C_{1-5}$-alkyl)-phenyl, —C(=O)—NH-naphthyl, —C(=O)-pyrrolidinyl, —C(=O)-piperidinyl, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, wherein the above-stated $C_{1-5}$ alkyl residues may in each case be linear or branched and the above-stated phenyl or naphthyl residues may in each case be unsubstituted or substituted with 1, 2, 3, 4 or 5, preferably with 1, 2 or 3, substituents independently selected from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert.-butyl.

Particularly preferred substituents for alkyl may be independently selected from the group consisting of F, Cl, Br, I, —$NO_2$, —CN, —OH, —SH, —$NH_2$, —N($CH_3$)$_2$, —N($C_2H_5$)$_2$, —N($CH_3$)($C_2H_5$), —C(=O)—OH, —C(=O)—O—$CH_3$, —C(=O)—O—$C_2H_5$, —C(=O)—O—C($CH_3$)$_3$, —NH—C(=O)—O—C($CH_3$)$_3$, —N($CH_3$)-phenyl, —N—($C_2H_5$)-(p-toluoyl), —C(=O)—O—$CH_2$-phenyl, —C(=O)—NH-naphthyl, —C(=O)-pyrrolidinyl, —C(=O)—N($CH_3$)— phenyl and —C(=O)—NH—CH($CH_3$)$_2$.

Examples of suitable $C_{1-12}$ alkyl residues which may be unsubstituted or mono- or polysubstituted include methyl, ethyl, n-propyl, isopropyl, n-butyl, isobutyl, 2-butyl, tert.-butyl, n-pentyl, 2-pentyl, 3-pentyl, iso-pentyl, neopentyl, n-hexyl, 2-hexyl, 3-hexyl, n-heptyl, n-octyl, —C(H)($C_2H_5$)$_2$, —C(H)(n-$C_3H_7$)$_2$, (3,3)-dimethylbutyl, 4-methyl-2-pentyl and —$CH_2$—$CH_2$—C(H)($CH_3$)—($CH_2$)$_3$—$CH_3$. Examples of suitable $C_{1-6}$ alkyl residues which may be mentioned are methyl, ethyl, n-propyl, isopropyl, n-butyl, isobutyl, 2-butyl, tert.-butyl, n-pentyl, 2-pentyl, 3-pentyl, iso-pentyl, neopentyl, n-hexyl, 2-hexyl and 3-hexyl.

Polysubstituted alkyl residues are understood to be those alkyl residues which are polysubstituted, preferably di- or trisubstituted, either on different or on the same C atoms, for example trisubstituted on the same C atom as in the case of —$CF_3$, or at different locations as in the case of —(CHCl)—($CH_2F$). Polysubstitution may proceed with identical or different substituents. Examples of suitable substituted alkyl residues which may be mentioned are —$CF_3$, —$CF_2H$, —$CFH_2$, —$CH_2Cl$, —($CH_2$)—OH, —($CH_2$)—$NH_2$, —($CH_2$)—CN, —($CH_2$)—($CF_3$), —($CH_2$)—($CHF_2$), —($CH_2$)—($CH_2F$), —($CH_2$)—($CH_2Cl$), —($CH_2$)—($CH_2$)—OH, —($CH_2$)—($CH_2$)—$NH_2$, —($CH_2$)—($CH_2$)—CN, —($CF_2$)—($CF_3$), —($CH_2$)—($CH_2$)—($CF_3$), —($CH_2$)—($CH_2$)—($CH_2$)—OH, —($CH_2$)—N($CH_3$)$_2$, —($CH_2$)—($CH_2$)—($CH_2$)—Cl, —($CH_2$)—($CH_2$)—($CH_2$)—($CH_2$)—Cl, —($CH_2$)—C(=O)—OH, —($CH_2$)—($CH_2$)—C(=O)—OH, —($CH_2$)—C(=O)—O—$CH_3$ and —($CH_2$)—($CH_2$)—NH—C(=O)—O—C($CH_3$)$_3$.

For the purposes of the present invention, the term "alkenyl" covers acyclic unsaturated hydrocarbon residues, which may be branched or straight-chain and unsubstituted or at least monosubstituted and comprise at least one double bond, preferably 1, 2 or 3 double bonds, with, as in the case of $C_{2-12}$ alkenyl, 2 to 12 (i.e. 2, 3, 4, 5, 6, 7, 8, 9, 10, 11 or 12) C atoms or with, as in the case of $C_{2-6}$ alkenyl, 2 to 6 (i.e. 2, 3, 4, 5 or 6) C atoms. If one or more of the substituents denote an alkenyl residue or comprise an alkenyl residue which is mono- or polysubstituted, this may preferably be optionally substituted with 1, 2, 3, 4 or 5, particularly preferably with 1, 2 or 3, substituents independently selected from the group consisting of F, Cl, Br, I, —$NO_2$, —CN, —OH, —SH, —$NH_2$, —N($C_{1-5}$-alkyl)$_2$, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —NH—C(=O)—O—$C_{1-5}$-alkyl, —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—O—$CH_2$-phenyl, —C(=O)—$NH_2$, —C(=O)—NH—$C_{1-5}$-alkyl, —C(=O)—N($C_{1-5}$-alkyl)$_2$, —C(=O)—NH-phenyl, —C(=O)—N($C_{1-5}$-alkyl)-phenyl, —C(=O)—NH-naphthyl, —C(=O)-pyrrolidinyl, —C(=O)-piperidinyl, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated C$_{1-5}$ alkyl residues may in each case be linear or branched and the above-stated phenyl or naphthyl residues may in each case be unsubstituted or substituted with 1, 2, 3, 4 or 5, preferably with 1, 2 or 3, substituents independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert.-butyl.

Particularly preferred substituents for alkenyl may mutually independently be selected from the group consisting of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

Examples of suitable C$_{2-12}$ alkenyl residues include 1-propenyl, 2-propenyl, 1-butenyl, 2-butenyl, 3-butenyl, 1-pentenyl, 2-pentenyl, 3-pentenyl, 4-pentenyl, hexenyl, —CH=C(CH$_3$)$_2$, —CH=CH—CH=CH—CH$_3$ and —CH$_2$—CH$_2$—CH=CH$_2$.

Polysubstituted alkenyl residues are understood to be those alkenyl residues which are polysubstituted, preferably disubstituted, either on different or on the same C atoms, for example disubstituted on the same C atom as in the case of —CH=CCl$_2$, or at different locations as in the case of —CCl=CH—(CH$_2$)—NH$_2$. Polysubstitution may proceed with identical or different substituents. Examples of suitable substituted alkenyl residues which may be mentioned are —CH=CH—(CH$_2$)—OH, —CH=CH—(CH$_2$)—NH$_2$ and —CH=CH—CN.

For the purposes of the present invention, the term "alkynyl" covers acyclic unsaturated hydrocarbon residues, which may be branched or straight-chain and unsubstituted or at least monosubstituted and comprise at least one triple bond, preferably 1 or 2 triple bonds, with, as in the case of C$_{2-12}$ alkynyl, 2 to 12 (i.e. 2, 3, 4, 5, 6, 7, 8, 9, 10, 11 or 12) C atoms or with, as in the case of C$_{2-6}$ alkynyl, 2 to 6 (i.e. 2, 3, 4, 5 or 6) C atoms. If one or more of the substituents denote an alkynyl residue or comprise an alkynyl residue which is mono- or polysubstituted, this may preferably be optionally substituted with 1, 2, 3, 4 or 5, particularly preferably with optionally 1 or 2, substituents independently selected from the group consisting of F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —NH—C(=O)—C$_{1-5}$-alkyl, —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—O—CH$_2$-phenyl, —C(=O)—NH$_2$, —C(=O)—NH—C$_{1-5}$-alkyl, —C(=O)—N(C$_{1-5}$-alkyl)$_2$, —C(=O)—NH-phenyl, —C(=O)—N(C$_{1-5}$-alkyl)-phenyl, —C(=O)—NH-naphthyl, —C(=O)-pyrrolidinyl, —C(=O)-piperidinyl, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated C$_{1-5}$ alkyl residues may in each case be linear or branched and the above-stated phenyl or naphthyl residues may in each case be unsubstituted or substituted with 1, 2, 3, 4 or 5, preferably with 1, 2 or 3, substituents independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert.-butyl.

Particularly preferred substituents for alkynyl may be independently selected from the group consisting of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

Examples of suitable C$_{2-12}$ alkynyl residues include ethynyl, 1-propynyl, 2-propynyl, 1-butynyl, 2-butynyl, 3-butynyl, 1-pentynyl, 2-pentynyl, 3-pentynyl, 4-pentynyl and hexynyl.

Polysubstituted alkynyl residues should be taken to mean those alkynyl residues which are either polysubstituted on different C atoms, for example disubstituted on different C atoms as in the case of —CHCl—C—CCl. Examples of suitable substituted alkynyl residues which may be mentioned are —C≡C—F, —C≡C—Cl and —C≡C—I.

The term "heteroalkyl" denotes an alkyl residue as described above, in which one or more C atoms have in each case been replaced by a heteroatom independently selected from the group consisting of oxygen, sulfur and nitrogen (NH). Heteroalkyl residues may preferably comprise 1, 2 or 3 heteroatom(s) independently selected from the group consisting of oxygen, sulfur and nitrogen (NH) as chain link(s). Heteroalkyl residues may preferably be 2- to 12-membered, particularly preferably 2- to 6-membered.

Examples of suitable heteroalkyl residues, which may in each case be unsubstituted or mono- or polysubstituted, include —CH$_2$—O—CH$_3$, —CH$_2$—O—C$_2$H$_5$, —CH$_2$—O—CH(CH$_3$)$_2$, —CH$_2$—O—C(CH$_3$)$_3$, —CH$_2$—S—CH$_3$, —CH$_2$—S—C$_2$H$_5$, —CH$_2$—S—CH(CH$_3$)$_2$, —CH$_2$—S—C(CH$_3$)$_3$, —CH$_2$—NH—CH$_3$, —CH$_2$—NH—C$_2$H$_5$, —CH$_2$—NH—CH(CH$_3$)$_2$, —CH$_2$—NH—C(CH$_3$)$_3$, —CH$_2$—CH$_2$—O—CH$_3$, —CH$_2$—CH$_2$—O—C$_2$H$_5$, —CH$_2$—CH$_2$—O—CH(CH$_3$)$_2$, —CH$_2$—CH$_2$—O—C(CH$_3$)$_3$, —CH$_2$—CH$_2$—S—CH$_3$, —CH$_2$—CH$_2$—S—C$_2$H$_5$, —CH$_2$—CH$_2$—S—CH(CH$_3$)$_2$, —CH$_2$—CH$_2$—S—C(CH$_3$)$_3$, —CH$_2$—CH$_2$—NH—CH$_3$, —CH$_2$—CH$_2$—NH—C$_2$H$_5$, —CH$_2$—CH$_2$—NH—CH(CH$_3$)$_2$, —CH$_2$—CH$_2$—NH—C(CH$_3$)$_3$, —CH$_2$—S—CH$_2$—O—CH$_3$, —CH$_2$—O—CH$_2$—O—C$_2$H$_5$, —CH$_2$—O—CH$_2$—O—CH(CH$_3$)$_2$, —CH$_2$—S—CH$_2$—O—C(CH$_3$)$_3$, —CH$_2$—O—CH$_2$—S—CH$_3$, —CH$_2$—O—CH$_2$—S—C$_2$H$_5$, —CH$_2$—O—CH$_2$—S—CH(CH$_3$)$_2$, —CH$_2$—NH—CH$_2$—S—C(CH$_3$)$_3$, —CH$_2$—O—CH$_2$—NH—CH$_3$, —CH$_2$—O—CH$_2$—NH—C$_2$H$_5$, —CH$_2$—O—CH$_2$—NH—CH(CH$_3$)$_2$, —CH$_2$—S—CH$_2$—NH—C(CH$_3$)$_3$, —CH$_2$—CH$_2$—CH$_2$—O—CH$_3$, —CH$_2$—CH$_2$—CH$_2$—O—C$_2$H$_5$ and —CH$_2$—CH$_2$—C(H)(CH$_3$)—(CH$_2$)$_3$—CH$_3$.

Examples of suitable substituted heteroalkyl residues which may be mentioned are —(CH$_2$)—O—(CF$_3$), —(CH$_2$)—O—(CHF$_2$), —(CH$_2$)—O—(CH$_2$F), —(CH$_2$)—S—(CF$_3$), —(CH$_2$)—S—(CHF$_2$), —(CH$_2$)—S—(CH$_2$F), —(CH$_2$)—(CH$_2$)—O—(CF$_3$), —(CF$_2$)—O—(CF$_3$), —(CH$_2$)—(CH$_2$)—S—(CF$_3$) and —(CH$_2$)—(CH$_2$)—(CH$_2$)—O—(CF$_3$).

The term "heteroalkenyl" denotes an alkenyl residue as described above in which one or more C atoms have in each case been replaced by a heteroatom independently selected from the group consisting of oxygen, sulfur and nitrogen (NH). Heteroalkenyl residues may preferably comprise 1, 2 or 3 heteroatom(s) independently selected from the group consisting of oxygen, sulfur and nitrogen (NH) as chain link(s). Heteroalkenyl residues may preferably be 2- to 12-membered, particularly preferably 2- to 6-membered.

Examples of suitable heteroalkenyl residues which may be mentioned are —CH$_2$—O—CH=CH$_2$, —CH=CH—O—CH=CH—CH$_3$, —CH$_2$—CH$_2$—O—CH=CH$_2$, —CH$_2$—S—CH=CH$_2$, —CH=CH—S—CH=CH—CH$_3$, —CH$_2$—CH$_2$—S—CH=CH$_2$, —CH$_2$—NH—CH=CH$_2$, —CH=CH—NH—CH=CH—CH$_3$ and —CH$_2$—CH$_2$—NH—CH=CH$_2$.

Examples of suitable heteroalkenyl residues which may be mentioned are —CH$_2$—O—CH=CH—(CH$_2$)—OH, —CH$_2$—S—CH=CH—(CH$_2$)—NH$_2$ and —CH$_2$—NH—CH=CH—CN.

The term "heteroalkynyl" denotes an alkynyl residue as described above in which one or more C atoms have in each case been replaced by a heteroatom independently selected from the group consisting of oxygen, sulfur and nitrogen (NH). Heteroalkynyl residues may preferably comprise 1, 2 or 3 heteroatom(s) independently selected from the group consisting of oxygen, sulfur and nitrogen (NH) as chain link(s). Heteroalkynyl residues may preferably be 2- to 12-membered, particularly preferably 2- to 6-membered.

Examples of suitable unsubstituted heteroalkynyl residues include —CH$_2$—O—C—CH—CH$_2$—CH$_2$—O—C≡CH, —CH$_2$—O—C≡C—CH$_3$, —CH$_2$—CH$_2$—O—C≡C—CH$_3$, —CH$_2$—S—C≡CH, —CH$_2$—CH$_2$—S—C≡CH, —CH$_2$—S—C≡C—CH$_3$, —CH$_2$—CH$_2$—S—C≡C—CH$_3$.

Examples of suitable substituted heteroalkynyl residues include —CH$_2$—O—C—CH—CH$_2$—CH$_2$—O—C≡C—I, —CHF—O—C≡CH$_3$, —CHF—CH$_2$—O—C≡C—CH$_3$, —CH$_2$—S—C≡C—Cl, —CH$_2$—CH$_2$—S—C≡C—Cl, —CHF—S—C≡C—CH$_3$, —CHF—CH$_2$—S—C≡C—CH$_3$.

For the purposes of the present invention, the term "cycloalkyl" means a cyclic saturated hydrocarbon residue, with preferably 3, 4, 5, 6, 7, 8 or 9 C atoms, particularly preferably with 3, 4, 5, 6 or 7 C atoms, very particularly preferably with 5 or 6 C atoms, wherein the residue may be unsubstituted or monosubstituted or identically or differently polysubstituted. Examples of suitable C$_{3-9}$ cycloalkyl residues, which may in each case be unsubstituted or mono- or polysubstituted, include, for example, cyclopropyl, cyclobutyl, cyclopentyl, cyclohexyl, cycloheptyl, cyclooctyl and cyclononyl. Suitable C$_{3-7}$ cycloalkyl residues which may be mentioned are cyclopropyl, cyclobutyl, cyclopentyl, cyclohexyl and cycloheptyl.

For the purposes of the present invention, the term "cycloalkenyl" means a cyclic unsaturated hydrocarbon residue with preferably 3, 4, 5, 6, 7, 8 or 9 C atoms, particularly preferably with 3, 4, 5, 6 or 7 C atoms, very particularly preferably with 5 or 6 C atoms, which comprises at least one double bond, preferably one double bond, and may be unsubstituted or monosubstituted or identically or differently polysubstituted. Suitable C$_{3-9}$-cycloalkenyl residues, which may in each case be unsubstituted or mono- or polysubstituted, include cyclobutenyl, cyclopentenyl, cyclohexenyl, cycloheptenyl, cyclononenyl and cyclooctenyl. Suitable C$_{5-6}$ cycloalkenyl residues which may be mentioned are cyclopentenyl and cyclohexenyl.

For the purposes of the present invention, the term "heterocycloalkyl" means a cyclic saturated hydrocarbon residue with preferably 3, 4, 5, 6, 7, 8 or 9 C atoms, particularly preferably with 3, 4, 5, 6 or 7 C atoms, very particularly preferably with 5 or 6 C atoms, in which one or more C atoms have in each case been replaced by a heteroatom independently selected from the group consisting of oxygen, sulfur and nitrogen (NH). Heterocycloalkyl residues may preferably comprise 1, 2 or 3 heteroatom(s) independently selected from the group consisting of oxygen, sulfur and nitrogen (NH) as ring member(s). A heterocycloalkyl residue may be unsubstituted or monosubstituted or identically or differently polysubstituted. Heterocycloalkyl residues may preferably be 3- to 9-membered, particularly preferably 3- to 7-membered, very particularly preferably 5- to 7-membered. Examples of suitable 3- to 9-membered heterocycloalkyl residues, which may in each case be unsubstituted or mono- or polysubstituted, include imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1,3)-dioxolan-2-yl, isoxazolidinyl, isothioazolidinyl, pyrazolidinyl, oxazolidinyl, (1,2,4)-oxadiazolidinyl, (1,2,4)-thiadiazolidinyl, (1,2,4)-triazolidin-3-yl, (1,3,4)-thiadiazolidin-2-yl, (1,3,4)-triazolidin-1-yl, (1,3,4)-triazolidin-2-yl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,3)-dithian-2-yl and (1,3)-thiazolidinyl. Examples of 5- to 7-membered heterocycloalkyl residues which may be mentioned are imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, diazepanyl and (1,3)-dioxolan-2-yl.

For the purposes of the present invention, the term "heterocycloalkenyl" means a cyclic unsaturated hydrocarbon residue with preferably 4, 5, 6, 7, 8 or 9 C atoms, particularly preferably with 4, 5, 6 or 7 C atoms, very particularly preferably with 5 or 6 C atoms, which comprises at least one double bond, preferably one double bond, and in which one or more C atoms have in each case been replaced by a heteroatom independently selected from the group consisting of oxygen, sulfur and nitrogen (NH). Heterocycloalkenyl residues may preferably comprise 1, 2 or 3 heteroatom(s) independently selected from the group consisting of oxygen, sulfur and nitrogen (NH) as ring member(s). A heterocycloalkenyl residue may be unsubstituted or monosubstituted or identically or differently polysubstituted. Heterocycloalkenyl residues may preferably be 4- to 9-membered, particularly preferably 4- to 7-membered, very particularly preferably 5- to 7-membered. Examples of suitable heterocycloalkenyl residues or of suitable 5- to 7-membered heterocycloalkenyl residues, which in each case may be unsubstituted or mono- or polysubstituted, include (2,3)-dihydrofuranyl, (2,5)-dihydrofuranyl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, (3,4,5,6)-tetrahydropyridin-2-yl, (1,2,5,6)-tetrahydropyridin-1-yl, (1,2)-dihydropyridin-1-yl, (1,4)-dihydropyridin-1-yl, dihydropyranyl and (1,2,3,4)-tetrahydropyridin-1-yl.

The cycloalkyl residue, heterocycloalkyl residue, cycloalkenyl residue or heterocyclalkenyl residue may for the purposes of the present invention be fused (anellated) with an unsubstituted or at least monosubstituted mono- or bicyclic ring system. For the purposes of the present invention, a mono- or bicyclic ring system should be understood to mean mono- or bicyclic hydrocarbon residues which may be saturated, unsaturated or aromatic and optionally comprise one or more heteroatoms as ring members. Preferably, the rings of the above-stated mono- or bicyclic ring systems are in each case 4-, 5- or 6-membered and may in each case preferably optionally comprise 0, 1, 2, 3, 4 or 5 heteroatom(s), particularly preferably optionally 0, 1 or 2 heteroatom(s) as ring member(s), which are independently selected from the group consisting of oxygen, nitrogen and sulfur. If a bicyclic ring system is present, the different rings may, in each case mutually independently, exhibit a different degree of saturation, i.e. be saturated, unsaturated or aromatic.

If one or more of the substituents comprises a monocyclic or bicyclic ring system, which is mono- or polysubstituted, this may preferably be optionally substituted with 1, 2, 3, 4 or 5, particularly preferably with optionally 1, 2 or 3, substituents which may be independently selected from the group consisting of F, Cl, Br, I, —CN, —NO$_2$, —OH, —SH, —NH$_2$, oxo (=O), thioxo (=S), —C(=O)—OH, $C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —(CH$_2$)—O—$C_{1-5}$-alkyl, —S—$C_{1-5}$-alkyl, —S-phenyl, —S—CH$_2$-phenyl, —O—$C_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—$C_{1-5}$-alkyl, —S(=O)—$C_{1-5}$-alkyl, —NH—$C_{1-5}$-alkyl, —N($C_{1-5}$-alkyl)($C_{1-5}$-alkyl), —C(=O)—O—$C_{1-5}$-alkyl, —C(=O)—H, —C(=O)—$C_{1-5}$-alkyl, —CH$_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—NH$_2$, —C(=O)—NH—$C_{1-5}$-alkyl, —C(=O)—N($C_{1-5}$-alkyl)$_2$, pyrazolyl, phenyl, furyl (furanyl), thiadiazolyl, thiophenyl (thienyl) and benzyl, wherein the above-stated $C_{1-5}$ alkyl residues may in each case be linear or branched and the cyclic substituents or the cyclic residues of these substituents themselves may in each case be unsubstituted or optionally substituted with 1, 2, 3, 4 or 5, preferably with optionally 1, 2, 3 or 4, substituents independently selected from the group consisting of F, Cl, Br, I, —CN, —CF$_3$, —OH, —NH$_2$, —O—CF$_3$, —SH, —O—$C_{1-5}$-alkyl, —O-phenyl, —O—CH$_2$-phenyl, —(CH$_2$)—O—$C_{1-5}$-alkyl, —S—$C_{1-5}$-alkyl, —S-phenyl, —S—CH$_2$-phenyl, —$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —C(=O)—O—$C_{1-5}$-Alkyl and —C(=O)—CF$_3$.

Particularly preferably, the substituents may in each case be independently selected from the group consisting of F, Cl, Br, I, —CN, —NO$_2$, —OH, —SH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —NH$_2$, oxo (=O), —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl, wherein the cyclic substituents or the cyclic residues of these substituents themselves may be optionally substituted with 1, 2, 3, 4, or 5, preferably with optionally 1, 2, 3 or 4, substituents independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl, tert.-butyl, ethenyl, allyl, ethynyl, propynyl, —C≡C—Si(CH$_3$)$_3$, —C≡C—Si(C$_2$H$_5$)$_3$, —C(=O)—O—$C_{1-5}$-alkyl and —C(=O)—CF$_3$.

Examples of suitable cycloalkyl residues, heterocycloalkyl residues, cycloalkenyl residues and heterocycloalkenyl residues, which may in each case be unsubstituted or mono- or polysubstituted and are fused with a mono- or bicyclic ring system, include (1,2,3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1.4]dioxinyl, benzo[1.3]dioxolyl, (3,4)-dihydro-2H-benzo[1.4]oxazinyl, octahydro-1H-isoindolyl, [1,3,4,9]-tetrahydro-b-carbolinyl and octahydro-pyrrolo[3,4-c]pyrrolyl.

For the purposes of the present invention, the cycloalkyl residue, heterocycloalkyl residue, cycloalkenyl residue or heterocyclalkenyl residue may, together with a further cycloalkyl residue, heterocycloalkyl residue, cycloalkenyl residue or heterocyclalkenyl residue, form a spirocyclic residue via a common carbon atom in the ring. Examples of suitable spirocyclic residues include an 8-azaspiro[4.5]decyl residue and a (1,4)-dioxo-8-aza-spiro[4.5]decyl residue.

If one or more of the substituents denote a cycloalkyl residue, heterocycloalkyl residue, cycloalkenyl residue or heterocycloalkenyl residue or comprise such a residue, which is mono- or polysubstituted, this may preferably be optionally substituted with 1, 2, 3, 4 or 5, particularly preferably with optionally 1, 2 or 3, substituents independently selected from the group consisting of F, Cl, Br, I, —CN, —CF$_3$, —OH, —NH$_2$, —O—CF$_3$, —SH, —O—$C_{1-5}$-alkyl, —O-phenyl, —O—CH$_2$-phenyl, —(CH$_2$)—O—$C_{1-5}$-alkyl, —S—$C_{1-5}$-alkyl, —S-phenyl, —S—CH$_2$-phenyl, —$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —C(=O)—O—$C_{1-5}$-alkyl, —C(=O)—CF$_3$, —S(=O)$_2$—$C_{1-5}$-alkyl, —S(=O)—$C_{1-5}$-alkyl, —S(=O)$_2$-phenyl, oxo (=O), thioxo (=S), —N($C_{1-5}$-alkyl)$_2$, —N(H)($C_{1-5}$-alkyl), —NO$_2$, —S—CF$_3$, —C(=O)—OH, —NH—S(=O)$_2$—$C_{1-5}$-alkyl, —NH—C(=O)—$C_{1-5}$-alkyl, —NH—C(=O)—O—$C_{1-5}$-alkyl, —NH—C(=O)—CF$_3$, —C(=O)—H, —C(=O)—$C_{1-5}$-alkyl, —C(=O)—NH$_2$, —C(=O)—N($C_{1-5}$-alkyl)$_2$, —C(=O)—N(H)($C_{1-5}$-alkyl); —(CH$_2$)-pyrrolidinyl, benzyl, phenethyl, naphthyl, —(CH$_2$)-naphthyl and phenyl, wherein the above-stated $C_{1-5}$ alkyl residues may in each case be linear or branched and the cyclic substituents or the cyclic residues of these substituents themselves may be in each case unsubstituted or substituted with 1, 2, 3, 4 or 5, preferably with 1, 2, 3 or 4, substituents independently selected from the group consisting of F, Cl, Br, I, —CN, —CF$_3$, —OH, —NH$_2$, —O—CF$_3$, —SH, —O—$C_{1-5}$-alkyl, —O-phenyl, —O—CH$_2$-phenyl, —(CH$_2$)—O—$C_{1-5}$-alkyl, —S—$C_{1-5}$-alkyl, —S-phenyl, —S—CH$_2$-phenyl, —$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —C(=O)—O—$C_{1-5}$-alkyl and —C(=O)—CF$_3$.

Particularly preferably, the substituents may in each case be independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —C≡C—Si(CH$_3$)$_3$, —C≡C—Si(C$_2$H$_5$)$_3$, —OH, —O-phenyl, —O—CH$_2$-phenyl, oxo, thioxo, —O—CH$_3$, —O—C$_2$H$_5$, —O—C$_3$H$_7$, —(CH$_2$)—O—CH$_3$, —(CH$_2$)—O—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH—S(=O)$_2$—CH$_3$, —C(=O)—OH, —C(=O)—H; —C(=O)—CH$_3$, —C(=O)—C$_2$H$_5$, —C(=O)—N(CH$_3$)$_2$, —C(=O)—NH—CH$_3$, —C(=O)—NH$_2$, —NH—C(=O)—CF$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$, benzyl, —CH$_2$-naphthyl and phenyl, wherein the cyclic substituents or the cyclic residues of these substituents may be substituted with 1, 2, 3, 4 or 5, preferably with 1, 2 or 3, substituents independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl, tert.-butyl, ethenyl, allyl, ethynyl, propynyl, —C≡C—Si(CH$_3$)$_3$, —C≡C—Si(C$_2$H$_5$)$_3$, —C(═O)—O—C$_{1-5}$-alkyl and —C(═O)—CF$_3$.

For the purposes of the present invention, the term "aryl" means a mono- or polycyclic, preferably a mono- or bicyclic, aromatic hydrocarbon residue with preferably 6, 10 or 14 C atoms. An aryl residue may be unsubstituted or monosubstituted or identically or differently polysubstituted. Examples of suitable aryl residues which may be mentioned are phenyl, 1-naphthyl, 2-naphthyl and anthracenyl. An aryl residue is particularly preferably a phenyl residue.

For the purposes of the present invention, the term "heteroaryl" means a monocyclic or polycyclic, preferably a mono-, bi- or tricyclic aromatic hydrocarbon residue with preferably 5, 6, 7, 8, 9, 10, 11, 12, 13 or 14 C atoms, particularly preferably with 5, 6, 9, 10, 13 or 14 C atoms, very particularly preferably with 5 or 6 C atoms, in which one or more C atoms have in each case been replaced by a heteroatom independently selected from the group consisting of oxygen, sulfur and nitrogen (NH). Heteroaryl residues may preferably comprise 1, 2, 3, 4 or 5, particularly preferably 1, 2 or 3, heteroatom(s) independently selected from the group consisting of oxygen, sulfur and nitrogen (NH) as ring member(s). A heteroaryl residue may be unsubstituted or monosubstituted or identically or differently polysubstituted. Examples of suitable heteroaryl residues include indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, pyrimidinyl, indazolyl, quinoxalinyl, quinazolinyl, quinolinyl, naphthridinyl, thieno[2,3-d]pyrimidinyl and isoquinolinyl.

For the purposes of the present invention aryl or heteroaryl residues may be fused (anellated) with a mono- or bicyclic ring system. Examples of aryl residues which are fused with a mono- or bicyclic ring system include (2,3)-dihydrobenzo[b]thiophenyl, (2,3)-dihydro-1H-indenyl, indolinyl, (2,3)-dihydrobenzofuranyl, (2,3)-dihydrobenzo[d]oxazolyl, benzo[d][1,3]dioxolyl, benzo[d][1,3]oxathiolyl, isoindolinyl, (1,3)-diyhydroisobenzofuranyl, (1,3)-dihydrobenzo[c]thiophenyl, (1,2,3,4)-tetrahydronaphthyl, (1,2,3,4)-tetrahydroquinolinyl, chromanyl, thiochromanyl, (1,2,3,4)-tetrahydroisoquinolinyl, (1,2,3,4)-tetrahydroquinoxalinyl, (3,4)-dihydro-2H-benzo[b][1,4]oxazinyl, (3,4)-dihydro-2H-benzo[b][1,4]thiazinyl, (2,3)-dihydrobenzo[b][1,4]dioxinyl, (2,3)-dihydrobenzo[b][1,4]oxathiinyl, (6,7,8,9)-tetrahydro-5H-benzo[7]annulenyl, (2,3,4,5)-tetrahydro-1H-benzo[b]azepinyl and (2,3,4,5)-tetrahydro-1H-benzo[c]azepinyl.

Unless otherwise indicated, if one or more of the substituents denote an aryl or heteroaryl residue or comprise an aryl or heteroaryl residue, which is mono- or polysubstituted, these aryl or heteroaryl residues may preferably be optionally substituted with 1, 2, 3, 4 or 5, particularly preferably optionally 1, 2 or 3, substituents independently selected from the group consisting of F, Cl, Br, I, —CN, —CH$_2$—CN, —NO$_2$, —OH, —SH, —NH$_2$, —C(═O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, —S(═O)$_2$—C$_{1-5}$-alkyl, —S(═O)—C$_{1-5}$-alkyl, —NH—C$_{1-5}$-alkyl, —N(C$_{1-5}$-alkyl)$_2$, —C(═O)—O—C$_{1-5}$-alkyl, —C(═O)—O-phenyl, —C(═O)—H; —C(═O)—C$_{1-5}$-alkyl, —CH$_2$—O—C(═O)-phenyl, —O—C(═O)—C$_{1-5}$-alkyl, —O—C(═O)-phenyl, —NH—S(═O)$_2$—C$_{1-5}$-alkyl, —NH—C(═O)—C$_{1-5}$-alkyl, —C(═O)—NH$_2$, —C(═O)—NH—C$_{1-5}$-alkyl, —C(═O)—N(C$_{1-5}$-alkyl)$_2$, —C(═O)—N(C$_{1-5}$-alkyl)(phenyl), —C(═O)—NH-phenyl, —S(═O)$_2$—NH$_2$, —S(═O)$_2$—NH—C$_{1-5}$-alkyl, —S(═O)$_2$—N(C$_{1-5}$-alkyl)$_2$, —S(═O)$_2$—NH-phenyl, [1,2,3]-thiadiazolyl, cyclopropyl, cyclobutyl, cyclopentyl, cyclohexyl, piperazinyl, pyrrolidinyl, piperidinyl, pyrazolyl, phenyl, furyl (furanyl), thiazolyl, thiadiazolyl, thiophenyl (thienyl), benzyl and phenethyl, wherein the above-stated C$_{1-5}$ alkyl residues may in each case be linear or branched and the cyclic substituents or the cyclic residues of these substituents themselves may in each case be unsubstituted or optionally substituted with 1, 2, 3, 4 or 5, preferably with optionally 1, 2, 3 or 4, substituents independently selected from the group consisting of F, Cl, Br, I, —CN, —NO$_2$, —OH, —SH, —NH$_2$, —C(═O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F.

Particularly preferably, the substituents may in each case be independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —NH$_2$, —C(═O)—OH, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(═O)-phenyl, —NH—S(═O)$_2$—CH$_3$, —C(═O)—O—CH$_3$, —C(═O)—O—C$_2$H$_5$, —C(═O)—O—C(CH$_3$)$_3$, —C(═O)—H, —C(═O)—CH$_3$, —C(═O)—C$_2$H$_5$, —NH—C(═O)—CH$_3$, —NH—C(═O)—C$_2$H$_5$, —O—C(═O)-phenyl, —C(═O)—NH$_2$, —C(═O)—NH—CH$_3$, —C(═O)—N(CH$_3$)$_2$, —C(═O)—O—CH(CH$_3$)$_2$, —C(═O)—O—(CH$_2$)$_3$—CH$_3$, —C(═O)—O-phenyl, —O—C(═O)—CH$_3$, —O—C(═O)—C$_2$H$_5$, —C(═O)—NH—C$_2$H$_5$, —C(═O)—NH—C(CH$_3$)$_3$, —C(═O)—N(C$_2$H$_5$)$_2$, —C(═O)—NH-phenyl, —C(═O)—N(CH$_3$)-phenyl, —C(═O)—N(C$_2$H$_5$)-phenyl, —S(═O)—NH$_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5, preferably with optionally 1, 2, 3 or 4, substituents independently selected from the group consisting of F, Cl, Br, I, —CN, —NO$_2$, —OH, —SH, —NH$_2$, —C(═O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

Very particularly preferably, a substituted aryl residue may be selected from the group consisting of 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, 2-methylaminophenyl, 3-methylaminophenyl, 4-methylaminophenyl, 2-acetylphenyl, 3-acetylphenyl, 4-acetylphenyl, 2-methylsulfinylphenyl, 3-methylsulfinylphenyl, 4-methylsulfinylphenyl, 2-methylsulfonylphenyl, 3-methylsulfonylphenyl, 4-methylsulfonylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert.-butylphenyl, 3-tert.-butylphenyl, 4-tert.-butylphenyl, 2-carboxyphenyl, 3-carboxyphenyl, 4-carboxyphenyl, 2-ethenylphenyl, 3-ethenylphenyl, 4-ethenylphenyl, 2-ethynylphenyl, 3-ethynylphenyl, 4-ethynylphenyl, 2-allylphenyl, 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, 3-ethoxymethylphenyl, 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethyl ester phenyl, 3-carboxymethyl ester phenyl, 4-carboxymethyl ester phenyl, 2-carboxyethyl ester phenyl, 3-carboxyethyl ester phenyl, 4-carboxyethyl ester phenyl, 2-carboxy-tert.-butyl ester phenyl, 3-carboxy-tert.-butyl ester phenyl, 4-carboxy-tert.-butyl ester phenyl, 2-methylmercaptophenyl, 3-methylmercaptophenyl, 4-methylmercaptophenyl, 2-ethylmercaptophenyl, 3-ethylmercaptophenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxyphenyl, 3-trifluoromethoxyphenyl, 4-trifluoromethoxyphenyl, 2-fluoro-3-trifluoromethylphenyl, 2-fluoro-4-methylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dibromophenyl, (2,4)-dimethylphenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, 3-chloro-5-methylphenyl, (3,4)-dichlorophenyl, (3,4)-dimethylphenyl, 3-methyl-4-methoxyphenyl, 4-chloro-3-nitrophenyl, (3,4)-dimethoxyphenyl, 4-fluoro-3-trifluoromethylphenyl, 3-fluoro-4-trifluoromethylphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 3-fluoro-4-methylphenyl, 3-fluoro-5-methylphenyl, 2-fluoro-3-methylphenyl, 4-methyl-3-nitrophenyl, (3,5)-dimethoxyphenyl, (3,5)-dimethylphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (3,4,5)-trimethoxyphenyl, (2,3,4,5)-tetrafluorophenyl, 4-methoxy-(2,3,6)-trimethylphenyl, 4-methoxy-(2,3,6)-trimethylphenyl, 4-chloro-2,5-dimethylphenyl, 2-chloro-6-fluoro-3-methylphenyl, 6-chloro-2-fluoro-3-methyl, (2,4,6)-trimethylphenyl and (2,3,4,5,6)-pentafluorophenyl.

Very particularly preferably, a substituted heteroaryl residue may be selected from the group consisting of 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, 4-cyanothiazol-2-yl, 5-cyanothiazol-2-yl, 4-methoxythiazol-2-yl, 5-methoxythiazol-2-yl, 4-methyloxazol-2-yl, 5-methyloxazol-2-yl, 4-trifluormethyloxazol-2-yl, 5-trifluormethyloxazol-2-yl, 4-chlorooxazol-2-yl, 5-chlorooxazol-2-yl, 4-bromooxazol-2-yl, 5-bromooxazol-2-yl, 4-fluorooxazol-2-yl, 5-fluorooxazol-2-yl, 4-cyanooxazol-2-yl, 5-cyanooxazol-2-yl, 4-methoxy-oxazol-2-yl, 5-methoxy-oxazol-2-yl, 2-methyl-[1,2,4]-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl and 2-cyano-(1,2,4)-oxadiazol-5-yl.

For the purposes of the present invention, the term "alkylene" covers acyclic saturated hydrocarbon chains, which join an aryl, heteroaryl, cycloalkyl, heterocycloalkyl, cycloalkenyl or heterocycloalkenyl residue with the compounds corresponding to formula I or with another substituent. Alkylene chains may be branched or straight-chain and unsubstituted or at least monosubstituted with, as in the case of $C_{1-12}$ alkylene, 1 to 12 (i.e. 1, 2, 3, 4, 5, 6, 7, 8, 9, 10, 11 or 12) C atoms, with, as in the case of $C_{1-6}$ alkylene, 1 to 6 (i.e. 1, 2, 3, 4, 5 or 6) C atoms or with, as in the case of $C_{1-3}$ alkylene, 1 to 3 (i.e. 1, 2 or 3) C atoms. Examples include $C_{1-6}$ alkylene groups such as —(CH$_2$)—, —(CH$_2$)$_2$—, —C(H)(CH$_3$)—, —(CH$_2$)$_3$—, —(CH$_2$)$_4$—, —(CH$_2$)$_5$—, —C(CH$_3$)$_2$—, —C(H)(CH$_3$)—, —C(H)(C(H)(CH$_3$)$_2$)- and C(C$_2$H$_5$)(H)—. Examples of suitable $C_{1-3}$ alkylene groups include —(CH$_2$)—, —(CH$_2$)$_2$— and —(CH$_2$)$_3$—.

For the purposes of the present invention, the term "alkenylene" covers acyclic unsaturated hydrocarbon chains, which join an aryl, heteroaryl, cycloalkyl, heterocycloalkyl, cycloalkenyl or heterocycloalkenyl residue with the compounds corresponding to formula I or with another substituent. Alkenylene chains comprise at least one double bond, preferably 1, 2 or 3 double bonds, and may be branched or straight-chain and unsubstituted or at least monosubstituted with, as in the case of $C_{2-12}$ alkenylene, 2 to 12 (i.e. 2, 3, 4, 5, 6, 7, 8, 9, 10, 11 or 12) C atoms, with, as in the case of $C_{2-6}$ alkenylene, 2 to 6 (i.e. 2, 3, 4, 5 or 6) C atoms or with, as in the case of $C_{2-3}$ alkenylene, 2 to 3 (i.e. 2 or 3) C atoms. Examples which may be mentioned are $C_{2-3}$ alkenylene groups such as —CH=CH— and —CH$_2$—CH=CH—.

For the purposes of the present invention, the term "alkynylene" covers acyclic unsaturated hydrocarbon chains, which join an aryl, heteroaryl, cycloalkyl, heterocycloalkyl, cycloalkenyl or heterocycloalkenyl residue with the compounds corresponding to formula I or with another substituent. Alkynylene chains comprise at least one triple bond, preferably 1 or 2 triple bonds, and may be branched or straight-chain and unsubstituted or at least monosubstituted with, as in the case of $C_{2-12}$ alkynylene, 2 to 12 (i.e. 2, 3, 4, 5, 6, 7, 8, 9, 10, 11 or 12) C atoms, with, as in the case of $C_{2-6}$ alkynylene, 2 to 6 (i.e. 2, 3, 4, 5 or 6) C atoms or with, as in the case of $C_{2-3}$ alkynylene, 2 to 3 (i.e. 2 or 3) C atoms. Examples which may be mentioned are $C_{2-3}$ alkynylene groups such as —C≡C— and —CH$_2$—C≡C—.

The term "heteroalkylene" denotes an alkylene chain as described above in which one or more C atoms have in each case been replaced by a heteroatom independently selected from the group consisting of oxygen, sulfur and nitrogen (NH). Heteroalkylene groups may preferably comprise 1, 2 or 3 heteroatom(s), particularly preferably one heteroatom, selected from the group consisting of oxygen, sulfur and nitrogen (NH) as chain link(s). Heteroalkylene groups may preferably be 2- to 12-membered, particularly preferably 2- to 6-membered, very particularly preferably 2- or 3-membered. Examples include heteroalkylene groups such as —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —CH$_2$—NH—CH$_2$—, —CH$_2$—NH— and —CH$_2$—CH$_2$—NH—CH$_2$—.

The term "heteroalkenylene" denotes an alkenylene chain as described above in which one or more C atoms have in each case been replaced by a heteroatom independently selected from the group consisting of oxygen, sulfur and nitrogen (NH). Heteroalkenylene groups may preferably comprise 1, 2 or 3 heteroatom(s), particularly preferably 1 heteroatom, selected from the group consisting of oxygen, sulfur and nitrogen (NH) as chain link(s). Heteroalkenylene groups may preferably be 2- to 12-membered, particularly preferably 2- to 6-membered, very particularly preferably 2- or 3-membered. Examples which may be mentioned are heteroalkenylene groups such as —CH=CH—NH—, —CH=CH—O— and —CH=CH—S.

If one or more of the substituents denote an alkylene, alkenylene, alkynylene, heteroalkylene or heteroalkenylene group or comprise such a group, which is mono- or polysubstituted, this may preferably be optionally substituted with 1, 2, 3, 4 or 5, particularly preferably with optionally 1, 2 or 3, substituents independently selected from the group consisting of phenyl, F, Cl, Br, I, —NO$_2$, —CN, —OH, —O-phenyl, —O—CH$_2$-phenyl, —SH, —S-phenyl, —S—CH$_2$-phenyl, —NH$_2$, —N(C$_{1-5}$-alkyl)$_2$, —NH-phenyl, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated-C$_{1-5}$ alkyl residues may in each case be linear or branched and the above-stated phenyl residues may be substituted with 1, 2, 3, 4 or 5, preferably with 1, 2, 3 or 4, substituents independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

Particularly preferably, alkylene, alkenylene, alkynylene, heteroalkylene or heteroalkenylene groups may be substituted with 1, 2 or 3 substituents independently selected from the group consisting of phenyl, F, Cl, Br, I, —NO$_2$, —CN, —OH, —O-phenyl, —SH, —S-phenyl, —C(=O)—O—CH$_3$, —C(=O)—O—C$_2$H$_5$, —NH$_2$, —N(CH$_3$)$_2$, —N(C$_2$H$_5$)$_2$ and —N(CH$_3$)(C$_2$H$_5$), wherein the phenyl residue may be substituted with 1, 2, 3, 4 or 5 substituents independently selected from the group consisting of F, Cl, Br, I, —OH, —SH, —NO$_2$, —CN, —O—CH$_3$, —O—CF$_3$ and —O—C$_2$H$_5$.

Preference is given to 1,3-disubstituted 4-methyl-1H-pyrrole-2-carboxamides corresponding to the foregoing formula I, in which $R^1$ denotes $C_{1-6}$ alkyl, $C_{2-6}$ alkenyl or $C_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$, —C(=O)—O—C(CH$_3$)$_3$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluoyl), —N(C$_2$H$_5$)-(p-toluoyl), —N(CH$_3$)-(p-toluoyl) and —NH—C(=O)—O—C(CH$_3$)$_3$; 2- to 6-membered heteroalkyl, which is in each case unsubstituted or optionally substituted with 1, 2, 3, 4 or 5 substituents independently selected from the group consisting of F, Cl, Br, I, —NO$_2$, —CN, —OH, —SH and —NH$_2$ and in each case 1 or 2 heteroatom(s) independently selected from the group consisting of oxygen, sulfur and nitrogen (NH) as chain link(s); $C_{3-7}$-cycloalkyl, $C_{5-6}$-cycloalkenyl, 5- to 7-membered heterocycloalkyl, 5- to 7-membered heterocycloalkenyl, (1,2,3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1.4]dioxinyl or benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—$CH_3$, —O—$C_2H_5$, —O—$C_3H_7$, —O-phenyl, —O—$CH_2$-phenyl, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —S—$CH_3$, —S—$C_2H_5$, —C(=O)—$CH_3$, —C(=O)—$C_2H_5$, —C(=O)—$C(CH_3)_3$, —C(=O)—NH—$CH_3$, —C(=O)—NH—$C_2H_5$, —$CH_2$-naphthyl, benzyl and phenyl and/or in each case may be attached via an unsubstituted $C_{1-3}$ alkylene, $C_{2-3}$ alkenylene or $C_{2-3}$ alkynylene group and/or in each case may comprise 1 or 2 heteroatom(s) independently selected from the group consisting of oxygen, sulfur and nitrogen (NH) as ring member(s); phenyl, which may in each case be attached via a $C_{1-3}$ alkylene, $C_{2-3}$ alkenylene or $C_{2-3}$ alkynylene group, which is in each case unsubstituted or substituted with 1 or 2 substituents selected from the group consisting of F, C, Br, —C(=O)—O—$CH_3$ and —C(=O)—O—$C_2H_5$, or via a —$CH_2$—$CH_2$—O—, —$CH_2$—O— or —$CH_2$—$CH_2$—$CH_2$—O— group and/or is in each case unsubstituted or substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—$Si(CH_3)_3$, —C≡C—$Si(C_2H_5)_3$, —$CH_2$—O—$CH_3$, —$CH_2$—O—$C_2H_5$, —$NH_2$, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, —$N(CH_3)_2$, —$N(C_2H_5)_2$, —NH—$CH_3$, —NH—$C_2H_5$, —$CH_2$—O—C(=O)-phenyl, —NH—S(=O)$_2$—$CH_3$, —C(=O)—H, —C(=O)—$CH_3$, —C(=O)—$C_2H_5$, —NH—C(=O)—$CH_3$, —NH—C(=O)—$C_2H_5$, —O—C(=O)-phenyl, —C(=O)—$NH_2$, —C(=O)—NH—$CH_3$, —C(=O)—NH—$C_2H_5$, —C(=O)—NH—$C(CH_3)_3$, —C(=O)—N($C_2H_5$)$_2$, —S(=O)—$NH_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —$NO_2$, —OH, —SH, —$NH_2$, methyl, ethyl, n-propyl, isopropyl, n-butyl, isobutyl, 2-butyl, tert.-butyl, n-pentyl, neopentyl, ethenyl, allyl, ethynyl, propynyl, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$ or —NH—C(=O)—$R^5$;

or optionally substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—$Si(CH_3)_3$, —C≡C—$Si(C_2H_5)_3$, —$CH_2$—O—$CH_3$, —$CH_2$—O—$C_2H_5$, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, —$N(CH_3)_2$, —$N(C_2H_5)_2$, —NH—$CH_3$, —NH—$C_2H_5$, —$CH_2$—O—C(=O)-phenyl, —NH—S(=O)$_2$—$CH_3$, —C(=O)—O—$CH_3$, —C(=O)—O—$C_2H_5$, —C(=O)—O—$C(CH_3)_3$, —C(=O)—H, —C(=O)—$CH_3$, —C(=O)—$C_2H_5$, —NH—C(=O)—$CH_3$, —NH—C(=O)—$C_2H_5$, —O—C(=O)-phenyl, —C(=O)—$NH_2$, —C(=O)—NH—$CH_3$, —C(=O)—N($CH_3$)$_2$, —C(=O)—O—$CH(CH_3)_2$, —C(=O)—O—($CH_2$)$_3$—$CH_3$, —C(=O)—O-phenyl, —O—C(=O)—$CH_3$, —O—C(=O)—$C_2H_5$, —C(=O)—NH—$C_2H_5$, —C(=O)—NH—$C(CH_3)_3$, —C(=O)—N($C_2H_5$)$_2$, —C(=O)—NH-phenyl, —C(=O)—N($CH_3$)-phenyl, —C(=O)—N($C_2H_5$)-phenyl, —S(=O)—$NH_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —$NO_2$, —OH, —SH, —$NH_2$, methyl, ethyl, n-propyl, isopropyl, n-butyl, isobutyl, 2-butyl, tert.-butyl, n-pentyl, neopentyl, ethenyl, allyl, ethynyl, propynyl, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$ or —NH—C(=O)—$R^5$;

and in each case the other residues have the above-stated meanings, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which $R^2$ denotes H; $C_{1-6}$ alkyl, $C_{2-6}$ alkenyl or $C_{2-6}$ alkynyl, which may in each case be unsubstituted or optionally substituted with 1, 2, 3, 4 or 5 substituents independently selected from the group consisting of F, Cl, Br, I, —$NO_2$, —CN, —OH, —SH, —$NH_2$, —$N(CH_3)_2$, —$N(C_2H_5)_2$, —$N(CH_3)(C_2H_5)$, —C(=O)—OH, —C(=O)—O—$CH_3$, —C(=O)—O—$C_2H_5$, —C(=O)—O—$C(CH_3)_3$, —C(=O)—O—$CH_2$-phenyl, —C(=O)—NH-naphthyl, —N($CH_3$)-phenyl, —N($C_2H_5$)-phenyl, —N($C_2H_5$)-(m-toluoyl), —N($C_2H_5$)-(p-toluoyl), —N($CH_3$)—(p-toluoyl) and —NH—C(=O)—O—$C(CH_3)_3$; or a residue selected from the group consisting of phenyl and naphthyl, which may in each case be attached via a $C_{1-3}$ alkylene, $C_{2-3}$ alkenylene or $C_{2-3}$ alkynylene group and/or is in each case unsubstituted or optionally substituted with 1, 2, 3, 4 or 5 substituents independently selected from the group consisting of F, Cl, Br, I, —CN, —CH₂—CN, —NO₂, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH₃)₃, —C≡C—Si(C₂H₅)₃, —CH₂—CH₃, —CH₂—O—C₂H₅, —NH₂, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂, —S—CH₂F, —S(=O)₂-phenyl, pyrazolyl, —N(CH₃)₂, —N(C₂H₅)₂, —NH—CH₃, —NH—C₂H₅, —CH₂—O—C(=O)-phenyl, —NH—S(=O)₂—CH₃, —C(=O)—H, —C(=O)—CH₃, —C(=O)—C₂H₅, —NH—C(=O)—CH₃, —NH—C(=O)—C₂H₅, —O—C(=O)-phenyl, —C(=O)—NH₂, —C(=O)—NH—CH₃, —C(=O)—NH—C₂H₅, —C(=O)—NH—C(CH₃)₃, —C(=O)—N(C₂H₅)₂, —S(=O)—NH₂, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO₂, —OH, —SH, —NH₂, methyl, ethyl, n-propyl, isopropyl, n-butyl, isobutyl, 2-butyl, tert.-butyl, n-pentyl, neopentyl, —O—CH₃, —O—C₂H₅, —O—C₃H₇, —O—C(CH₃)₃, —CF₃, —CHF₂, —CH₂F, —O—CF₃, —O—CHF₂ and —O—CH₂F;

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which $R^1$ and $R^2$, together with the nitrogen atom to which they are bound, form a residue selected from the group consisting of imidazolidinyl, [1,3,4,9]-tetrahydro-[b]-carbolinyl, piperidinyl, morpholinyl, thiomorpholinyl, pyrrolidinyl, piperazinyl, azepanyl, diazepanyl and (1,4)-dioxo-8-aza-spiro[4.5]decyl, which is in each case unsubstituted or substituted with 1 or 2 $R^6$ residues;

and in each case the other residues have the above-stated meanings, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which $R^3$ denotes $C_{1-6}$ alkyl, $C_{2-6}$ alkenyl or $C_{2-6}$ alkynyl, which is in each case unsubstituted or optionally substituted with 1, 2, 3, 4 or 5 substituents independently selected from the group consisting of F, Cl, Br, I, —NO₂, —CN, —OH, —SH, —NH₂, —N(CH₃)₂, —N(C₂H₅)₂, —N(CH₃)(C₂H₅), —C(=O)—OH, —C(=O)—O—CH₃, —C(=O)—O—C₂H₅, —C(=O)—O—C(CH₃)₃, —C(=O)—O—CH₂-phenyl, —C(=O)—NH-naphthyl, —N(CH₃)-phenyl, —N(C₂H₅)-phenyl, —N(C₂H₅)-(m-toluoyl), —N(C₂H₅)-(p-toluoyl), —N(CH₃)—(p-toluoyl) and —NH—C(=O)—O—C(CH₃)₃; or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which is in each case attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —CH₂—CN, —NO₂, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —CH₂—O—CH₃, —CH₂—O—C₂H₅, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂, —S—CH₂F, —N(CH₃)₂, —N(C₂H₅)₂, —NH—CH₃, —NH—C₂H₅, —C(=O)—H, —C(=O)—CH₃, —C(=O)—C₂H₅, —C(=O)—NH₂, —C(=O)—NH—CH₃ and —C(=O)—N(CH₃)₂;

and in each case the other residues have the above-stated meanings, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which $R^4$ denotes phenyl, which is in each case unsubstituted or substituted with 1, 2, 3, 4 or 5 substituents independently selected from the group consisting of F, Cl, Br, I, —CN, —CH₂—CN, —OH, —SH, —NH₂, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH₃)₃, —C≡C—Si(C₂H₅)₃, —S—CH₃, —S—C₂H₅, —S-phenyl, —S—CH₂-phenyl, —O—CH₃, —O—C₂H₅, —O—C₃H₇, —O—C(CH₃)₃, —O-phenyl, —O—CH₂-phenyl, —CF₃, —CHF₂, —CH₂F, —O—CF₃, —O—CHF₂, —O—CH₂F, —C(=O)—CF₃, —S—CF₃, —S—CHF₂, —S—CH₂F, —S(=O)₂-phenyl, —N(CH₃)₂, —N(C₂H₅)₂, —NH—CH₃, —NH—C₂H₅, —C(=O)—O—CH₃, —C(=O)—O—C₂H₅, —C(=O)—O—C(CH₃)₃, —C(=O)—H, —C(=O)—CH₃, —C(=O)—C₂H₅, —NH—C(=O)—CH₃, —NH—C(=O)—C₂H₅, —C(=O)—NH₂, —C(=O)—NH—CH₃, —C(=O)—N(CH₃)₂, —S(=O)₂—NH₂, —S(=O)₂—NH-phenyl, [1,2,3]-thiadiazolyl, cyclopropyl, cyclobutyl, cyclopentyl, cyclohexyl, phenyl, benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F; or a residue selected from the group consisting of thienyl, furyl, pyrrolyl, pyrazolyl, pyrazinyl, pyranyl, triazolyl, pyridinyl, imidazolyl, thiadiazolyl, oxadiazolyl and pyridazinyl, which is in each case unsubstituted or optionally substituted with 1, 2, 3, 4 or 5 substituents independently selected from the group consisting of F, Cl, Br, I, —CN, —NO$_2$, —OH, —CH$_2$—CN, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —S—CH$_3$, —S—C$_2$H$_5$, —S-phenyl, —S—CH$_2$-phenyl, —O—CH$_3$, —O—C$_2$H$_5$, —O—C$_3$H$_7$, —O—C(CH$_3$)$_3$, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —S(=O)$_2$—NH$_2$, cyclopropyl, cyclobutyl, cyclopentyl, cyclohexyl, phenyl and benzyl, wherein the cyclic substituents or the cyclic residues of these substituents themselves may in each case be unsubstituted or optionally substituted with 1, 2, 3, 4, or 5 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

and in each case the other residues have the above-stated meanings, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which R$^5$ denotes a residue selected from the group consisting of phenyl, naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—H, —C(=O)—CH$_3$, —C(=O)—C$_2$H$_5$, —C(=O)—NH$_2$, —C(=O)—NH—CH$_3$ and —C(=O)—N(CH$_3$)$_2$;

and in each case the other residues have the above-stated meanings, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which R$^6$ denotes —OH; F; Cl; Br; I; —SH; —NO$_2$; —NH$_2$; —NH—C(=O)—O—R$^7$; —C(=O)—O—R$^8$; —C(=O)—R$^9$; or C$_{1-6}$ alkyl, C$_{2-6}$ alkenyl or C$_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —C(=O)-pyrrolidinyl, —C(=O)—N(CH$_3$)-phenyl and —C(=O)—NH—CH(CH$_3$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$; or C$_{3-7}$ cycloalkyl, C$_{5-6}$ cycloalkenyl, 5- to 7-membered heterocycloalkyl or 5- to 7-membered heterocycloalkenyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl and/or in each case may be attached via an unsubstituted C$_{1-3}$ alkylene, C$_{2-3}$ alkenylene or C$_{2-3}$ alkynylene group and/or in each case may comprise 1 or 2 heteroatom(s) independently selected from the group consisting of oxygen, sulfur and nitrogen (NH) as ring member(s); or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl, thieno[2,3-d]pyrimidinyl and isoquinolinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—NH—C$_2$H$_5$, —C(=O)—NH—C(CH$_3$)$_3$, —C(=O)—N(C$_2$H$_5$)$_2$, cyclopropyl, cyclobutyl, cyclopentyl, cyclohexyl, phenyl, furyl (furanyl) and benzyl, wherein the cyclic substituents or the cyclic residues of these substituents themselves may in each case optionally be substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

and in each case the other residues have the above-stated meanings, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which $R^7$, $R^8$ and $R^9$ each independently denote $C_{1-6}$ alkyl, $C_{2-6}$ alkenyl or $C_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$; or a residue selected from the group consisting of indolinyl, indanyl, (1,2,3,4)-tetrahydronaphthyl, (2,3)-dihydrobenzo[1.4]dioxinyl and benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl; or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—NH—C$_2$H$_5$, —C(=O)—NH—C(CH$_3$)$_3$, —C(=O)—N(C$_2$H$_5$)$_2$, cyclopropyl, cyclobutyl, cyclopentyl, cyclohexyl, phenyl, furyl (furanyl) and benzyl;

and in each case the other residues have the above-stated meanings, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particular preference is given to 1,3-disubstituted 4-methyl-1H-pyrrole-2-carboxamides corresponding to the foregoing formula I, in which $R^1$ denotes $C_{1-6}$ alkyl, $C_{2-6}$ alkenyl or —$C_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$, —C(=O)—O—C(CH$_3$)$_3$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluoyl), —N(C$_2$H$_5$)-(p-toluoyl), —N(CH$_3$)—(p-toluoyl) and —NH—C(=O)—O—C(CH$_3$)$_3$; or 2- to 6-membered heteroalkyl, which is in each case unsubstituted or optionally substituted with 1, 2, 3, 4 or 5 substituents independently selected from the group consisting of F, Cl, Br, I, —NO$_2$, —CN, —OH, —SH and —NH$_2$ and in each case 1 or 2 heteroatom(s) independently selected from the group consisting of oxygen, sulfur and nitrogen (NH) as chain link(s); or $C_{3-7}$-cycloalkyl, $C_{5-6}$-cycloalkenyl, 5- to 7-membered heterocycloalkyl, 5- to 7-membered heterocycloalkenyl, (1,2,3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1.4]dioxinyl or benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(═O)—C$_2$H$_5$, —C(═O)—C(CH$_3$)$_3$, —C(═O)—NH—CH$_3$, —C(═O)—NH—C$_2$H$_5$, —CH$_2$-naphthyl, benzyl and phenyl and/or in each case may be attached via an unsubstituted C$_{1-3}$ alkylene, C$_{2-3}$ alkenylene or C$_{2-3}$ alkynylene group and/or in each case may comprise 1 or 2 heteroatom(s) independently selected from the group consisting of oxygen, sulfur and nitrogen (NH) as ring member(s); or phenyl, which may in each case be attached via a C$_{1-3}$ alkylene, C$_{2-3}$ alkenylene or C$_{2-3}$ alkynylene group, which is in each case unsubstituted or substituted with 1 or 2 substituents selected from the group consisting of F, C, Br, —C(═O)—O—CH$_3$ and —C(═O)—O—C$_2$H$_5$, or via a —CH$_2$—CH$_2$—O—, —CH$_2$—O— or —CH$_2$—CH$_2$—CH$_2$—O— group and/or is in each case unsubstituted or substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —NH$_2$, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(═O)-phenyl, —NH—S(═O)$_2$—CH$_3$, —C(═O)—H, —C(═O)—CH$_3$, —C(═O)—C$_2$H$_5$, —NH—C(═O)—CH$_3$, —NH—C(═O)—C$_2$H$_5$, —O—C(═O)-phenyl, —C(═O)—NH$_2$, —C(═O)—NH—CH$_3$, —C(═O)—NH—C$_2$H$_5$, —C(═O)—NH—C(CH$_3$)$_3$, —C(═O)—N(C$_2$H$_5$)$_2$, —S(═O)—NH$_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, ethenyl, allyl, ethynyl, propynyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F and —O—CH$_2$F; or a residue selected from the group consisting of naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —NH$_2$, —C(═O)—OH, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(═O)-phenyl, —NH—S(═O)$_2$—CH$_3$, —C(═O)—O—CH$_3$, —C(═O)—O—C$_2$H$_5$, —C(═O)—O—C(CH$_3$)$_3$, —C(═O)—H, —C(═O)—CH$_3$, —C(═O)—C$_2$H$_5$, —NH—C(═O)—CH$_3$, —NH—C(═O)—C$_2$H$_5$, —O—C(═O)-phenyl, —C(═O)—NH$_2$, —C(═O)—NH—CH$_3$, —C(═O)—N(CH$_3$)$_2$, —C(═O)—O—CH(CH$_3$)$_2$, —C(═O)—O—(CH$_2$)$_3$—CH$_3$, —C(═O)—O-phenyl, —O—C(═O)—CH$_3$, —O—C(═O)—C$_2$H$_5$, —C(═O)—NH—C$_2$H$_5$, —C(═O)—NH—C(CH$_3$)$_3$, —C(═O)—N(C$_2$H$_5$)$_2$, —C(═O)—NH-phenyl, —C(═O)—N(CH$_3$)-phenyl, —C(═O)—N(C$_2$H$_5$)-phenyl, —S(═O)—NH$_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, ethenyl, allyl, ethynyl, propynyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F; or —NH—C(═O)—R$^5$;

$R^2$ denotes H; C$_{1-6}$-alkyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(═O)—OH, —C(═O)—O—CH$_3$, —C(═O)—O—C$_2$H$_5$, —C(═O)—O—C(CH$_3$)$_3$, —C(═O)—O—CH$_2$-phenyl, —C(═O)—NH-naphthyl, —N(CH$_3$)-phenyl, —N(C$_2$H$_5$)-phenyl, —N(C$_2$H$_5$)-(m-toluoyl), —N(C$_2$H$_5$)-(p-toluoyl), —N(CH$_3$)-(p-toluoyl) and —NH—C(═O)—O—C(CH$_3$)$_3$; or a residue selected from the group consisting of phenyl and naphthyl, which may in each case be attached via a C$_{1-3}$ alkylene, C$_{2-3}$ alkenylene or C$_{2-3}$ alkynylene group and/or is in each case unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —NH$_2$, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —N(CH$_3$)$_2$, —N(C$_2$H$_5$)$_2$, —NH—CH$_3$ and —NH—C$_2$H$_5$; or $R^1$ and $R^2$, together with the nitrogen atom to which they are bound, form a residue selected from the group consisting of:

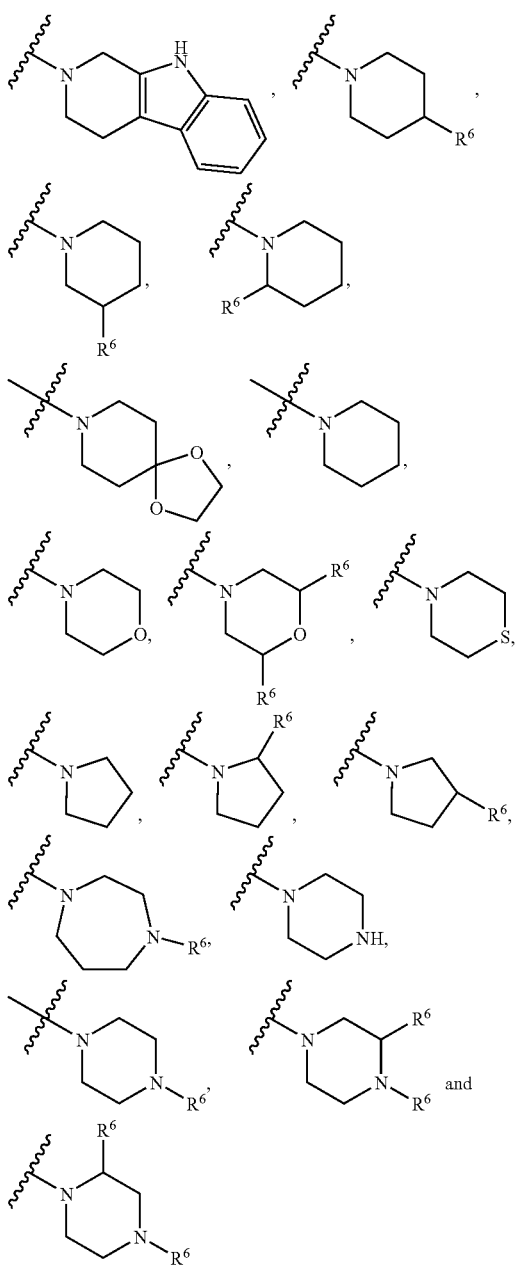

$R^3$ denotes $C_{1-6}$ alkyl, which is in each case unsubstituted or optionally substituted with 1, 2, 3, 4 or 5 substituents independently selected from the group consisting of F, Cl, Br, I, —$NO_2$, —CN, —OH, —SH, —$NH_2$, —$N(CH_3)_2$, —$N(C_2H_5)_2$, —$N(CH_3)(C_2H_5)$, —C(=O)—OH, —C(=O)—O—$CH_3$, —C(=O)—O—$C_2H_5$ and —C(=O)—O—$C(CH_3)_3$; or a residue selected from the group consisting of phenyl, isoxazolyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, pyridazinyl and isoquinolinyl, which is in each case attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —$CH_2$—O—$CH_3$, —$CH_2$—O—$C_2H_5$, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —$N(CH_3)_2$, —$N(C_2H_5)_2$, —NH—$CH_3$, —NH—$C_2H_5$, —C(=O)—H, —C(=O)—$CH_3$, —C(=O)—$C_2H_5$, —C(=O)—$NH_2$, —C(=O)—NH—$CH_3$ and —C(=O)—$N(CH_3)_2$;

$R^4$ denotes phenyl, which is in each case unsubstituted or substituted with 1, 2, 3, 4 or 5 substituents independently selected from the group consisting of F, Cl, Br, I, —CN, —$CH_2$—CN, —OH, —SH, —$NH_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—$Si(CH_3)_3$, —C≡C—$Si(C_2H_5)_3$, —S—$CH_3$, —S—$C_2H_5$, —S-phenyl, —S—$CH_2$-phenyl, —O—$CH_3$, —O—$C_2H_5$, —O—$C_3H_7$, —O—$C(CH_3)_3$, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —$N(CH_3)_2$, —$N(C_2H_5)_2$, —NH—$CH_3$, —NH—$C_2H_5$, —C(=O)—O—$CH_3$, —C(=O)—O—$C_2H_5$, —C(=O)—O—$C(CH_3)_3$, —C(=O)—H, —C(=O)—$CH_3$, —C(=O)—$C_2H_5$, —NH—C(=O)—$CH_3$, —NH—C(=O)—$C_2H_5$, —C(=O)—$NH_2$, —C(=O)—NH—$CH_3$, —C(=O)—$N(CH_3)_2$, —S(=O)$_2$—$NH_2$, —S(=O)$_2$—NH-phenyl, [1,2,3]-thiadiazolyl, cyclopropyl, cyclobutyl, cyclopentyl, cyclohexyl, phenyl, benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —$NO_2$, —OH, —SH, —$NH_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$; or a residue selected from the group consisting of thienyl, furyl, pyrrolyl, pyrazolyl, pyrazinyl, pyranyl, triazolyl, pyridinyl, imidazolyl, thiadiazolyl, oxadiazolyl and pyridazinyl, which is in each case unsubstituted or optionally substituted with 1, 2, 3, 4 or 5 substituents independently selected from the group consisting of F, Cl, Br, I, —CN, —$NO_2$, —OH, —$CH_2$—CN, —SH, —$NH_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —S—$CH_3$, —S—$C_2H_5$, —S-phenyl, —S—$CH_2$-phenyl, —O—$CH_3$, —O—$C_2H_5$, —O—$C_3H_7$, —O—$C(CH_3)_3$, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —$N(CH_3)_2$, —$N(C_2H_5)_2$, —NH—$CH_3$, —NH—$C_2H_5$, —C(=O)—O—$CH_3$, —C(=O)—O—$C_2H_5$, —C(=O)—O—$C(CH_3)_3$, —C(=O)—H, —C(=O)—$CH_3$, —C(=O)—$C_2H_5$, —NH—C(=O)—$CH_3$, —NH—C(=O)—$C_2H_5$, —C(=O)—$NH_2$, —C(=O)—NH—$CH_3$, —C(=O)—$N(CH_3)_2$, —S(=O)$_2$—$NH_2$, cyclopropyl, cyclobutyl, cyclopentyl, cyclohexyl, phenyl and benzyl, wherein the cyclic substituents or the cyclic residues of these substituents themselves may in each case be unsubstituted or optionally substituted with 1, 2, 3, 4, or 5 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

$R^5$ denotes a residue selected from the group consisting of phenyl, naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$ and —NH—C$_2$H$_5$;

$R^6$ denotes —OH; F; Cl; Br; I; —SH; —NO$_2$; —NH$_2$; —NH—C(=O)—O—R$^7$; —C(=O)—O—R$^8$; —C(=O)—R$^9$; or C$_{1-6}$ alkyl, C$_{2-6}$ alkenyl or C$_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —C(=O)-pyrrolidinyl, —C(=O)—N(CH$_3$)-phenyl and —C(=O)—NH—CH (CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$; or C$_{3-7}$ cycloalkyl, C$_{5-6}$ cycloalkenyl, 5- to 7-membered heterocycloalkyl or 5- to 7-membered heterocycloalkenyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl and/or in each case may be attached via an unsubstituted C$_{1-3}$ alkylene, C$_{2-3}$ alkenylene or C$_{2-3}$ alkynylene group and/or in each case may comprise 1 or 2 heteroatom(s) independently selected from the group consisting of oxygen, sulfur and nitrogen (NH) as ring member(s); or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl, thieno[2,3-d]pyrimidinyl and isoquinolinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—NH—C$_2$H$_5$, —C(=O)—NH—C(CH$_3$)$_3$, —C(=O)—N (C$_2$H$_5$)$_2$, cyclopropyl, cyclobutyl, cyclopentyl, cyclohexyl, phenyl, furyl (furanyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

$R^7$, $R^8$ and $R^9$ each independently denote C$_{1-6}$ alkyl, C$_{2-6}$ alkenyl or C$_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$; or a residue selected from the group consisting of indolinyl, indanyl, (1,2,3,4)-tetrahydronaphthyl, (2,3)-dihydrobenzo[1.4]dioxinyl and benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl; or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—NH—C$_2$H$_5$, —C(=O)—NH—C(CH$_3$)$_3$, —C(=O)—N(C$_2$H$_5$)$_2$, cyclopropyl, cyclobutyl, cyclopentyl, cyclohexyl, phenyl, furyl (furanyl) and benzyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are 1,3-disubstituted 4-methyl-1H-pyrrole-2-carboxamides of the above-stated general formula I, in which $R^1$ denotes an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or optionally substituted with 1, 2, 3, 4 or 5 substituents independently selected from the group consisting of F, Cl, Br, I, —CN, —OH, —SH, —NH$_2$, —N(CH$_3$)$_2$, —N(C$_2$H$_5$)$_2$, —N(CH$_3$)(C$_2$H$_5$), —C(=O)—O—CH$_3$, —C(=O)—O—C$_2$H$_5$, —C(=O)—O—C(CH$_3$)$_3$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluoyl), —N(C$_2$H$_5$)-(p-toluoyl), —N(CH$_3$)-(p-toluoyl) and —NH—C(=O)—O—C(CH$_3$)$_3$; or a heteroalkyl residue selected from the group consisting of —CH$_2$—O—CH$_3$, —CH$_2$—O—C$_2$H$_5$, —CH$_2$—CH$_2$—O—CH$_3$, —CH$_2$—CH$_2$—O—C$_2$H$_5$, —CH$_2$—CH$_2$—CH$_2$—O—CH$_3$ and —CH$_2$—CH$_2$—CH$_2$—O—C$_2$H$_5$, which is in each case unsubstituted or optionally substituted with 1, 2, 3, 4 or 5 substituents independently selected from the group consisting of F, Cl and Br; or a residue selected from the group consisting of cyclopropyl, cyclobutyl, cyclopentyl, cyclohexyl, cycloheptyl, cyclohexenyl, cyclopentenyl, pyrrolidinyl, tetrahydrothiophenyl, tetrahydrofuranyl, piperidinyl, morpholinyl, piperazinyl, azepanyl, diazepanyl, (1,2,3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1.4]dioxinyl and benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, —O—CH$_3$, —O—C$_2$H$_5$, —O—C$_3$H$_7$, —O-phenyl, —O—CH$_2$-phenyl, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl and/or may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group; or phenyl, which may in each case be attached via a —CH$_2$—CH$_2$—O—, —CH$_2$—O—, —CH$_2$—CH$_2$—CH$_2$—O—, —CH [C(=O)—O—CH$_3$]—CH$_2$—, —CH [C(=O)—O—C$_2$H$_5$]—CH$_2$—, —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group and/or is in each case unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —N(CH$_3$)$_2$, —N(C$_2$H$_5$)$_2$, —NH—CH$_3$, —NH—C$_2$H$_5$, —NH—S(=O)$_2$—CH$_3$, —C(=O)—H, —C(=O)—CH$_3$, —C(=O)—C$_2$H$_5$, —NH—C(=O)—CH$_3$, —NH—C(=O)—C$_2$H$_5$, —S(=O)—NH$_2$, [1,2,3]-thiadiazolyl, cyclopropyl, cyclobutyl, cyclopentyl, cyclohexyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, methyl, ethyl, n-propyl, isopropyl, n-butyl, isobutyl, 2-butyl, tert.-butyl, —O—CH$_3$, —O—C$_2$H$_5$, —O—C$_3$H$_7$ and —O—C(CH$_3$)$_3$; or a residue selected from the group consisting of naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$ group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —C(=O)—NH$_2$, —C(=O)—NH—CH$_3$, —C(=O)—N(CH$_3$)$_2$, —C(=O)—O—CH(CH$_3$)$_2$ and —C(=O)—O—(CH$_2$)$_3$—CH$_3$; or or —NH—C(=O)—R$^5$;

$R^2$ denotes H; an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or a residue selected from the group consisting of phenyl and naphthyl, which may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group and/or is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, isobutyl, 2-butyl, tert.-butyl, n-pentyl, neopentyl, —O—CH$_3$, —O—C$_2$H$_5$, -Q-C$_3$H$_7$, —O—C(CH$_3$)$_3$, —CF$_3$, —CHF$_2$ and —CH$_2$F; or $R^1$ and $R^2$, together with the nitrogen atom to which they are bound, form a residue selected from the group consisting of

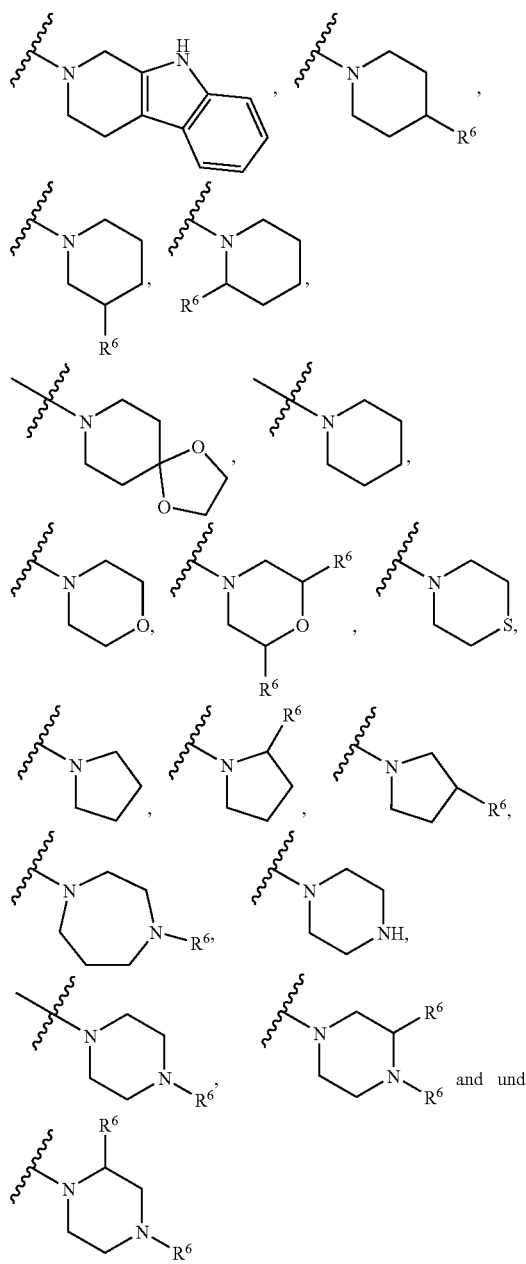

$R^3$ denotes an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or a phenyl residue, which is in each case attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$ group and/or is in each case unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —CH$_2$—O—CH$_3$, —CH$_2$—O—C$_2$H$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F; and $R^4$ denotes phenyl, which is in each case unsubstituted or substituted with 1, 2, 3, 4 or 5 substituents independently selected from the group consisting of F, Cl, Br, I, —CN, —CH$_2$—CN, —OH, —SH, —NH$_2$, —C(=O)—OH, methyl, ethyl, n-propyl, isopropyl, n-butyl, isobutyl, 2-butyl, tert.-butyl, n-pentyl, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$ and —NH—CH$_3$; or a residue selected from the group consisting of thienyl, furyl, pyrrolyl, pyrazolyl, pyrazinyl, pyranyl, triazolyl, pyridinyl, imidazolyl, thiadiazolyl, oxadiazolyl and pyridazinyl, which is in each case unsubstituted or optionally substituted with 1, 2, 3, 4 or 5 substituents independently selected from the group consisting of F, Cl, Br, I, —CN, —NO$_2$, —OH, —CH$_2$—CN, —SH, —NH$_2$, —C(=O)—OH, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$ and —NH—CH$_3$;

$R^5$ denotes a residue selected from the group consisting of phenyl and naphthyl, which is in each case unsubstituted or substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$ and —NH—C$_2$H$_5$;

$R^6$ denotes —OH; F; Cl; Br; I; —SH; —NO$_2$; —NH$_2$; —NH—C(=O)—O—$R^7$; —C(=O)—O—$R^8$; —C(=O)—$R^9$; or an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)-pyrrolidinyl, —C(=O)—N(CH$_3$)-phenyl and —C(=O)—NH—CH(CH$_3$)$_2$, —C(=O)—OH, —C(=O)—O—$CH_3$, —C(=O)—O—$C_2H_5$ and —C(=O)—O—C($CH_3$)$_3$; or a residue selected from the group consisting of cyclopropyl, cyclobutyl, cyclopentyl, cyclohexyl, cycloheptyl, cyclohexenyl, cyclopentenyl, pyrrolidinyl, tetrahydrothiophenyl, tetrahydrofuranyl, piperidinyl, morpholinyl, piperazinyl, azepanyl and diazepanyl, which is in each case unsubstituted or optionally substituted with 1, 2, 3, 4 or 5 substituents independently selected from the group consisting of methyl, ethyl, n-propyl, isopropyl, n-butyl, 2-butyl, isobutyl, tert.-butyl, —OH, —O—$CH_3$, —O—$C_2H_5$, —O—$C_3H_7$, —O—$CF_3$, —C(=O)—$CH_3$, —C(=O)—$C_2H_5$, —C(=O)—C($CH_3$)$_3$, —C(=O)—NH—$CH_3$ and —C(=O)—NH—$C_2H_5$ and/or may in each case be attached via a —$CH_2$—, —CH($CH_3$)—, —$CH_2$—$CH_2$—, —CH($CH_3$)—$CH_2$—, —$CH_2$—CH($CH_3$)— or —$CH_2$—$CH_2$—$CH_2$— group; or a residue selected from the group consisting of phenyl, naphthyl, indolizinyl, benzimidazolyl, tetrazolyl, triazinyl, isoxazolyl, phthalazinyl, thienyl, furyl, pyrrolyl, pyrazolyl, pyrazinyl, pyranyl, triazinyl, pyridinyl, imidazolyl, indolyl, isoindolyl, thiazolyl, thiadiazolyl, oxazolyl, oxadiazolyl, isoxazolyl, pyridazinyl, thieno[2,3-d]pyrimidinyl and isoquinolinyl, which may in each case be attached via a $CH_2$—, —CH($CH_3$)—, —$CH_2$—$CH_2$—, —CH($CH_3$)—$CH_2$—, —$CH_2$—CH($CH_3$)— or —$CH_2$—$CH_2$—$CH_2$— group and/or is unsubstituted or optionally substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —C(=O)—H, —C(=O)—$CH_3$ and —C(=O)—$C_2H_5$; and $R^7$, $R^3$ and $R^9$ each independently denote an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or optionally substituted with 1, 2, 3, 4 or 5 substituents independently selected from the group consisting of F, Cl, Br, I, —$NO_2$, —CN, —OH, —SH, —$NH_2$, —N($CH_3$)$_2$, —N($C_2H_5$)$_2$ and —N($CH_3$)($C_2H_5$); or a residue selected from the group consisting of indolinyl, indanyl, (1,2,3,4)-tetrahydronaphthyl, (2,3)-dihydrobenzo[1.4]dioxinyl and benzo[1.3]dioxolyl, which is in each case unsubstituted; or a residue selected from the group consisting of phenyl, naphthyl, isoxazolyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a —$CH_2$, —CH($CH_3$)—, —$CH_2$—$CH_2$—, —CH($CH_3$)—$CH_2$—, —$CH_2$—CH($CH_3$)— or —$CH_2$—$CH_2$—$CH_2$ group and/or is in each case unsubstituted or optionally substituted with 1, 2, 3, 4 or 5 substituents independently selected from the group consisting of F, Cl, Br, I, —CN, —$NO_2$, —O-phenyl, methyl, ethyl, n-propyl, isopropyl, n-butyl, isobutyl, 2-butyl, tert.-butyl, n-pentyl, neopentyl, —S—$CH_3$, —S—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$ and —O—$CH_2F$;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particular preference is given to 1,3-disubstituted 4-methyl-1H-pyrrole-2-carboxamides of the above-stated general formula I, in which $R^1$ denotes an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or substituted with 1, 2 or 3 substituents independently selected from the group consisting of —CN, —OH, —N($CH_3$)$_2$, —N($C_2H_5$)$_2$—C(=O)—O—$CH_3$, —C(=O)—O—$C_2H_5$, —C(=O)—O—C($CH_3$)$_3$, —C(=O)—O—$CH_2$-phenyl, —C(=O)—NH-naphthyl, —N($CH_3$)-phenyl, —N($C_2H_5$)-(m-toluoyl) and —N($C_2H_5$)-(p-toluoyl); or a heteroalkyl residue selected from the group consisting of —$CH_2$—O—$CH_3$, —$CH_2$—O—$C_2H_5$, —$CH_2$—$CH_2$—O—$CH_3$, —$CH_2$—$CH_2$—O—$C_2H_5$, —$CH_2$—$CH_2$—$CH_2$—O—$CH_3$ and —$CH_2$—$CH_2$—$CH_2$—O—$C_2H_5$; or a residue selected from the group consisting of cyclopropyl, cyclobutyl, cyclopentyl, cyclohexyl, cycloheptyl, pyrrolidinyl, tetrahydrofuranyl, piperidinyl, morpholinyl, piperazinyl, azepanyl, dihydrofuran-2(3H)-only, indanyl and (1,2,3,4)-tetrahydronaphthyl, which in each case may be unsubstituted or optionally substituted with 1, 2, 3, 4 or 5 substituents independently selected from the group consisting of methyl, ethyl, n-propyl, isopropyl, n-butyl, 2-butyl, isobutyl, tert.-butyl, —$CH_2$-naphthyl, —O-phenyl, —O—$CH_2$-phenyl, benzyl and phenyl and/or may in each case be attached via a —$CH_2$—, —CH($CH_3$)—, —$CH_2$—$CH_2$—, —CH($CH_3$)—$CH_2$—, —$CH_2$—CH($CH_3$)— or —$CH_2$—$CH_2$—$CH_2$— group; or phenyl, which in each case may be attached via a —$CH_2$—$CH_2$—O—, —$CH_2$—O—, —$CH_2$—$CH_2$—$CH_2$—O—, —CH [C(=O)—O—$CH_3$]—$CH_2$—, —CH [C(=O)—O—$C_2H_5$]—$CH_2$—, —$CH_2$—, —CH($CH_3$)—, —$CH_2$—$CH_2$—, —CH($CH_3$)—$CH_2$—, —$CH_2$—CH($CH_3$)— or —$CH_2$—$CH_2$—$CH_2$— group and/or is in each case unsubstituted or optionally substituted with 1, 2, 3, 4 or 5 substituents independently selected from the group consisting of F, Cl, Br, I, —$CH_2$—CN, methyl, ethyl, n-propyl, isopropyl, n-butyl, isobutyl, 2-butyl, tert.-butyl, n-pentyl, neopentyl, —O-phenyl, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —N($CH_3$)$_2$, —N($C_2H_5$)$_2$, —S(=O)—$NH_2$ and [1,2,3]-thiadiazolyl; or a residue selected from the group consisting of thienyl, furyl, pyrrolyl, pyrazolyl, pyridinyl, imidazolyl, indolyl and isoindolyl, which may in each case be attached via a —$CH_2$—, —CH($CH_3$)—, —$CH_2$—$CH_2$—, —CH($CH_3$)—$CH_2$—, —$CH_2$—CH($CH_3$)— or —$CH_2$—$CH_2$—$CH_2$— group and/or is unsubstituted or optionally substituted with 1, 2 or 3 substituents independently selected from the group consisting of —$NO_2$, —OH, methyl, ethyl, n-propyl, isopropyl, n-butyl, isobutyl, 2-butyl, tert.-butyl, n-pentyl, and neopentyl; or —NH—C(=O)—$R^5$;

R² denotes H; an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or a residue selected from the group consisting of phenyl and naphthyl, which may in each case be attached via a —CH₂—, —CH(CH₃)—, —CH₂—CH₂—, —CH(CH₃)—CH₂—, —CH₂—CH(CH₃)— or —CH₂—CH₂—CH₂— group and/or in each case is unsubstituted or optionally substituted with 1, 2 or 3 substituents independently selected from the group consisting of —O—CH₃, —O—C₂H₅, —O—C₃H₇ and —O—C(CH₃)₃; or R¹ and R², together with the nitrogen atom to which they are bound, form a residue selected from the group consisting of

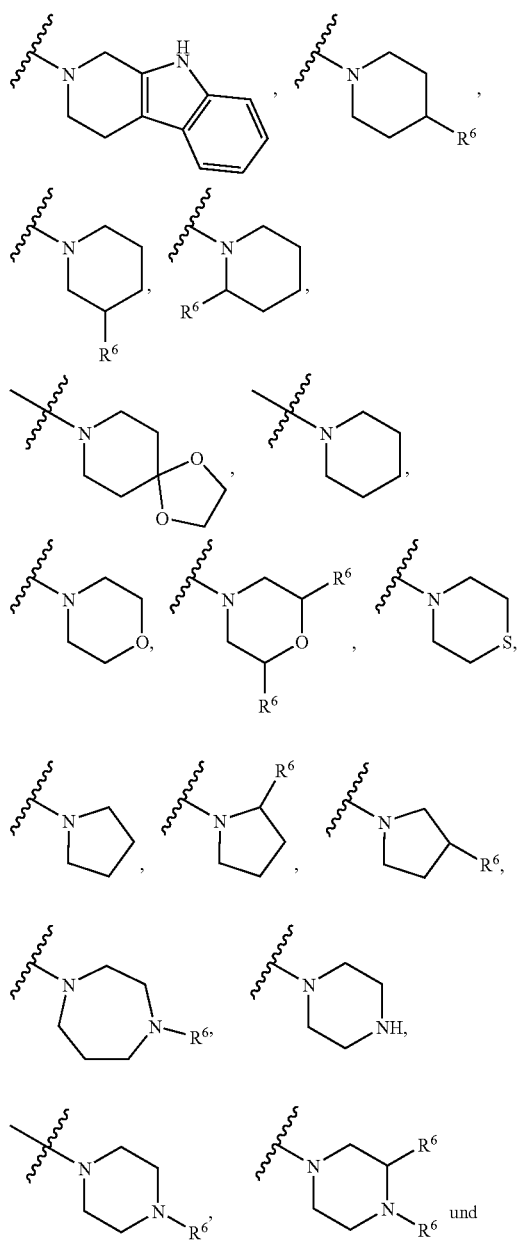

-continued

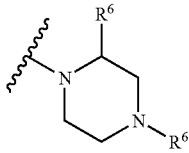

R³ denotes an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or a phenyl residue, which is in each case attached via a —CH₂—, —CH(CH₃)—, —CH₂—CH₂—, —CH(CH₃)—CH₂—, —CH₂—CH(CH₃)— or —CH₂—CH₂—CH₂ group and/or is in each case unsubstituted or optionally substituted with 1, and 4 or 5 substituents independently selected from the group consisting of F, Cl, Br, I, —CN, —CH₂—CN, —NO₂, methyl, ethyl, n-propyl, isopropyl, n-butyl, isobutyl, 2-butyl, tert.-butyl, n-pentyl, neopentyl, —O—CH₃, —O—C₂H₅, —O—C₃H₇, —O—C(CH₃)₃, —CF₃, —CHF₂, —CH₂F, —O—CF₃, —O—CHF₂ and —O—CH₂F;

R⁴ denotes phenyl, which is in each case unsubstituted or substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, n-pentyl, —O—CH₃, —O—C₂H₅, —O—C₃H₇, —O—C(CH₃)₃, —O—CF₃, —O—CHF₂ and —O—CH₂F; or a residue selected from the group consisting of thienyl, furyl and pyrrolyl, which is in each case unsubstituted or optionally substituted with 1, 2, 3, 4 or 5 substituents independently selected from the group consisting of F, Cl, Br, I, methyl, ethyl, n-propyl, isopropyl, n-butyl, isobutyl, 2-butyl, —O—CH₃, —O—C₂H₅, —O—C₃H₇ and —O—C(CH₃)₃;

R⁵ denotes a residue selected from the group consisting of phenyl and naphthyl, which is in each case unsubstituted or substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, —NH₂, —O—CH₃, —O—C₂H₅, —O—C₃H₇, —O—C(CH₃)₃, —N(CH₃)₂, —N(C₂H₅)₂, —NH—CH₃ and —NH—C₂H₅;

R⁶ denotes —OH; —NH—C(=O)—O—R⁷; —C(=O)—O—R⁸; —C(=O)—R⁹; or an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or substituted with 1, 2 or 3 substituents independently selected from the group consisting of —OH, —N(CH₃)₂, —N(C₂H₅)₂, —C(=O)-pyrrolidinyl —C(=O)—N(CH₃)-phenyl and —C(=O)—NH—CH(CH₃)₂; or a residue selected from the group consisting of cyclopropyl, cyclobutyl, cyclopentyl, cyclohexyl, cycloheptyl, pyrrolidinyl, piperidinyl and azepanyl, which is in each case unsubstituted and/or may in each case be attached via a —CH₂, —CH(CH₃)—, —CH₂—CH₂—, —CH(CH₃)—CH₂—, —CH₂—CH(CH₃)— or —CH₂—CH₂—CH₂ group; or a residue selected from the group consisting of phenyl, naphthyl, thienyl, furyl, pyrazinyl, pyridinyl, pyridazinyl and thieno[2,3-d]pyrimidinyl, which may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$ group and/or in each case is unsubstituted or optionally substituted with 1, 2, 3, 4 or 5 substituents independently selected from the group consisting of F, Cl, Br, I, —CN, methyl, tert.-butyl, —O—CH$_3$, —O—C$_2$H$_5$, —CF$_3$, —C(=O)—CH$_3$ and —C(=O)—C$_2$H$_5$; and R$^7$, R$^8$ and R$^9$ each independently denote an alkyl residue selected from the group consisting of methyl, ethyl, n-propyl, isopropyl, n-butyl, 2-butyl, isobutyl, tert.-butyl and n-pentyl, which is in each case unsubstituted; or a residue selected from the group consisting of (2,3)-dihydrobenzo[1.4]dioxinyl and benzo[1.3]dioxolyl, which is in each case unsubstituted; or a residue selected from the group consisting of phenyl, thienyl, furyl and pyrazinyl, which may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group and/or in each case unsubstituted or optionally substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$ and —O—C(CH$_3$)$_3$;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also very particularly preferred are 1,3-disubstituted 4-methyl-1H-pyrrole-2-carboxamides corresponding to the foregoing formula I, in which R$^1$ denotes a residue selected from the group consisting of —CH$_2$—CH$_2$—N(C$_2$H$_5$)-(m-toluoyl), —CH$_2$—CH$_2$—N(C$_2$H$_5$)-(p-toluoyl), —CH$_2$—CH$_2$—CH$_2$—N(CH$_3$)-phenyl, —CH$_2$—CH$_2$—CH$_2$—N(CH$_3$)$_2$, —CH$_2$—CH$_2$—CH$_2$—N(C$_2$H$_5$)$_2$, —CH(CH$_3$)—CH$_2$—CH$_2$—CH(CH$_3$)$_2$, —CH$_2$—CH$_2$—CN, —CH$_2$—CH$_2$—OH, —CH$_2$—CH$_2$—N(CH$_3$)$_2$, —CH$_2$—CH$_2$—N(C$_2$H$_5$)$_2$, —CH$_2$—CH$_2$—C(CH$_3$)$_3$, n-pentyl, n-butyl, methyl, ethyl, n-propyl, —CH[CH$_3$)—C(=O)—O—CH$_2$-phenyl, —CH[CH(CH$_3$)$_2$]—C(=O)—O—C(CH$_3$)$_3$, —CH$_2$—C(=O)—O—CH$_2$-phenyl, —CH$_2$—CH$_2$—C(=O)—O—C(CH$_3$)$_3$, —CH$_2$—CH$_2$—C(=O)—O—C$_2$H$_5$, —CH$_2$—C(=O)—NH-naphthyl and —CH$_2$—CH$_2$—CH$_2$—O—CH$_3$; or a residue selected from the group consisting of cyclopropyl, cyclobutyl, cyclopentyl, cyclohexyl, cycloheptyl, pyrrolidinyl, tetrahydrofuranyl, piperidinyl, morpholinyl, piperazinyl, azepanyl, dihydrofuran-2(3H)-only, indanyl and (1,2,3,4)-tetrahydronaphthyl, which is in each case unsubstituted or optionally substituted with 1, 2, 3, 4 or 5 substituents independently selected from the group consisting of methyl, ethyl, —CH$_2$-naphthyl, —O-phenyl, —O—CH$_2$-phenyl and benzyl and/or may in each case be attached via a —CH$_2$—, —CH$_2$—CH$_2$— or —CH$_2$—CH$_2$—CH$_2$— group; or phenyl, which may in each case be attached via a —CH$_2$—CH$_2$—O—, —CH[C(=O)—O—CH$_3$]—CH$_2$—, —CH[C(=O)—O—C$_2$H$_5$]—CH$_2$—, —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group and/or in each case may be unsubstituted or optionally substituted with 1, 2, 3, 4 or 5 substituents independently selected from the group consisting of F, Cl, Br, I, —CH$_2$—CN, methyl, ethyl, n-propyl, isopropyl, n-butyl, isobutyl, 2-butyl, tert.-butyl, —O-phenyl, —O—CH$_3$, —O—C$_2$H$_5$, —CF$_3$, —O—CF$_3$, —N(CH$_3$)$_2$, —N(C$_2$H$_5$)$_2$, —S(=O)—NH$_2$ and [1,2,3]-thiadiazolyl; or a residue selected from the group consisting of thienyl, furyl, pyridinyl, imidazolyl, indolyl and isoindolyl, which may in each case be attached via a —CH$_2$—, —CH$_2$—CH$_2$— or —CH$_2$—CH$_2$—CH$_2$— group and/or is unsubstituted or optionally substituted with 1, 2 or 3 substituents independently selected from the group consisting of —NO$_2$, —OH, methyl, ethyl and n-propyl; or —NH—C(=O)—R$^5$;

R$^2$ denotes H; an alkyl residue selected from the group consisting of methyl, ethyl and n-propyl, which is in each case unsubstituted; or a residue selected from the group consisting of phenyl and naphthyl, which may in each case be attached via a —CH$_2$ group and/or is in each case unsubstituted or substituted with 1, 2 or 3 substituents independently selected from the group consisting of —O—CH$_3$, —O—C$_2$H$_5$, —O—C$_3$H$_7$ and —O—C(CH$_3$)$_3$; or R$^1$ and R$^2$ together with the nitrogen atom to which they are bound form a residue selected from the group consisting of

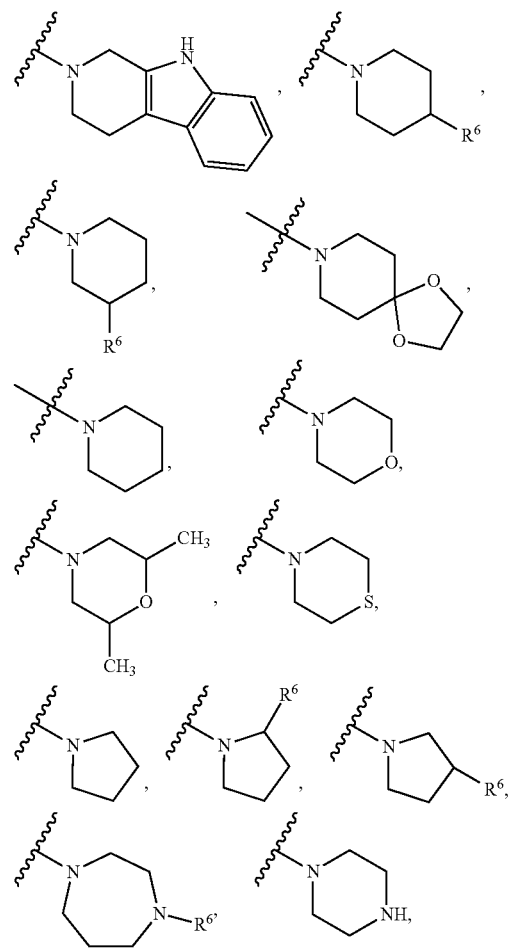

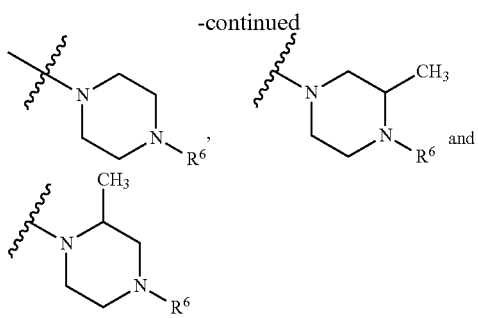

R³ denotes an alkyl residue selected from the group consisting of methyl, ethyl, n-propyl, isopropyl, n-butyl, 2-butyl, isobutyl and tert.-butyl, which is in each case unsubstituted; or
  a phenyl residue, which is in each case attached via a —CH₂ group and/or is in each case unsubstituted or optionally substituted with 1, 2, 3, 4 or 5 substituents independently selected from the group consisting of F, Cl, Br, methyl, ethyl, n-propyl, —O—CH₃, —O—C₂H₅, and —CF₃;

R⁴ denotes phenyl, which is in each case unsubstituted or substituted with 1, 2, 3, 4 or 5 substituents independently selected from the group consisting of F, Cl, Br, methyl, ethyl, n-propyl, —O—CH₃ and —O—C₂H₅; or
  a residue selected from the group consisting of thienyl, furyl and pyrrolyl, which is in each case unsubstituted;

R⁵ denotes a residue selected from the group consisting of phenyl and naphthyl, which in each case may be unsubstituted or substituted with 1, 2, 3, 4 or 5 substituents independently selected from the group consisting of F, Cl, Br, methyl, ethyl, —O—CH₃, —O—C₂H₅, —N(CH₃)₂, —N(C₂H₅)₂, —NH—CH₃ and —NH—C₂H₅;

R⁶ denotes —OH; —NH—C(=O)—O—R⁷; —C(=O)—O—R⁸; —C(=O)—R⁹; or
  a residue selected from the group consisting of methyl, ethyl, n-propyl, isopropyl, n-butyl, —CH₃, —CH(CH₃)₂, —CH₂—CH₂—OH, —CH₂—CH₂—N(CH₃)₂, —CH₂—CH₂—N(C₂H₅), —CH₂—C(=O)-pyrrolidinyl, —CH₂—C(=O)—NH—CH(CH₃)₂ and —CH₂—C(=O)—N(CH₃)— phenyl; or
  a residue selected from the group consisting of cyclopropyl, cyclobutyl, cyclopentyl, cyclohexyl, cycloheptyl, pyrrolidinyl, piperidinyl and azepanyl, which in each case may be unsubstituted and/or in each case may be attached via a —CH₂— group; or
  a residue selected from the group consisting of phenyl, naphthyl, thienyl, pyrazinyl, pyridinyl and thieno[2,3-d]pyrimidinyl, which may in each case be attached via a —CH₂—, —CH₂—CH₂ or —CH₂—CH₂—CH₂— group and/or is in each case unsubstituted or optionally substituted with 1, 2, 3, 4 or 5 substituents independently selected from the group consisting of F, Cl, Br, —CN, methyl, tert.-butyl, —O—CH₃, —O—C₂H₅, —CF₃, —C(=O)—CH₃ and —C(=O)—C₂H₅;

R⁷ denotes an alkyl residue selected from the group consisting of methyl, ethyl, n-propyl, isopropyl, n-butyl, 2-butyl, isobutyl, tert.-butyl, and n-pentyl, which is in each case unsubstituted;

R⁸ denotes an alkyl residue selected from the group consisting of methyl, ethyl, n-propyl, isopropyl, n-butyl, 2-butyl, isobutyl, tert.-butyl, and n-pentyl, which is in each case unsubstituted; or a phenyl or benzyl residue; and R⁹ denotes a residue selected from the group consisting of (2,3)-dihydrobenzo[1.4]dioxinyl and benzo[1.3]dioxolyl, which is in each case unsubstituted; or a residue selected from the group consisting of phenyl, thienyl, furyl and pyrazinyl, which may in each case be attached via a —CH₂—, —CH₂—CH₂— or —CH₂—CH₂—CH₂— group and/or in each case unsubstituted or optionally substituted with 1, 2, 3, 4 or 5 substituents independently selected from the group consisting of F, Cl, Br, methyl, ethyl, —O—CH₃ and —O—C₂H₅;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particular preference is given to 1,3-disubstituted 4-methyl-1H-pyrrole-2-carboxamides of the above-stated general formula I, selected from the group consisting of:

[1]  1-benzyl-4-methyl-3-p-tolyl-1H-pyrrole-2-carboxylic acid 4-[1,2,3]thiadiazol-4-ylbenzylamide,
[2]  3-furan-2-yl-1,4-dimethyl-1H-pyrrole-2-carboxylic acid 4-sulfamoylbenzylamide,
[3]  1-(4-fluorobenzyl)-3-furan-2-yl-4-methyl-1H-pyrrole-2-carboxylic acid 2,4-dimethoxybenzylamide,
[4]  1-butyl-4-methyl-3-p-tolyl-1H-pyrrole-2-carboxylic acid (2-pyridin-2-ylethyl)-amide,
[5]  1-(4-fluorobenzyl)-3-(4-methoxyphenyl)-4-methyl-1H-pyrrole-2-carboxylic acid [2-(5-hydroxy-1H-indol-3-yl)-ethyl]-amide,
[6]  (1,4-dimethyl-3-p-tolyl-1H-pyrrole-2-yl)-(4-pyrrolidin-1-ylpiperidin-1-yl)-methanone,
[7]  1-benzyl-3-furan-2-yl-4-methyl-1H-pyrrole-2-carboxylic acid 4-bromo-2-fluorobenzylamide,
[8]  [1-benzyl-3-(4-chlorophenyl)-4-methyl-1H-pyrrol-2-yl]-[4-(2-chlorophenyl)-piperazin-1-yl]-methanone,
[9]  1,4-dimethyl-3-phenyl-1H-pyrrole-2-carboxylic acid (3-dimethylamino-propyl)-amide,
[10] 1,4-dimethyl-3-p-tolyl-1H-pyrrole-2-carboxylic acid (2-pyrrolidin-1-ylethyl)-amide,
[11] 1-(4-fluorobenzyl)-3-furan-2-yl-4-methyl-1H-pyrrole-2-carboxylic acid 4-dimethylaminobenzylamide,
[12] 1-[4-(1-benzyl-4-methyl-3-phenyl-1H-pyrrole-2-carbonyl)-piperazin-1-yl]-2-phenylethanone,
[13] 1-benzyl-3-furan-2-yl-4-methyl-1H-pyrrole-2-carboxylic acid 2,5-difluorobenzylamide,
[14] 1-(2,6-dichlorobenzyl)-4-methyl-3-p-tolyl-1H-pyrrole-2-carboxylic acid 3,5-difluorobenzylamide,
[15] 1-(2-bromobenzyl)-3-(4-chlorophenyl)-4-methyl-1H-pyrrole-2-carboxylic acid (2-methylcyclohexyl)-amide,
[16] 1,4-dimethyl-3-p-tolyl-1H-pyrrole-2-carboxylic acid (3-morpholin-4-ylpropyl)-amide,
[17] 1-butyl-4-methyl-3-p-tolyl-1H-pyrrole-2-carboxylic acid (1,3-dimethylbutyl)-amide,
[18] [4-(2,4-dimethylphenyl)-piperazin-1-yl]-[4-methyl-1-(4-methylbenzyl)-3-p-tolyl-1H-pyrrol-2-yl]-methanone,
[19] 1-(2,6-dichlorobenzyl)-4-methyl-3-p-tolyl-1H-pyrrole-2-carboxylic acid methyl-(2-pyridin-2-ylethyl)-amide,
[20] 1,4-dimethyl-3-phenyl-1H-pyrrole-2-carboxylic acid (2-cyano-ethyl)-methylamide,
[21] 1-(2,6-dichlorobenzyl)-4-methyl-3-p-tolyl-1H-pyrrole-2-carboxylic acid (3-imidazol-1-ylpropyl)-amide,
[22] 1-(4-fluorobenzyl)-3-(4-methoxyphenyl)-4-methyl-1H-pyrrole-2-carboxylic acid (1,3-dimethylbutyl)-amide,
[23] 3-(4-methoxyphenyl)-1,4-dimethyl-1H-pyrrole-2-carboxylic acid 2-ethoxybenzylamide,

[24] (4-cycloheptylpiperazin-1-yl)-(1,4-dimethyl-3-p-tolyl-1H-pyrrol-2-yl)-methanone,
[25] 1-(4-fluorobenzyl)-3-(4-methoxyphenyl)-4-methyl-1H-pyrrole-2-carboxylic acid (2-dimethylamino-ethyl)-amide,
[26] 1-benzyl-4-methyl-3-phenyl-1H-pyrrole-2-carboxylic acid (pyridin-2-ylmethyl)-amide,
[27] 3-(4-chlorophenyl)-1-ethyl-4-methyl-1H-pyrrole-2-carboxylic acid [2-(4-chlorophenyl)-propyl]-amide,
[28] 3-(4-chlorophenyl)-1-(2-fluorobenzyl)-4-methyl-1H-pyrrole-2-carboxylic acid 3,5-difluorobenzylamide,
[29] 2-{[1-(4-fluorobenzyl)-3-(4-methoxyphenyl)-4-methyl-1H-pyrrole-2-carbonyl]-amino}-propionic acid benzyl ester,
[30] (1-benzyl-4-methyl-3-p-tolyl-1H-pyrrol-2-yl)-[4-(2-dimethylamino-ethyl)-piperazin-1-yl]-methanone,
[31] 3-furan-2-yl-1-(4-methoxybenzyl)-4-methyl-1H-pyrrole-2-carboxylic acid (3,3-dimethylbutyl)-amide,
[32] 3-(4-chlorophenyl)-1-isobutyl-4-methyl-1H-pyrrole-2-carboxylic acid 4-dimethylaminobenzylamide,
[33] 3-(4-chlorophenyl)-1-ethyl-4-methyl-1H-pyrrole-2-carboxylic acid (2-pyridin-2-ylethyl)-amide,
[34] 3-(4-chlorophenyl)-1-ethyl-4-methyl-1H-pyrrole-2-carboxylic acid 2,3-dimethoxybenzylamide,
[35] 1-(4-fluorobenzyl)-3-(4-methoxyphenyl)-4-methyl-1H-pyrrole-2-carboxylic acid (2-thiophen-2-ylethyl)-amide,
[36] 2-{[3-(4-chlorophenyl)-1-ethyl-4-methyl-1H-pyrrole-2-carbonyl]-amino}-3-methylbutyric acid tert.-butyl ester,
[37] 3-furan-2-yl-1-(4-methoxybenzyl)-4-methyl-1H-pyrrole-2-carboxylic acid (1,2,3,4-tetrahydro-naphthalen-1-yl)-amide,
[38] 3-furan-2-yl-4-methyl-1-(4-trifluoromethylbenzyl)-1H-pyrrole-2-carboxylic acid (2-pyrrolidin-1-ylethyl)-amide,
[39] {[1-(4-methoxybenzyl)-4-methyl-3-p-tolyl-1H-pyrrole-2-carbonyl]-methylamino}-acetic acid benzyl ester,
[40] 3-furan-2-yl-1-(4-methoxybenzyl)-4-methyl-1H-pyrrole-2-carboxylic acid [2-(1-methylpyrrolidin-2-yl)-ethyl]-amide,
[41] [4-(5-bromo-2-ethoxybenzyl)-piperazin-1-yl]-(1,4-dimethyl-3-phenyl-1H-pyrrol-2-yl)-methanone,
[42] (1-benzyl-3-furan-2-yl-4-methyl-1H-pyrrol-2-yl)-[4-(3-fluoro-4-methoxybenzyl)-piperazin-1-yl]-methanone,
[43] 3-{[3-(4-chlorophenyl)-1-ethyl-4-methyl-1H-pyrrole-2-carbonyl]-amino}-propionic acid tert.-butyl ester,
[44] 1-benzyl-4-methyl-3-phenyl-1H-pyrrole-2-carboxylic acid 3-methoxybenzylamide,
[45] (1-benzyl-3-furan-2-yl-4-methyl-1H-pyrrol-2-yl)-[4-(5-bromo-2-ethoxybenzyl)-piperazin-1-yl]-methanone,
[46] [3-(4-chlorophenyl)-1,4-dimethyl-1H-pyrrol-2-yl]-(4-o-tolylpiperazin-1-yl)-methanone,
[47] 1-(4-fluorobenzyl)-3-(4-methoxyphenyl)-4-methyl-1H-pyrrole-2-carboxylic acid [2-(4-ethoxyphenyl)-ethyl]-amide,
[48] [1-(2,6-dichlorobenzyl)-4-methyl-3-p-tolyl-1H-pyrrol-2-yl]-(4-hydroxypiperidin-1-yl)-methanone,
[49] (1,4-dimethyl-3-p-tolyl-1H-pyrrol-2-yl)-[4-(2,4,6-trimethoxybenzyl)-piperazin-1-yl]-methanone,
[50] 1-(4-fluorobenzyl)-3-furan-2-yl-4-methyl-1H-pyrrole-2-carboxylic acid (2-morpholin-4-ylethyl)-amide,
[51] 1-benzyl-3-(4-chlorophenyl)-4-methyl-1H-pyrrole-2-carboxylic acid [2-(4-fluorophenyl)-ethyl]-amide,
[52] [4-(2,5-dimethylphenyl)-piperazin-1-yl]-[3-(4-methoxyphenyl)-1,4-dimethyl-1H-pyrrol-2-yl]-methanone,
[53] 3-(4-methoxyphenyl)-1,4-dimethyl-1H-pyrrole-2-carboxylic acid (3-imidazol-1-ylpropyl)-amide,
[54] 1-(4-fluorobenzyl)-3-(4-methoxyphenyl)-4-methyl-1H-pyrrole-2-carboxylic acid [2-(3-trifluoromethylphenyl)-ethyl]-amide,
[55] [3-(4-chlorophenyl)-1-(2-fluorobenzyl)-4-methyl-1H-pyrrol-2-yl]-[4-(5-methylpyrazin-2-carbonyl)-piperazin-1-yl]-methanone,
[56] 3-(4-chlorophenyl)-1-isobutyl-4-methyl-1H-pyrrole-2-carboxylic acid 3-fluoro-5-trifluoromethylbenzylamide,
[57] [3-(4-chlorophenyl)-1,4-dimethyl-1H-pyrrol-2-yl]-(4-pyridin-4-ylpiperazin-1-yl)-methanone,
[58] 3-(4-chlorophenyl)-1-(2-fluorobenzyl)-4-methyl-1H-pyrrole-2-carboxylic acid (3-imidazol-1-ylpropyl)-amide,
[59] (1,4-dimethyl-3-phenyl-1H-pyrrol-2-yl)-[4-(3-fluoro-4-methoxybenzyl)-piperazin-1-yl]-methanone,
[60] 1-benzyl-3-furan-2-yl-4-methyl-1H-pyrrole-2-carboxylic acid [2-(4-bromophenyl)-ethyl]-amide,
[61] (4-cycloheptylpiperazin-1-yl)-(3-furan-2-yl-1,4-dimethyl-1H-pyrrol-2-yl)-methanone,
[62] 1-benzyl-4-methyl-3-phenyl-1H-pyrrole-2-carboxylic acid [2-(4-methoxyphenoxy)-ethyl]-amide,
[63] 1-(4-fluorobenzyl)-3-furan-2-yl-4-methyl-1H-pyrrole-2-carboxylic acid (3-dimethylamino-propyl)-amide,
[64] [1-(4-fluorobenzyl)-3-(4-methoxyphenyl)-4-methyl-1H-pyrrol-2-yl]-(2-pyrrolidin-1-ylmethylpyrrolidin-1-yl)-methanone,
[65] 3-(4-chlorophenyl)-1-isobutyl-4-methyl-1H-pyrrole-2-carboxylic acid (3-diethylamino-propyl)-amide,
[66] [3-(4-chlorophenyl)-1,4-dimethyl-1H-pyrrol-2-yl]-[4-(2-fluoro-5-methoxybenzyl)-piperazin-1-yl]-methanone,
[67] 3-(4-methoxyphenyl)-1,4-dimethyl-1H-pyrrole-2-carboxylic acid pentylamide,
[68] (1-butyl-4-methyl-3-p-tolyl-1H-pyrrol-2-yl)-[4-(2,5-dimethoxybenzyl)-piperazin-1-yl]-methanone,
[69] [4-(2-diethylamino-ethyl)-piperazin-1-yl]-[4-methyl-1-(4-methylbenzyl)-3-p-tolyl-1H-pyrrol-2-yl]-methanone,
[70] [4-(3-chlorophenyl)-piperazin-1-yl]-[3-(4-methoxyphenyl)-1,4-dimethyl-1H-pyrrol-2-yl]-methanone,
[71] [1-(2-bromobenzyl)-3-(4-chlorophenyl)-4-methyl-1H-pyrrol-2-yl]-(4-isopropylpiperazin-1-yl)-methanone,
[72] [4-(2-dimethylamino-ethyl)-piperazin-1-yl]-[1-(4-fluorobenzyl)-3-(4-methoxyphenyl)-4-methyl-1H-pyrrol-2-yl]-methanone,
[73] 3-(4-chlorophenyl)-1-(2-fluorobenzyl)-4-methyl-1H-pyrrole-2-carboxylic acid 2,4-dimethoxybenzylamide,
[74] 1-benzyl-4-methyl-3-p-tolyl-1H-pyrrole-2-carboxylic acid (2-pyrrolidin-1-ylethyl)-amide,
[75] [1-(4-fluorobenzyl)-3-furan-2-yl-4-methyl-1H-pyrrol-2-yl]-[4-(3-fluoro-4-methoxybenzyl)-piperazin-1-yl]-methanone,
[76] 3-(4-methoxyphenyl)-1,4-dimethyl-1H-pyrrole-2-carboxylic acid 2,4-dimethoxybenzylamide,
[77] 1-benzyl-4-methyl-3-phenyl-1H-pyrrole-2-carboxylic acid (2-pyrrolidin-1-ylethyl)-amide,
[78] 3-(4-chlorophenyl)-1,4-dimethyl-1H-pyrrole-2-carboxylic acid [3-(2-methylpiperidin-1-yl)-propyl]-amide,
[79] 1-(4-fluorobenzyl)-3-furan-2-yl-4-methyl-1H-pyrrole-2-carboxylic acid cyclohexylamide,
[80] 3-furan-2-yl-1,4-dimethyl-1H-pyrrole-2-carboxylic acid 4-fluoro-2-trifluoromethylbenzylamide,
[81] 1-benzyl-3-furan-2-yl-4-methyl-1H-pyrrole-2-carboxylic acid (1-naphthalen-2-ylethyl)-amide,
[82] 3-(4-chlorophenyl)-1-ethyl-4-methyl-1H-pyrrole-2-carboxylic acid (furan-2-ylmethyl)-amide,
[83] 1-benzyl-4-methyl-3-phenyl-1H-pyrrole-2-carboxylic acid (3-dimethylamino-propyl)-methylamide,
[84] [3-(4-methoxyphenyl)-1,4-dimethyl-1H-pyrrol-2-yl]-(4-p-tolylpiperazin-1-yl)-methanone,

[85] 1-(4-methoxybenzyl)-4-methyl-3-p-tolyl-1H-pyrrole-2-carboxylic acid (thiophen-2-ylmethyl)-amide,
[86] 4-methyl-1-(4-methylbenzyl)-3-p-tolyl-1H-pyrrole-2-carboxylic acid phenethylamide,
[87] 1,4-dimethyl-3-p-tolyl-1H-pyrrole-2-carboxylic acid 3,5-difluorobenzylamide,
[88] 3-(4-methoxyphenyl)-1,4-dimethyl-1H-pyrrole-2-carboxylic acid indan-1-ylamide,
[89] 1-benzyl-4-methyl-3-phenyl-1H-pyrrole-2-carboxylic acid 4-dimethylaminobenzylamide,
[90] 1-(4-fluorobenzyl)-3-furan-2-yl-4-methyl-1H-pyrrole-2-carboxylic acid (1-naphthalen-2-ylmethylpyrrolidin-3-yl)-amide,
[91] [3-furan-2-yl-4-methyl-1-(4-trifluoromethylbenzyl)-1H-pyrrol-2-yl]-(4-methyl-[1,4]diazepan-1-yl)-methanone,
[92] [1-(2-bromobenzyl)-3-(4-chlorophenyl)-4-methyl-1H-pyrrol-2-yl]-[4-(3-trifluoromethylphenyl)-piperazin-1-yl]-methanone,
[93] [3-furan-2-yl-1-(4-methoxybenzyl)-4-methyl-1H-pyrrole-2-yl]-(4-thiophen-3-ylmethylpiperazin-1-yl)-methanone,
[94] 1,4-dimethyl-3-p-tolyl-1H-pyrrole-2-carboxylic acid (2-benzyloxy-cyclohexyl)-amide,
[95] 2-{4-[1-benzyl-3-(4-chlorophenyl)-4-methyl-1H-pyrrole-2-carbonyl]-piperazin-1-yl}-N-isopropylacetamide,
[96] (2,6-dimethylmorpholin-4-yl)-[3-(4-methoxyphenyl)-1,4-dimethyl-1H-pyrrol-2-yl]-methanone,
[97] 3-furan-2-yl-1-(4-methoxybenzyl)-4-methyl-1H-pyrrole-2-carboxylic acid (thiophen-2-ylmethyl)-amide,
[98] 1,4-dimethyl-3-p-tolyl-1H-pyrrole-2-carboxylic acid (furan-2-ylmethyl)-amide,
[99] 4-methyl-1-(4-methylbenzyl)-3-p-tolyl-1H-pyrrole-2-carboxylic acid (3-dimethylamino-propyl)-amide,
[100] 1-(4-fluorobenzyl)-3-(4-methoxyphenyl)-4-methyl-1H-pyrrole-2-carboxylic acid (2-oxo-tetrahydro-furan-3-yl)-amide,
[101] 3-(4-chlorophenyl)-1,4-dimethyl-1H-pyrrole-2-carboxylic acid (2-phenoxy-ethyl)-amide,
[102] 3-(4-(1-benzyl-4-methyl-3-p-tolyl-1H-pyrrole-2-carbonyl)piperazin-1-yl)pyrazine-2-carbonitrile
[103] 2-{3-(4-methoxyphenyl)-1,4-dimethyl-1H-pyrrole-2-carbonyl]-amino}-3-phenylpropionic acid methyl ester,
[104] 3-(4-chlorophenyl)-1,4-dimethyl-1H-pyrrole-2-carboxylic acid (2-morpholin-4-ylethyl)-amide,
[105] 3-furan-2-yl-1,4-dimethyl-1H-pyrrole-2-carboxylic acid indan-2-ylamide,
[106] (1-butyl-4-methyl-3-p-tolyl-1H-pyrrol-2-yl)-[4-(2-fluorophenyl)-piperazin-1-yl]-methanone,
[107] [4-(3-chlorophenyl)-piperazin-1-yl]-(1,4-dimethyl-3-p-tolyl-1H-pyrrol-2-yl)-methanone,
[108] [1-(4-fluorobenzyl)-3-furan-2-yl-4-methyl-1H-pyrrol-2-yl]-(4-naphthalen-2-ylmethylpiperazin-1-yl)-methanone,
[109] 3-(4-chlorophenyl)-1-isobutyl-4-methyl-1H-pyrrole-2-carboxylic acid p-tolylamide,
[110] (1-benzyl-4-methyl-3-p-tolyl-1H-pyrrol-2-yl)-[4-(2-hydroxy-ethyl)-piperazin-1-yl]-methanone,
[111] 1-butyl-4-methyl-3-p-tolyl-1H-pyrrole-2-carboxylic acid [2-(2,5-dimethoxyphenyl)-ethyl]-amide,
[112] 1-butyl-4-methyl-3-p-tolyl-1H-pyrrole-2-carboxylic acid (3-imidazol-1-ylpropyl)-amide,
[113] 1-benzyl-3-(4-chlorophenyl)-4-methyl-1H-pyrrole-2-carboxylic acid [2-(3,4-dimethoxyphenyl)-ethyl]-methylamide,
[114] 4-methyl-1-(4-methylbenzyl)-3-p-tolyl-1H-pyrrole-2-carboxylic acid (3-morpholin-4-ylpropyl)-amide,
[115] 4-methyl-1-(4-methylbenzyl)-3-p-tolyl-1H-pyrrole-2-carboxylic acid 4-fluoro-2-trifluoromethylbenzylamide,
[116] 2-{[1-benzyl-3-(4-chlorophenyl)-4-methyl-1H-pyrrole-2-carbonyl]-amino}-3-(4-chlorophenyl)-propionic acid ethyl ester,
[117] 1-benzyl-4-methyl-3-phenyl-1H-pyrrole-2-carboxylic acid 3-fluoro-4-trifluoromethylbenzylamide,
[118] 1-(4-bromobenzyl)-4-methyl-3-p-tolyl-1H-pyrrole-2-carboxylic acid (2-pyridin-2-ylethyl)-amide,
[119] 1-(4-fluorobenzyl)-3-furan-2-yl-4-methyl-1H-pyrrole-2-carboxylic acid benzyl-(2-hydroxy-ethyl)-amide,
[120] 2-[4-(1-butyl-4-methyl-3-p-tolyl-1H-pyrrole-2-carbonyl)-piperazin-1-yl]-N-methyl-N-phenylacetamide,
[121] [4-methyl-1-(4-methylbenzyl)-3-p-tolyl-1H-pyrrol-2-yl]-(4-phenylpiperazin-1-yl)-methanone,
[122] 1-benzyl-4-methyl-3-p-tolyl-1H-pyrrole-2-carboxylic acid (1-benzylpyrrolidin-3-yl)-amide,
[123] [1-(4-fluorobenzyl)-3-furan-2-yl-4-methyl-1H-pyrrol-2-yl]-[4-(3-trifluoromethylphenyl)-piperazin-1-yl]-methanone,
[124] 1-(4-methoxybenzyl)-4-methyl-3-p-tolyl-1H-pyrrole-2-carboxylic acid butylamide,
[125] 1-benzyl-4-methyl-3-p-tolyl-1H-pyrrole-2-carboxylic acid [2-(2-fluorophenyl)-ethyl]-amide,
[126] 4-methyl-1-(4-methylbenzyl)-3-p-tolyl-1H-pyrrole-2-carboxylic acid 3,4-dimethoxybenzylamide,
[127] 3-(4-chlorophenyl)-1-isobutyl-4-methyl-1H-pyrrole-2-carboxylic acid (2-diethylamino-ethyl)-amide,
[128] 1-{4-[3-(4-chlorophenyl)-1-ethyl-4-methyl-1H-pyrrole-2-carbonyl]-piperazin-1-yl}-2-phenylethanone,
[129] 1-(4-fluorobenzyl)-4-methyl-3-p-tolyl-1H-pyrrole-2-carboxylic acid 3-trifluoromethoxybenzylamide,
[130] [1-benzyl-3-(4-chlorophenyl)-4-methyl-1H-pyrrol-2-yl]-(3-methylpiperidin-1-yl)-methanone,
[131] 1-(4-fluorobenzyl)-4-methyl-3-p-tolyl-1H-pyrrole-2-carboxylic acid (2-p-tolylethyl)-amide,
[132] 1-(4-methoxybenzyl)-4-methyl-3-p-tolyl-1H-pyrrole-2-carboxylic acid [2-(2-methyl-5-nitro-imidazol-1-yl)-ethyl]-amide,
[133] 1,4-dimethyl-3-p-tolyl-1H-pyrrole-2-carboxylic acid 2,3-dimethoxybenzylamide,
[134] 1-(2-bromobenzyl)-3-(4-chlorophenyl)-4-methyl-1H-pyrrole-2-carboxylic acid [2-(ethyl-m-tolylamino)-ethyl]-amide,
[135] 1-(4-fluorobenzyl)-3-furan-2-yl-4-methyl-1H-pyrrole-2-carboxylic acid (4-isopropylphenyl)-amide,
[136] 5-chloro-2-methoxybenzoic acid N'-[1-(4-fluorobenzyl)-3-(4-methoxyphenyl)-4-methyl-1H-pyrrole-2-carbonyl]-hydrazide,
[137] (1-benzyl-4-methyl-3-p-tolyl-1H-pyrrol-2-yl)-[1,4']bipiperidinyl-1'-ylmethanone,
[138] 3-furan-2-yl-1,4-dimethyl-1H-pyrrole-2-carboxylic acid (4-butylphenyl)-amide,
[139] 1-benzyl-4-methyl-3-phenyl-1H-pyrrole-2-carboxylic acid [2-(1H-indol-3-yl)-ethyl]-amide,
[140] [4-(4-tert-butylbenzyl)-piperazin-1-yl]-[1-(4-fluorobenzyl)-4-methyl-3-p-tolyl-1H-pyrrol-2-yl]-methanone,
[141] [1-(4-fluorobenzyl)-4-methyl-3-p-tolyl-1H-pyrrol-2-yl]-morpholin-4-ylmethanone,
[142] 3-[(1-benzyl-3-furan-2-yl-4-methyl-1H-pyrrole-2-carbonyl)-amino]-propionic acid ethyl ester,
[143] 1,4-dimethyl-3-phenyl-1H-pyrrole-2-carboxylic acid (naphthalen-2-ylcarbamoylmethyl)-amide,
[144] [3-(4-chlorophenyl)-1,4-dimethyl-1H-pyrrol-2-yl]-[4-(2-ethoxyphenyl)-piperazin-1-yl]-methanone,

[145] 1-(4-fluorobenzyl)-3-furan-2-yl-4-methyl-1H-pyrrole-2-carboxylic acid (4-cyanomethylphenyl)-amide,
[146] 4-[1-benzyl-3-(4-chlorophenyl)-4-methyl-1H-pyrrole-2-carbonyl]-piperazine-1-carboxylic acid tert.-butyl ester,
[147] (1,4-dioxa-8-aza-spiro[4.5]dec-8-yl)-[1-(4-fluorobenzyl)-3-furan-2-yl-4-methyl-1H-pyrrol-2-yl]-methanone,
[148] 3-furan-2-yl-4-methyl-1-(4-trifluoromethylbenzyl)-1H-pyrrole-2-carboxylic acid pentylamide,
[149] 3-furan-2-yl-1-(4-methoxybenzyl)-4-methyl-1H-pyrrole-2-carboxylic acid [3-(methylphenylamino)-propyl]-amide,
[150] 1-(2,6-dichlorobenzyl)-4-methyl-3-p-tolyl-1H-pyrrole-2-carboxylic acid (2-azepan-1-ylethyl)-amide,
[151] 1-(4-bromobenzyl)-4-methyl-3-p-tolyl-1H-pyrrole-2-carboxylic acid cyclopentylamide,
[152] [1-(2,6-dichlorobenzyl)-4-methyl-3-p-tolyl-1H-pyrrol-2-yl]-[4-(2,4-dimethoxyphenyl)-piperazin-1-yl]-methanone,
[153] 3-(4-chlorophenyl)-1-(2-fluorobenzyl)-4-methyl-1H-pyrrole-2-carboxylic acid [2-(2-chlorophenoxy)-ethyl]-amide,
[154] 1-(2,6-dichlorobenzyl)-4-methyl-3-p-tolyl-1H-pyrrole-2-carboxylic acid (3,3-dimethylbutyl)-amide,
[155] 1,4-dimethyl-3-p-tolyl-1H-pyrrole-2-carboxylic acid (2-benzyloxy-cyclohexyl)-amide,
[156] [4-methyl-1-(4-methylbenzyl)-3-p-tolyl-1H-pyrrol-2-yl]-thiomorpholin-4-ylmethanone,
[157] 3-(4-chlorophenyl)-1-isobutyl-4-methyl-1H-pyrrole-2-carboxylic acid (3-dimethylamino-propyl)-methylamide,
[158] [4-(2,5-dimethylphenyl)-piperazin-1-yl]-[3-furan-2-yl-1-(4-methoxybenzyl)-4-methyl-1H-pyrrol-2-yl]-methanone,
[159] 5-chloro-2-methoxybenzoic acid N'-[3-(4-methoxyphenyl)-1,4-dimethyl-1H-pyrrole-2-carbonyl]-hydrazide,
[160] 2-(3,4-difluorophenyl)-1-{4-[1-(4-fluorobenzyl)-3-furan-2-yl-4-methyl-1H-pyrrole-2-carbonyl]-piperazin-1-yl}-ethanone,
[161] 2-{4-[1-(4-fluorobenzyl)-3-furan-2-yl-4-methyl-1H-pyrrole-2-carbonyl]-piperazin-1-yl}-N-isopropylacetamide,
[162] 3-furan-2-yl-4-methyl-1-(4-trifluoromethylbenzyl)-1H-pyrrole-2-carboxylic acid [1-(3-methoxyphenyl)-ethyl]-amide,
[163] 2-[(1-benzyl-3-furan-2-yl-4-methyl-1H-pyrrole-2-carbonyl)-amino]-3-(4-chlorophenyl)-propionic acid methyl ester,
[164] [3-furan-2-yl-1-(4-methoxybenzyl)-4-methyl-1H-pyrrol-2-yl]-(4-methylpiperazin-1-yl)-methanone,
[165] 1,4-dimethyl-3-phenyl-1H-pyrrole-2-carboxylic acid (1-benzylpyrrolidin-3-yl)-amide,
[166] (1,4-dimethyl-3-p-tolyl-1H-pyrrol-2-yl)-(4-thieno[2,3-d]pyrimidin-4-ylpiperazin-1-yl)-methanone,
[167] 4-methyl-1-(4-methylbenzyl)-3-p-tolyl-1H-pyrrole-2-carboxylic acid (3-methoxy-propyl)-amide,
[168] [3-(4-methoxyphenyl)-1,4-dimethyl-1H-pyrrol-2-yl]-[4-(5-trifluoromethylpyridin-2-yl)-piperazin-1-yl]-methanone,
[169] 1-(4-bromobenzyl)-4-methyl-3-p-tolyl-1H-pyrrole-2-carboxylic acid (3-morpholin-4-ylpropyl)-amide,
[170] 1,4-dimethyl-3-p-tolyl-1H-pyrrole-2-carboxylic acid [2-(2,3-dimethylphenyl)-ethyl]-amide,
[171] [1-(4-methoxybenzyl)-4-methyl-3-p-tolyl-1H-pyrrol-2-yl]-(3-methyl-4-p-tolylpiperazin-1-yl)-methanone,
[172] [3-(4-chlorophenyl)-1-ethyl-4-methyl-1H-pyrrol-2-yl]-[4-(2,4-dimethoxyphenyl)-piperazin-1-yl]-methanone,
[173] 2-{4-[1-(2-bromobenzyl)-3-(4-chlorophenyl)-4-methyl-1H-pyrrole-2-carbonyl]-piperazin-1-yl}-benzonitrile,
[174] 1-(4-bromobenzyl)-4-methyl-3-p-tolyl-1H-pyrrole-2-carboxylic acid (1-ethylpyrrolidin-2-ylmethyl)-amide,
[175] 3-(4-chlorophenyl)-1-isobutyl-4-methyl-1H-pyrrole-2-carboxylic acid [2-(2-chlorophenoxy)-ethyl]-amide,
[176] 3-(4-chlorophenyl)-1,4-dimethyl-1H-pyrrole-2-carboxylic acid [2-(1H-indol-3-yl)-ethyl]-amide,
[177] 1-(4-fluorobenzyl)-4-methyl-3-p-tolyl-1H-pyrrole-2-carboxylic acid (naphthalen-2-ylcarbamoylmethyl)-amide,
[178] 4-(1-benzyl-3-furan-2-yl-4-methyl-1H-pyrrole-2-carbonyl)-piperazine-1-carboxylic acid benzyl ester,
[179] 1,4-dimethyl-3-phenyl-1H-pyrrole-2-carboxylic acid (1-benzylpyrrolidin-3-yl)-amide,
[180] [3-(4-chlorophenyl)-1-(2-fluorobenzyl)-4-methyl-1H-pyrrol-2-yl]-[4-(4-trifluoromethylphenyl)-piperazin-1-yl]-methanone,
[181] [3-(4-chlorophenyl)-1-isobutyl-4-methyl-1H-pyrrol-2-yl]-(4-phenylpiperazin-1-yl)-methanone,
[182] 2-{4-[1-butyl-3-(4-chlorophenyl)-4-methyl-1H-pyrrole-2-carbonyl]-piperazin-1-yl}-1-pyrrolidin-1-ylethanone,
[183] [1-benzyl-3-(4-chlorophenyl)-4-methyl-1H-pyrrol-2-yl]-[4-(2-chloro-4-fluorobenzoyl)-piperazin-1-yl]-methanone,
[184] (4-benzoylpiperidin-1-yl)-[1-(4-methoxybenzyl)-4-methyl-3-p-tolyl-1H-pyrrol-2-yl]-methanone,
[185] 3-furan-2-yl-1,4-dimethyl-1H-pyrrole-2-carboxylic acid ethylpyridin-4-ylmethylamide,
[186] 1-(4-bromobenzyl)-4-methyl-3-p-tolyl-1H-pyrrole-2-carboxylic acid (2-pyrrolidin-1-ylethyl)-amide,
[187] [3-(4-chlorophenyl)-1-isobutyl-4-methyl-1H-pyrrol-2-yl]-[4-(4-methylbenzoyl)-piperazin-1-yl]-methanone,
[188] [1-benzyl-3-(4-chlorophenyl)-4-methyl-1H-pyrrol-2-yl]-(4-thieno[2,3-d]pyrimidin-4-ylpiperazin-1-yl)-methanone,
[189] 1-(1,4-dimethyl-3-phenyl-1H-pyrrole-2-carbonyl)-hydroxypiperidine-3-carboxylic acid ethyl ester,
[190] 1,4-dimethyl-3-phenyl-1H-pyrrole-2-carboxylic acid (1-phenylethyl)-amide,
[191] [3-furan-2-yl-1-(4-methoxybenzyl)-4-methyl-1H-pyrrol-2-yl]-(1,3,4,9-tetrahydro-b-carbolin-2-yl)-methanone,
[192] 1-{4-[1-benzyl-3-(4-chlorophenyl)-4-methyl-1H-pyrrole-2-carbonyl]-piperazin-1-yl}-2-(3,4-difluorophenyl)-ethanone,
[193] [1-(4-bromobenzyl)-4-methyl-3-p-tolyl-1H-pyrrol-2-yl]-[4-(3-phenylpropyl)-piperazin-1-yl]-methanone,
[194] 1-(2-bromobenzyl)-3-(4-chlorophenyl)-4-methyl-1H-pyrrole-2-carboxylic acid [2-(1H-indol-3-yl)-ethyl]-methylamide,
[195] 1-(4-{4-[1-(4-bromobenzyl)-4-methyl-3-p-tolyl-1H-pyrrole-2-carbonyl]-piperazin-1-yl}-phenyl)-ethanone,
[196] 1,4-dimethyl-3-phenyl-1H-pyrrole-2-carboxylic acid 4-fluoro-2-trifluoromethylbenzylamide,
[197] 4-methyl-1-(4-methylbenzyl)-3-p-tolyl-1H-pyrrole-2-carboxylic acid (4-phenoxyphenyl)-amide,
[198] (4-hydroxy-piperidin-1-yl)-[1-(4-methoxybenzyl)-4-methyl-3-p-tolyl-1H-pyrrol-2-yl]-methanone,
[199] 4-diethylaminobenzoic acid N'-(1-benzyl-4-methyl-3-p-tolyl-1H-pyrrole-2-carbonyl)-hydrazide,
[200] [3-(4-chlorophenyl)-1-isobutyl-4-methyl-1H-pyrrol-2-yl]-[4-(3-chlorophenyl)-piperazin-1-yl]-methanone,

[201] 1-(4-bromobenzyl)-4-methyl-3-p-tolyl-1H-pyrrole-2-carboxylic acid [2-(3,4-dichlorophenyl)-ethyl]-amide,
[202] 3-(4-chlorophenyl)-1-ethyl-4-methyl-1H-pyrrole-2-carboxylic acid [2-(1H-indol-3-yl)-ethyl]-amide,
[203] [1-(4-fluorobenzyl)-4-methyl-3-p-tolyl-1H-pyrrol-2-yl]-[4-(5-trifluoromethylpyridin-2-yl)-piperazin-1-yl]-methanone,
[204] 1,4-dimethyl-3-phenyl-1H-pyrrole-2-carboxylic acid 3-trifluoromethoxybenzylamide,
[205] [1-(4-fluorobenzyl)-4-methyl-3-p-tolyl-1H-pyrrol-2-yl]-[4-(4-methylbenzoyl)-piperazin-1-yl]-methanone,
[206] [4-(3,4-dichlorophenyl)-piperazin-1-yl]-[1-(4-fluorobenzyl)-4-methyl-3-p-tolyl-1H-pyrrol-2-yl]-methanone,
[207] 3-(4-chlorophenyl)-1-ethyl-4-methyl-1H-pyrrole-2-carboxylic acid 2,6-dimethoxybenzylamide,
[208] 4-methyl-1-(4-methylbenzyl)-3-p-tolyl-1H-pyrrole-2-carboxylic acid [2-(3,4-dimethoxyphenyl)-ethyl]-amide,
[209] 1-{4-[3-(4-chlorophenyl)-1-isobutyl-4-methyl-1H-pyrrole-2-carbonyl]-piperazin-1-yl}-2-(3,4-difluorophenyl)-ethanone,
[210] [1-(4-fluorobenzyl)-4-methyl-3-p-tolyl-1H-pyrrol-2-yl]-[4-(2-methoxyphenyl)-piperidin-1-yl]-methanone,
[211] [3-furan-2-yl-4-methyl-1-(4-trifluoromethylbenzyl)-1H-pyrrol-2-yl]-thiomorpholin-4-ylmethanone,
[212] 1,4-dimethyl-3-phenyl-1H-pyrrole-2-carboxylic acid (2-thiophen-2-ylethyl)-amide,
[213] 4-diethylaminobenzoic acid N'-(1-butyl-4-methyl-3-p-tolyl-1H-pyrrole-2-carbonyl)-hydrazide,
[214] {1-[1-(4-fluorobenzyl)-3-(4-methoxyphenyl)-4-methyl-1H-pyrrole-2-carbonyl]-pyrrolidin-3-yl}-carbamic acid tert.-butyl ester,
[215] 2-{4-[3-(4-chlorophenyl)-1-isobutyl-4-methyl-1H-pyrrole-2-carbonyl]-piperazin-1-yl}-1-pyrrolidin-1-ylethanone,
[216] [4-(2,3-dihydrobenzo[1,4]dioxine-2-carbonyl)-piperazin-1-yl]-(1,4-dimethyl-3-phenyl-1H-pyrrol-2-yl)-methanone,
[217] 3-furan-2-yl-1,4-dimethyl-1H-pyrrole-2-carboxylic acid 3,4-dimethoxybenzylamide,
[218] [3-furan-2-yl-4-methyl-1-(4-trifluoromethylbenzyl)-1H-pyrrol-2-yl]-(4-pyridin-2-ylpiperazin-1-yl)-methanone,
[219] [4-(furan-2-carbonyl)-piperazin-1-yl]-[3-furan-2-yl-4-methyl-1-(4-trifluoromethylbenzyl)-1H-pyrrol-2-yl]-methanone,
[220] 3-furan-2-yl-4-methyl-1-(4-trifluoromethylbenzyl)-1H-pyrrole-2-carboxylic acid (4-tert.-butylphenyl)-amide,
[221] 2-{4-[3-(4-chlorophenyl)-1-isobutyl-4-methyl-1H-pyrrole-2-carbonyl]-piperazin-1-yl}-benzonitrile,
[222] (3-furan-2-yl-1,4-dimethyl-1H-pyrrol-2-yl)-[4-(4-trifluoromethylpyridin-2-yl)-piperazin-1-yl]-methanone,
[223] 1,4-dimethyl-3-phenyl-1H-pyrrole-2-carboxylic acid 3,5-difluorobenzylamide,
[224] 1,4-dimethyl-3-phenyl-1H-pyrrole-2-carboxylic acid (pyridin-4-ylmethyl)-amide,
[225] 2-[4-(3-furan-2-yl-1,4-dimethyl-1H-pyrrole-2-carbonyl)-piperazin-1-yl]-benzonitrile,
[226] 3-furan-2-yl-1,4-dimethyl-1H-pyrrole-2-carboxylic acid methyl-(2-pyridin-2-ylethyl)-amide,
[227] 3-furan-2-yl-1,4-dimethyl-1H-pyrrole-2-carboxylic acid (3-methoxybenzyl)-(tetrahydro-furan-2-ylmethyl)-amide,
[228] 3-furan-2-yl-1,4-dimethyl-1H-pyrrole-2-carboxylic acid (4-phenoxyphenyl)-amide,
[229] 3-furan-2-yl-1,4-dimethyl-1H-pyrrole-2-carboxylic acid pentylamide,
[230] 2-(3,4-difluorophenyl)-1-[4-(3-furan-2-yl-1,4-dimethyl-1H-pyrrole-2-carbonyl)-piperazin-1-yl]-ethanone,
[231] 3-furan-2-yl-1,4-dimethyl-1H-pyrrole-2-carboxylic acid phenylamide,
[232] [4-(2,4-dimethoxyphenyl)-piperazin-1-yl]-(3-furan-2-yl-1,4-dimethyl-1H-pyrrol-2-yl)-methanone,
[233] 3-furan-2-yl-1,4-dimethyl-1H-pyrrole-2-carboxylic acid [2-(3,4-dichlorophenyl)-ethyl]-amide,
[234] 3-furan-2-yl-1,4-dimethyl-1H-pyrrole-2-carboxylic acid [2-(2-chlorophenoxy)-ethyl]-amide,
[235] 3-furan-2-yl-1,4-dimethyl-1H-pyrrole-2-carboxylic acid 3-methoxybenzylamide,
[236] 3-furan-2-yl-4-methyl-1-(4-trifluoromethylbenzyl)-1H-pyrrole-2-carboxylic acid phenethylamide,
[237] 3-furan-2-yl-1,4-dimethyl-1H-pyrrole-2-carboxylic acid cyclopentylamide,
[238] 3-furan-2-yl-1,4-dimethyl-1H-pyrrole-2-carboxylic acid (pyridin-2-ylmethyl)-amide,
[239] 3-furan-2-yl-4-methyl-1-(4-trifluoromethylbenzyl)-1H-pyrrole-2-carboxylic acid [2-(3,4-dimethoxyphenyl)-ethyl]-amide,
[240] [1-(4-bromobenzyl)-4-methyl-3-p-tolyl-1H-pyrrol-2-yl]-(2,6-dimethylmorpholin-4-yl)-methanone,
[241] 1,4-dimethyl-3-phenyl-1H-pyrrole-2-carboxylic acid (2-p-tolylethyl)-amide,
[242] (1,4-dimethyl-3-phenyl-1H-pyrrol-2-yl)-[4-(4-fluorophenyl)-piperazin-1-yl]-methanone, and
[243] 4-methyl-1-(4-methylbenzyl)-3-p-tolyl-1H-pyrrole-2-carboxylic acid [2-(1H-indol-3-yl)-ethyl]-methylamide, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention also provides a method for preparing 1,3-disubstituted 4-methyl-1H-pyrrole-2-carboxamides of the aforementioned formula I, in which a compound corresponding to formula II,

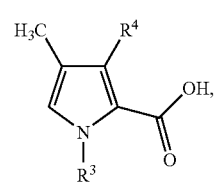

II in which $R^3$ and $R^4$ have the above-stated meanings, is converted, optionally in at least one reaction medium, preferably in at least one reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one suitable coupling agent, preferably in the presence of at least one coupling agent selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisopropylcarbodiimide, 1,1'-carbonyldiimidazole (CDI), N-[(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU) and 1-hydroxy-7-azabenzotriazole (HOAt), optionally in the presence of at least one base, preferably in the presence of at least one base selected from the group consisting of triethylamine, pyridine, dimethylaminopyridine, N-methylmorpholine and diisopropylethylamine, preferably at a temperature of −70° C. to 100° C., by reaction with at least one compound corresponding to formula $HNR^1R^2$, in which $R^1$ and $R^2$ have the above-stated meaning, into a corresponding compound corresponding to formula I, optionally in the form of a corresponding salt,

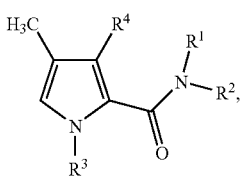

I in which $R^1$, $R^2$, $R^3$ and $R^4$ have the above-stated meaning, and this is optionally purified and/or isolated.

Compounds corresponding to formula II may be obtained as described in the following Scheme 1.

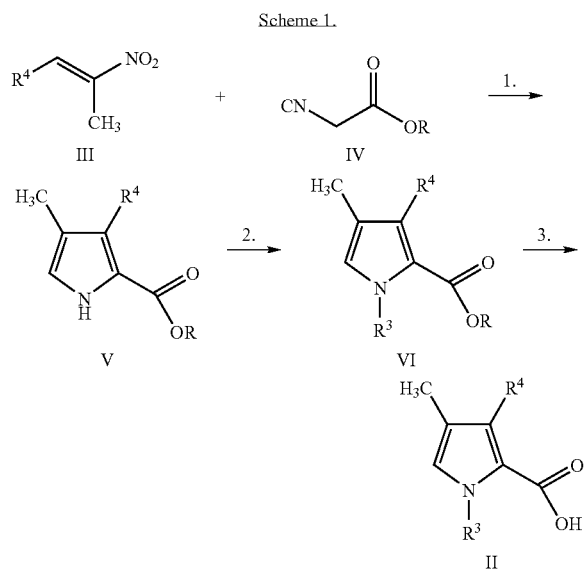

Scheme 1.

In stage 1, at least one compound corresponding to formula II, in which $R^4$ has the above-stated meaning, is reacted in at least one organic solvent, preferably in at least one organic solvent selected from the group consisting of ethanol, isopropanol, tetrahydrofuran and corresponding mixtures, in the presence of at least one base, preferably in the presence of at least one guanidine base, particularly preferably in the presence of 1,5,7-triazabicyclo[4.4.0]dec-5-ene, which may optionally be polymer-bound, with at least one compound corresponding to formula IV, in which R may denote a linear or branched $C_{1-10}$ alkyl residue or a benzyl residue, to yield at least one compound corresponding to formula V, in which R and $R^4$ have the above-stated meaning, and these are optionally purified and/or isolated.

In stage 2, at least one compound corresponding to formula V is reacted in at least one organic solvent, preferably in at least one organic solvent selected from the group consisting of diethyl ether, di-isopropyl ether, tetrahydrofuran and corresponding mixtures, in the presence of at least one base, preferably in the presence of at least one base selected from the group consisting of diisopropylethylamine, triethylamine, pyridine, diethylamine, diisopropylamine, butyllithium, lithium diisopropylamide, sodium hydride, potassium hydride, lithium aluminium hydride and sodium borohydride, with at least one compound corresponding to formula $R^3$-LG, in which $R^3$ has the above-stated meaning and LG denotes a leaving group, preferably denotes a halogen atom, particularly preferably chlorine or bromine, to yield at least one compound corresponding to formula VI, in which $R^3$, $R^4$ and R have the above-stated meaning, and these are optionally purified and/or isolated.

In stage 3, at least one compound corresponding to formula VI is reacted in at least one solvent, preferably in at least one solvent selected from the group consisting of ethanol, dichloromethane, methanol, acetonitrile, tetrahydrofuran, water and corresponding mixtures, is reacted in the presence of at least one acid, preferably in the presence of at least one acid selected from the group consisting of sulfuric acid, hydrochloric acid and Lewis acids or in the presence of at least one base, preferably in the presence of at least one base selected from the group consisting of potassium hydroxide, lithium hydroxide, sodium hydroxide, sodium carbonate and potassium carbonate, to yield at least one compound corresponding to formula II, in which $R^3$ and $R^4$ have the above-stated meaning, and these are optionally purified and isolated.

The 1,3-disubstituted 4-methyl-1H-pyrrole-2-carboxamides according to the invention of the above-stated general formula I and optionally corresponding stereoisomers and in each case the corresponding salts and solvates are toxicologically safe and are therefore suitable as pharmaceutical active ingredients in pharmaceutical preparations. The present invention accordingly also provides a pharmaceutical composition containing at least one 1,3-disubstituted 4-methyl-1H-pyrrole-2-carboxamide compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The pharmaceutical composition according to the invention is suitable for noradrenalin receptor regulation, in particular for inhibiting noradrenalin reuptake (noradrenalin uptake) and/or for 5-HT receptor regulation, in particular for inhibiting 5-hydroxy-tryptophan reuptake (5-HT uptake) and/or opioid receptor regulation and/or for batrachotoxin (BTX) receptor regulation.

The pharmaceutical composition according to the invention is preferably suitable for the treatment and/or inhibition of disorders and/or diseases which are mediated at least in part by noradrenalin receptors and/or 5-HT receptors, and/or opioid receptors and/or batrachotoxin (BTX) receptors.

The pharmaceutical composition according to the invention also is preferably suitable for the treatment and/or inhibition of pain, especially of pain selected from the group consisting of acute pain, chronic pain and neuropathic pain; for the treatment and/or inhibition of migraine; depression; urinary incontinence; coughing; neurodegenerative diseases, preferably selected from the group consisting of Parkinson's disease, Huntington's chorea, Alzheimer's disease and multiple sclerosis; disorders of food intake, preferably selected from the group consisting of bulimia, anorexia, obesity and cachexia; cognitive dysfunction, preferably memory disorders; epilepsy; diarrhea; pruritus; abuse of alcohol and/or drugs and/or medicines; alcohol and/or drug dependency and/or dependency on medicines, preferably for the prevention and/or reduction of withdrawal symptoms associated with alcohol and/or drug dependency and/or dependency on medicines; for the prevention and/or reduction of the development of tolerance to medicines, in particular medicines based on opioids; for regulating food intake; for modulating locomotor activity; for regulating the cardiovascular system; for local anaesthesia; for anxiolysis; for increasing vigilance; for increasing libido; for diuresis, and/or for antinatriuresis.

The pharmaceutical composition according to the invention is very particularly preferably suitable for the treatment and/or inhibition of pain, preferably acute pain, chronic pain or neuropathic pain.

The present invention also provides the use of at least one substituted 1,3-disubstituted 4-methyl-1H-pyrrole-2-carboxamide compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for noradrenalin receptor regulation, in particular for inhibiting noradrenalin reuptake (noradrenalin uptake) and/or for 5-HT receptor regulation, in particular for inhibiting 5-hydroxytryptophan reuptake (5-HT uptake) and/or for opioid receptor regulation and/or for batrachotoxin (BTX) receptor regulation.

It is preferred to use at least one 1,3-disubstituted 4-methyl-1H-pyrrole-2-carboxamide compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the manufacture of a medicament for the treatment and/or inhibition of disorders and/or diseases which are at least partially mediated by noradrenalin receptors, 5-HT receptors, opioid receptors and/or batrachotoxin (BTX) receptors.

It is particularly preferred to use at least one 1,3-disubstituted 4-methyl-1H-pyrrole-2-carboxamide compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the manufacture of a medicament for the treatment and/or inhibition of pain, preferably of pain selected from the group consisting of acute pain, chronic pain and neuropathic pain; for the treatment and/or inhibition of migraine; depression; urinary incontinence; coughing; neurodegenerative diseases, preferably selected from the group consisting of Parkinson's disease, Huntington's chorea, Alzheimer's disease and multiple sclerosis; disorders of food intake, preferably selected from the group consisting of bulimia, anorexia, obesity and cachexia; cognitive dysfunction, preferably memory disorders; epilepsy; diarrhea; pruritus; abuse of alcohol and/or drugs and/or medicines; alcohol and/or drug dependency and/or dependency on medicines, preferably for the prevention and/or reduction of withdrawal symptoms associated with alcohol and/or drug dependency and/or dependency on medicines; for the prevention and/or reduction of the development of tolerance to medicines, in particular medicines based on opioids; for regulating food intake; for modulating locomotor activity; for regulating the cardiovascular system; for local anaesthesia; for anxiolysis; for increasing vigilance; for increasing libido; for diuresis, and/or for antinatriuresis.

It is very particularly preferred to use at least one 1,3-disubstituted 4-methyl-1H-pyrrole-2-carboxamide compound of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the manufacture of a medicament for the treatment and/or inhibition of pain, preferably of acute pain, chronic pain or neuropathic pain.

The pharmaceutical composition according to the invention is suitable for administration to adults and children including small children and babies.

The pharmaceutical composition according to the invention may be formulated as a liquid, semisolid or solid dosage form, for example in the form of solutions for injection, drops, juices, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted 4-methyl-1H-pyrrole-2-carboxamide compound according to the invention of the above-stated general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the medicament according to the invention conventionally contains further physiologically acceptable pharmaceutical auxiliary substances, which may preferably be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the medicament is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, juices and syrups are preferred for oral administration, while solutions, suspensions, readily reconstitutible dried preparations and sprays are preferred for parenteral, topical and inhalatory administration.

The 1,3-disubstituted 4-methyl-1H-pyrrole-2-carboxamide compounds according to the invention used in the medicament according to the invention in a depot in dissolved form or in a dressing, optionally with the addition of skin penetration promoters, are suitable percutaneous administration preparations. Orally or percutaneously administrable formulations may also release the particular 1,3-disubstituted 4-methyl-1H-pyrrole-2-carboxamide compounds in delayed manner.

The pharmaceutical preparations according to the invention can be produced using conventional means, devices, methods and processes known in the art, such as are described for example in "Remington's Pharmaceutical Sciences", ed. A. R. Gennaro, 17th ed., Mack Publishing Company, Easton, Pa. (1985), in particular in part 8, chapters 76 to 93.

The quantity of the particular 1,3-disubstituted 4-methyl-1H-pyrrole-2-carboxamide compound to be administered to the patient may vary and depends, for example, on the weight or age of the patient and on the mode of administration, the indication and the severity of the complaint. Conventionally, 0.005 to 5000 mg/kg, preferably 0.05 to 500 mg/kg, particularly preferably 0.05 to 50 mg/kg of patient body weight of at least one such compound are administered.

Pharmacological Methods

I. Method for Determining Noradrenalin and 5-HT Uptake Inhibition:

Synaptosomes from rat brain regions were freshly isolated for in vitro studies, as described in the publication "The isolation of nerve endings from brain" by E. G. Gray and V. P. Whittaker, J. Anatomy 96, pages 79-88, 1962. The corresponding literature description is hereby introduced as a reference and is deemed to be part of the disclosure.

The tissue (hypothalamus for the determination of noradrenalin uptake inhibition and medulla and pons for the determination of 5-HT uptake inhibition) was homogenized in ice-cooled 0.32 M sucrose (100 mg of tissue/1 mL) in a glass homogenizer with Teflon pestle using five complete up and down strokes at 840 revolutions/minute. The homogenate was centrifuged at 4° C. for 10 minutes at 1000 g. After subsequent centrifugation at 17000 g for 55 minutes, the synaptosomes ($P_2$ fraction) were obtained, which were resuspended in 0.32 M glucose (0.5 mL/100 mg of original weight). The particular uptake was measured in a 96-well microtitre plate. The volume was 250 µl and incubation proceeded at room temperature (approx. 20-25° C.) under an $O_2$ atmosphere. The incubation time was 7.5 minutes for [$^3$H]-NA and 5 minutes for [$^3$H]-5-HT. The 96 samples were then filtered through a Unifilter GF/B® microtitre plate (Packard) and washed with 200 mL of incubated buffer using a "Brabdel MPXRI-96T Cell-Harvester". The Unifilter GF/B plate was dried for 1 hour at 55° C. The plate was then sealed with a Back Seal® (Packard) and 35 µl of scintillation fluid were added per well (Ultima Gold®, Packard). After sealing with a top Seal® (Packard) and establishing an equilibrium (around 5 hours), radioactivity was determined in a "Trilux 1450 Microbeta" (Wallac).

The following characteristics were determined for the NA transporter:

NA uptake:Km=0.32±0.11 µM

The quantity of protein used in the above determination corresponded to the values known from the literature, as for example described in "Protein measurement with the folin phenol reagent", Lowry et al., J. Biol. Chem., 193, 265-275, 1951.

A detailed description of the method may additionally be found in the literature, for example in M. Ch. Frink, H.-H. Hennies, W. Engelberger, M. Haurand and B. Wilffert (1996) Arzneim.-Forsch./Drug Res. 46 (III), 11, 1029-1036.

II. Method for Determining Affinity for the Batrachotoxin (BTX) Binding Site of the Sodium Channel:

Binding site 2 of the sodium channel is the so-called batrachotoxin (BTX) binding site. [$^3$H]-Batrachotoxinin A20α benzoate (10 nM in the batch) is used as ligand. The ion channel particles (synaptosomes) are enriched from rat cerebrocortex, as described in the publication by Gray and Whittaker (E. G. Gray and V. P. Whittaker (1962) J. Anat. 76, 79-88. The corresponding description is hereby introduced as a reference and is deemed to be part of the present disclosure. The radioactivity measured in the presence of veratridine ($3 \times 10^{-4}$ M in the batch) is defined as non-specific binding.

The assay conditions are as published by Pauwels, Leysen and Laduron, as described in Eur. J. Pharmacol. 124, 291-298, except that the total batch is reduced to 250 µl, such that the assay may be performed on 96-well microtitre plates. The incubation time in these microtitre plates amounts to two hours at room temperature (approx. 20-25° C.).

The following characteristics were determined for the $K_D$ value of the binding site:

$K_D$:24.63±1.56 nM.

EXAMPLES

Yields of the compounds produced are not optimized. All temperatures are uncorrected. The following abbreviations are used in the examples:

| | |
|---|---|
| aq. | aqueous |
| DCM | dichloromethane |
| EDCI | N'-(3-dimethylaminopropyl)-N-ethylcarbodiimide |
| EtOAc | ethyl acetate |
| sat. | saturated |
| h | hours |
| HOAt | 1-hydroxy-7-azabenzotriazole |
| min | minutes |
| MeOH | methanol |
| NMR | nuclear magnetic resonance spectroscopy |
| RT | room temperature |
| THF | tetrahydrofuran |

The chemicals and solvents used were purchased from conventional suppliers (Acros, Avocado, Aldrich, Bachem, Fluka, Lancaster, Maybridge, Merck, Sigma, TCI, etc.) or synthesized by methods known to persons skilled in the art. Silica gel 60 (0.040-0.063 mm) from E. Merck, Darmstadt, was used as the stationary phase for the column chromatography. Thin-layer chromatography was performed with pre-coated silica gel 60 F 254 HPTLC plates from E. Merck, Darmstadt. The mixture ratios for solvents, mobile solvents or for chromatographic investigations are always stated in volume/volume. Analysis was performed by mass spectroscopy and NMR.

General Method for Synthesis of the Example Compounds of the Invention

Stage 1.

1,5,7-Triazabicyclo[4.4.0]dec-5-ene (on polystyrene, 72.6 mmol/g, 28 mmol) is added to a reaction mixture of a nitroolefin corresponding to formula III (14 mmol) and isocyanoacetic acid ethyl ester (14 mmol) in isopropanol (10 mL) and THF (10 mL) and the reaction mixture is stirred overnight at RT under nitrogen as protective gas. The reaction mixture is filtered out and the residue is washed with isopropanol and THF and the desired product corresponding to formula V is thus obtained.

Stage 2.

Sodium hydride (60% in mineral oil, 24 mmol) is added to a solution of the compound corresponding to formula V (12 mmol) in THF (20 mL) at 0° C. and under nitrogen as inert gas and the reaction mixture is stirred for 30 min. Then a compound corresponding to formula $R^3$-LG (24 mmol) is added to the reaction mixture and the reaction mixture is stirred for 1 h to 2 h at 0° C. and overnight or over the weekend at RT. After the addition of a few drops of water and aq. sat. NaCl solution (200 mL), extraction is performed with DCM (2×100 mL). After drying the combined organic phases over sodium sulfate, filtration and removal of the solvent, purification optionally proceeds by means of column chromatography and the desired product corresponding to formula VI is obtained.

Stage 3.

A reaction mixture consisting of a compound corresponding to formula VI (6 mmol) and sodium hydroxide (120 mmol) in MeOH (180 mL) and water (60 mL) is refluxed for 1 h to 3 h. After removal of the solvent, aq. 1N NaOH (400 mL) is added and extraction performed with EtOAc (3×40 mL). After drying of the combined organic phases over sodium sulfate, filtration and removal of the solvent, the product corresponding to formula II is obtained, which may be used without further purification or purified by means of column chromatography.

Reaction of Amines of Formula $HNR^1R^2$ with Carboxylic Acids of Formula II

EDCI (0.1 mmol) and HOAt (0.01 mmol) are added at 0° C. to a reaction mixture consisting of a compound corresponding to formula II (0.1 mmol) and an amine corresponding to formula $HNR^1R^2$ (0.1 mmol) in DCM (1 mL) and the reaction mixture is stirred for 30 min at 0° C. and overnight at RT. After removal of the solvent, the residue is dissolved in DCM (1 mL), washed with aq. sat. NaCl solution (1 mL) and the separated aqueous phase is extracted with DCM (2×1 mL). The solvent of the combined organic phases is removed and the desired products corresponding to formula I obtained after purification by means of preparative HPLC.

Synthesis of
4-methyl-3-phenyl-1H-pyrrole-2-carboxylic acid
ethyl ester 1,5,7-Triazabicyclo[4.4.0]dec-5-ene on polystyrene (4.7 g, 2.6 mmol/g, 12.2 mmol) was added to a reaction mixture of trans-β-methyl-β-nitrostyrene (997 mg, 6.11 mmol) and isocyanoacetic acid ethyl ester (691 mg, 6.11 mmol) in isopropanol (5 mL) and THF (5 mL) and the reaction mixture was stirred overnight at RT under nitrogen as protective gas. The reaction mixture was filtered out and the residue washed with isopropanol and THF. The desired product 4-methyl-3-phenyl-1H-pyrrole-2-carboxylic acid ethyl ester (1.25 g, 89% of theoretical) was obtained.

Synthesis of
1,4-dimethyl-3-phenyl-1H-pyrrole-2-carboxylic acid
ethyl ester

Sodium hydride (436 mg, 60% in mineral oil, 10.9 mmol) was added to a solution of 4-methyl-3-phenyl-1H-pyrrole-2-carboxylic acid ethyl ester (1.25 g, 5.45 mmol) in THF (10 mL) at 0° C. and under nitrogen as inert gas and the reaction mixture was stirred for 15 min. Then methyl iodide (1,547 g, 10.9 mmol) was added to the reaction mixture and the reaction mixture was stirred for 1 h at 0° C. and overnight at RT. After the addition of a few drops of water and aq. sat. NaCl solution (250 mL), extraction was performed with DCM (2×250 mL). After drying of the combined organic phases over sodium sulfate, filtration and removal of the solvent, purification was performed by means of column chromatography. The desired product 1,4-dimethyl-3-phenyl-1H-pyrrole-2-carboxylic acid ethyl ester (1.02 g, 77% of theoretical) was obtained.

Synthesis of
1,4-dimethyl-3-phenyl-1H-pyrrole-2-carboxylic acid

A reaction mixture of 1,4-dimethyl-3-phenyl-1H-pyrrole-2-carboxylic acid ethyl ester (336 mg, 1.38 mmol) and sodium hydroxide (1.10 g, 28 mmol) in MeOH (45 mL) and water (15 mL) was refluxed for 1 h. After removal of the solvent, aqueous 1N NaOH (100 mL) was added and extraction performed with EtOAc (2×20 mL). After drying of the combined organic phases over sodium sulfate, filtration and removal of the solvent, 4-dimethyl-3-phenyl-1H-pyrrole-2-carboxylic acid (270 mg, 91% of theoretical) was obtained.

Example Compound 241

1,4-Dimethyl-3-phenyl-1H-pyrrole-2-carboxylic acid
(2-p-tolylethyl)-amide

EDCI (265 mg, 1.38 mmol) and HOAt (17 mg, 0.12 mmol) were added at 0° C. to a reaction mixture of 4-dimethyl-3-phenyl-1H-pyrrole-2-carboxylic acid (270 mg, 1.25 mmol) and 2-(tolyl)ethylamine (169 mg, 1.25 mmol) in DCM (5 mL) and the reaction mixture was stirred for 30 min at 0° C. and overnight at RT. After removal of the solvent, purification proceeded by means of column chromatography and the desired product 1,4-dimethyl-3-phenyl-1H-pyrrole-2-carboxylic acid (2-p-tolylethyl)-amide (252 mg, 60% of theoretical) was obtained.

Example Compound 242

(1,4-Dimethyl-3-phenyl-1H-pyrrol-2-yl)-[4-(4-fluorophenyl)-piperazin-1-yl]-methanone EDCI (255 mg, 1.33 mmol) and HOAt (16 mg, 0.12 mmol) were added at 0° C. to a reaction mixture of 4-dimethyl-3-phenyl-1H-pyrrole-2-carboxylic acid (260 mg, 1.21 mmol) and 1-(4-fluorophenyl)piperazine (215 mg, 1.21 mmol) in DCM (5 mL) and the reaction mixture was stirred for 30 min at 0° C. and overnight at RT. After removal of the solvent, purification proceeded by means of column chromatography and (1,4-dimethyl-3-phenyl-1H-pyrrol-2-yl)-[4-(4-fluorophenyl)-piperazin-1-yl]-methanone (362 mg, 79% of theoretical) was obtained.

Synthesis of
4-methyl-3-p-tolyl-1H-pyrrole-2-carboxylic acid
ethyl ester 1,5,7-Triazabicyclo[4.4.0]dec-5-ene on polystyrene (5.36 g, 2.6 mmol/g, 13.9 mmol) was added to a reaction mixture of 4-methyl-β-ethyl-β-nitrostyrene (1.23 g, 6.94 mmol) and isocyanoacetic acid ethyl ester (788 mg, 6.90 mmol) in isopropanol (5 mL) and THF (5 mL) and the reaction mixture was stirred overnight at RT under nitrogen as protective gas. The reaction mixture was filtered out and the residue washed with isopropanol and THF. The desired product 4-methyl-3-p-tolyl-1H-pyrrole-2-carboxylic acid ethyl ester (1.42 g, 85% of theoretical) was obtained.

Synthesis of 4-methyl-1-(4-methylbenzyl)-3-p-tolyl-1H-pyrrole-2-carboxylic acid ethyl ester Sodium hydride (470 mg, 60% in mineral oil, 11.8 mmol) was added to a solution of 4-methyl-3-p-tolyl-1H-pyrrole-2-carboxylic acid ethyl ester (1.42 g, 5.84 mmol) in THF (10 mL) at 0° C. and under nitrogen as inert gas and the reaction mixture was stirred for 15 min. Then p-bromobenzyl bromide (2.16 g, 11.7 mmol) was added to the reaction mixture and the reaction mixture was stirred for 30 min at 0° C. and overnight at RT. After the addition of a few drops of water and aq. sat. NaCl solution (100 mL), extraction was performed with DCM (2×50 mL). After drying of the combined organic phases over sodium sulfate, filtration and removal of the solvent, purification was performed via column chromatography. 4-Methyl-1-(4-methylbenzyl)-3-p-tolyl-1H-pyrrole-2-carboxylic acid ethyl ester (1.03 g, 51% of theoretical) was obtained.

Synthesis of 4-methyl-1-(4-methylbenzyl)-3-p-tolyl-1H-pyrrole-2-carboxylic acid

A reaction mixture of 4-methyl-1-(4-methylbenzyl)-3-p-tolyl-1H-pyrrole-2-carboxylic acid ethyl ester (550 mg, 1.58 mmol) and NaOH (1.26 g, 32 mmol) in MeOH (45 mL) and $H_2O$ (15 mL) was refluxed for 1 h. After removal of the solvent, aqueous 1N NaOH (100 mL) was added and extraction performed with EtOAc (2×20 mL). After drying of the combined organic phases over $Na_2SO_4$, filtration and removal of the solvent, the desired product 4-methyl-1-(4-methylbenzyl)-3-p-tolyl-1H-pyrrole-2-carboxylic acid was obtained, which was used without further purification.

Example Compound 69

Synthesis of [4-(2-diethylamino-ethyl)-piperazin-1-yl]-[4-methyl-1-(4-methylbenzyl)-3-p-tolyl-1H-pyrrol-2-yl]-methanone EDCI (166 mg, 0.87 mmol) and HOAt (11 mg, 0.08 mmol) were added at 0° C. to a reaction mixture of 4-methyl-1-(4-methylbenzyl)-3-p-tolyl-1H-pyrrole-2-carboxylic acid (252 mg, 0.79 mmol) and 1-(2-diethylaminoethyl)-piperazine (146 mg, 0.79 mmol) in DCM (5 mL) and the reaction mixture was stirred for 30 min at 0° C. and overnight at RT. After removal of the solvent, purification proceeded by means of column chromatography and the desired product [4-(2-diethylamino-ethyl)-piperazin-1-yl]-[4-methyl-1-(4-methylbenzyl)-3-p-tolyl-1H-pyrrol-2-yl]-methanone (148 mg, 38% of theoretical) was obtained.

Example Compound 244

Synthesis of 4-methyl-1-(4-methylbenzyl)-3-p-tolyl-1H-pyrrole-2-carboxylic acid [2-(1H-indol-3-yl)-ethyl]-methylamide EDCI (166 mg, 0.87 mmol) and HOAt (11 mg, 0.08 mmol) were added at 0° C. to a reaction mixture of 4-dimethyl-3-phenyl-1H-pyrrole-2-carboxylic acid (0.79 mmol) and [2-(1H-indol-3-yl)-ethyl]-methylamine (138 mg, 0.79 mmol) in DCM (5 mL) and the reaction mixture was stirred for 30 min at 0° C. and overnight at RT. After removal of the solvent, purification proceeded by means of column chromatography and the desired product 4-Methyl-1-(4-methylbenzyl)-3-p-tolyl-1H-pyrrole-2-carboxylic acid [2-(1H-indol-3-yl)-ethyl]-methylamide (170 mg, 45% of theoretical) was obtained.

The following example compounds were obtained as described above in the general method. The respective starting materials used are known to persons skilled in the art.

[1] 1-benzyl-4-methyl-3-p-tolyl-1H-pyrrole-2-carboxylic acid 4-[1,2,3]thiadiazol-4-ylbenzylamide,
[2] 3-furan-2-yl-1,4-dimethyl-1H-pyrrole-2-carboxylic acid 4-sulfamoylbenzylamide,
[3] 1-(4-fluorobenzyl)-3-furan-2-yl-4-methyl-1H-pyrrole-2-carboxylic acid 2,4-dimethoxybenzylamide,
[4] 1-butyl-4-methyl-3-p-tolyl-1H-pyrrole-2-carboxylic acid (2-pyridin-2-ylethyl)-amide,
[5] 1-(4-fluorobenzyl)-3-(4-methoxyphenyl)-4-methyl-1H-pyrrole-2-carboxylic acid [2-(5-hydroxy-1H-indol-3-yl)-ethyl]-amide,
[6] (1,4-dimethyl-3-p-tolyl-1H-pyrrole-2-yl)-(4-pyrrolidin-1-ylpiperidin-1-yl)-methanone,
[7] 1-benzyl-3-furan-2-yl-4-methyl-1H-pyrrole-2-carboxylic acid 4-bromo-2-fluorobenzylamide,
[8] [1-benzyl-3-(4-chlorophenyl)-4-methyl-1H-pyrrol-2-yl]-[4-(2-chlorophenyl)-piperazin-1-yl]-methanone,
[9] 1,4-dimethyl-3-phenyl-1H-pyrrole-2-carboxylic acid (3-dimethylamino-propyl)-amide,
[10] 1,4-dimethyl-3-p-tolyl-1H-pyrrole-2-carboxylic acid (2-pyrrolidin-1-ylethyl)-amide,
[11] 1-(4-fluorobenzyl)-3-furan-2-yl-4-methyl-1H-pyrrole-2-carboxylic acid 4-dimethylaminobenzylamide,
[12] 1-[4-(1-benzyl-4-methyl-3-phenyl-1H-pyrrole-2-carbonyl)-piperazin-1-yl]-2-phenylethanone,
[13] 1-benzyl-3-furan-2-yl-4-methyl-1H-pyrrole-2-carboxylic acid 2,5-difluorobenzylamide,
[14] 1-(2,6-dichlorobenzyl)-4-methyl-3-p-tolyl-1H-pyrrole-2-carboxylic acid 3,5-difluorobenzylamide,
[15] 1-(2-bromobenzyl)-3-(4-chlorophenyl)-4-methyl-1H-pyrrole-2-carboxylic acid (2-methylcyclohexyl)-amide,
[16] 1,4-dimethyl-3-p-tolyl-1H-pyrrole-2-carboxylic acid (3-morpholin-4-ylpropyl)-amide,
[17] 1-butyl-4-methyl-3-p-tolyl-1H-pyrrole-2-carboxylic acid (1,3-dimethylbutyl)-amide,
[18] [4-(2,4-dimethylphenyl)-piperazin-1-yl]-[4-methyl-1-(4-methylbenzyl)-3-p-tolyl-1H-pyrrol-2-yl]-methanone,
[19] 1-(2,6-dichlorobenzyl)-4-methyl-3-p-tolyl-1H-pyrrole-2-carboxylic acid methyl-(2-pyridin-2-ylethyl)-amide,
[20] 1,4-dimethyl-3-phenyl-1H-pyrrole-2-carboxylic acid (2-cyano-ethyl)-methylamide, -continued

[21] 1-(2,6-dichlorobenzyl)-4-methyl-3-p-tolyl-1H-pyrrole-2-carboxylic acid (3-imidazol-1-ylpropyl)-amide,
[22] 1-(4-fluorobenzyl)-3-(4-methoxyphenyl)-4-methyl-1H-pyrrole-2-carboxylic acid (1,3-dimethylbutyl)-amide,
[23] 3-(4-methoxyphenyl)-1,4-dimethyl-1H-pyrrole-2-carboxylic acid 2-ethoxybenzylamide,
[24] (4-cycloheptylpiperazin-1-yl)-(1,4-dimethyl-3-p-tolyl-1H-pyrrol-2-yl)-methanone,
[25] 1-(4-fluorobenzyl)-3-(4-methoxyphenyl)-4-methyl-1H-pyrrole-2-carboxylic acid (2-dimethylamino-ethyl)-amide,
[26] 1-benzyl-4-methyl-3-phenyl-1H-pyrrole-2-carboxylic acid (pyridin-2-ylmethyl)-amide,
[27] 3-(4-chlorophenyl)-1-ethyl-4-methyl-1H-pyrrole-2-carboxylic acid [2-(4-chlorophenyl)-propyl]-amide,
[28] 3-(4-chlorophenyl)-1-(2-fluorobenzyl)-4-methyl-1H-pyrrole-2-carboxylic acid 3,5-difluorobenzylamide,
[29] 2-{[1-(4-fluorobenzyl)-3-(4-methoxyphenyl)-4-methyl-1H-pyrrole-2-carbonyl]-amino}-propionic acid benzyl ester,
[30] (1-benzyl-4-methyl-3-p-tolyl-1H-pyrrol-2-yl)-[4-(2-dimethylamino-ethyl)-piperazin-1-yl]-methanone,
[31] 3-furan-2-yl-1-(4-methoxybenzyl)-4-methyl-1H-pyrrole-2-carboxylic acid (3,3-dimethylbutyl)-amide,
[32] 3-(4-chlorophenyl)-1-isobutyl-4-methyl-1H-pyrrole-2-carboxylic acid 4-dimethylaminobenzylamide,
[33] 3-(4-chlorophenyl)-1-ethyl-4-methyl-1H-pyrrole-2-carboxylic acid (2-pyridin-2-ylethyl)-amide,
[34] 3-(4-chlorophenyl)-1-ethyl-4-methyl-1H-pyrrole-2-carboxylic acid 2,3-dimethoxybenzylamide,
[35] 1-(4-fluorobenzyl)-3-(4-methoxyphenyl)-4-methyl-1H-pyrrole-2-carboxylic acid (2-thiophen-2-ylethyl)-amide,
[36] 2-{[3-(4-chlorophenyl)-1-ethyl-4-methyl-1H-pyrrole-2-carbonyl]-amino}-3-methylbutyric acid tert.-butyl ester,
[37] 3-furan-2-yl-1-(4-methoxybenzyl)-4-methyl-1H-pyrrole-2-carboxylic acid (1,2,3,4-tetrahydro-naphthalen-1-yl)-amide,
[38] 3-furan-2-yl-4-methyl-1-(4-trifluoromethylbenzyl)-1H-pyrrole-2-carboxylic acid (2-pyrrolidin-1-ylethyl)-amide,
[39] {[1-(4-methoxybenzyl)-4-methyl-3-p-tolyl-1H-pyrrole-2-carbonyl]-methylamino}-acetic acid benzyl ester,
[40] 3-furan-2-yl-1-(4-methoxybenzyl)-4-methyl-1H-pyrrole-2-carboxylic acid [2-(1-methylpyrrolidin-2-yl)-ethyl]-amide,
[41] [4-(5-bromo-2-ethoxybenzyl)-piperazin-1-yl]-(1,4-dimethyl-3-phenyl-1H-pyrrol-2-yl)-methanone,
[42] (1-benzyl-3-furan-2-yl-4-methyl-1H-pyrrol-2-yl)-[4-(3-fluoro-4-methoxybenzyl)-piperazin-1-yl]-methanone,
[43] 3-{[3-(4-chlorophenyl)-1-ethyl-4-methyl-1H-pyrrole-2-carbonyl]-amino}-propionic acid tert.-butyl ester,
[44] 1-benzyl-4-methyl-3-phenyl-1H-pyrrole-2-carboxylic acid 3-methoxybenzylamide,
[45] (1-benzyl-3-furan-2-yl-4-methyl-1H-pyrrol-2-yl)-[4-(5-bromo-2-ethoxybenzyl)-piperazin-1-yl]-methanone,
[46] [3-(4-chlorophenyl)-1,4-dimethyl-1H-pyrrol-2-yl]-(4-o-tolylpiperazin-1-yl)-methanone,
[47] 1-(4-fluorobenzyl)-3-(4-methoxyphenyl)-4-methyl-1H-pyrrole-2-carboxylic acid [2-(4-ethoxyphenyl)-ethyl]-amide,
[48] [1-(2,6-dichlorobenzyl)-4-methyl-3-p-tolyl-1H-pyrrol-2-yl]-(4-hydroxypiperidin-1-yl)-methanone,
[49] (1,4-dimethyl-3-p-tolyl-1H-pyrrol-2-yl)-[4-(2,4,6-trimethoxybenzyl)-piperazin-1-yl]-methanone,
[50] 1-(4-fluorobenzyl)-3-furan-2-yl-4-methyl-1H-pyrrole-2-carboxylic acid (2-morpholin-4-ylethyl)-amide,
[51] 1-benzyl-3-(4-chlorophenyl)-4-methyl-1H-pyrrole-2-carboxylic acid [2-(4-fluorophenyl)-ethyl]-amide,
[52] [4-(2,5-dimethylphenyl)-piperazin-1-yl]-[3-(4-methoxyphenyl)-1,4-dimethyl-1H-pyrrol-2-yl]-methanone,
[53] 3-(4-methoxyphenyl)-1,4-dimethyl-1H-pyrrole-2-carboxylic acid (3-imidazol-1-ylpropyl)-amide,
[54] 1-(4-fluorobenzyl)-3-(4-methoxyphenyl)-4-methyl-1H-pyrrole-2-carboxylic acid [2-(3-trifluoromethylphenyl)-ethyl]-amide,
[55] [3-(4-chlorophenyl)-1-(2-fluorobenzyl)-4-methyl-1H-pyrrol-2-yl]-[4-(5-methylpyrazin-2-carbonyl)-piperazin-1-yl]-methanone,
[56] 3-(4-chlorophenyl)-1-isobutyl-4-methyl-1H-pyrrole-2-carboxylic acid 3-fluoro-5-trifluoromethylbenzylamide,
[57] [3-(4-chlorophenyl)-1,4-dimethyl-1H-pyrrol-2-yl]-(4-pyridin-4-ylpiperazin-1-yl)-methanone,
[58] 3-(4-chlorophenyl)-1-(2-fluorobenzyl)-4-methyl-1H-pyrrole-2-carboxylic acid (3-imidazol-1-ylpropyl)-amide,
[59] (1,4-dimethyl-3-phenyl-1H-pyrrol-2-yl)-[4-(3-fluoro-methoxybenzyl)-piperazin-1-yl]-methanone,
[60] 1-benzyl-3-furan-2-yl-4-methyl-1H-pyrrole-2-carboxylic acid [2-(4-bromophenyl)-ethyl]-amide,
[61] (4-cycloheptylpiperazin-1-yl)-(3-furan-2-yl-1,4-dimethyl-1H-pyrrol-2-yl)-methanone,
[62] 1-benzyl-4-methyl-3-phenyl-1H-pyrrole-2-carboxylic acid [2-(4-methoxyphenoxy)-ethyl]-amide,
[63] 1-(4-fluorobenzyl)-3-furan-2-yl-4-methyl-1H-pyrrole-2-carboxylic acid (3-dimethylamino-propyl)-amide,

- [64] [1-(4-fluorobenzyl)-3-(4-methoxyphenyl)-4-methyl-1H-pyrrol-2-yl]-(2-pyrrolidin-1-ylmethylpyrrolidin-1-yl)-methanone,
- [65] 3-(4-chlorophenyl)-1-isobutyl-4-methyl-1H-pyrrole-2-carboxylic acid (3-diethylaminopropyl)-amide,
- [66] [3-(4-chlorophenyl)-1,4-dimethyl-1H-pyrrol-2-yl]-[4-(2-fluoro-5-methoxybenzyl)-piperazin-1-yl]-methanone,
- [67] 3-(4-methoxyphenyl)-1,4-dimethyl-1H-pyrrole-2-carboxylic acid pentylamide,
- [68] (1-butyl-4-methyl-3-p-tolyl-1H-pyrrol-2-yl)-[4-(2,5-dimethoxybenzyl)-piperazin-1-yl]-methanone,
- [69] [4-(2-diethylamino-ethyl)-piperazin-1-yl]-[4-methyl-1-(4-methylbenzyl)-3-p-tolyl-1H-pyrrol-2-yl]-methanone,
- [70] [4-(3-chlorophenyl)-piperazin-1-yl]-[3-(4-methoxyphenyl)-1,4-dimethyl-1H-pyrrol-2-yl]-methanone,
- [71] [1-(2-bromobenzyl)-3-(4-chlorophenyl)-4-methyl-1H-pyrrol-2-yl]-(4-isopropylpiperazin-1-yl)-methanone,
- [72] [4-(2-dimethylamino-ethyl)-piperazin-1-yl]-[1-(4-fluorobenzyl)-3-(4-methoxyphenyl)-4-methyl-1H-pyrrol-2-yl]-methanone,
- [73] 3-(4-chlorophenyl)-1-(2-fluorobenzyl)-4-methyl-1H-pyrrole-2-carboxylic acid 2,4-dimethoxybenzylamide,
- [74] 1-benzyl-4-methyl-3-p-tolyl-1H-pyrrole-2-carboxylic acid (2-pyrrolidin-1-ylethyl)-amide,
- [75] [1-(4-fluorobenzyl)-3-furan-2-yl-4-methyl-1H-pyrrol-2-yl]-[4-(3-fluoro-4-methoxybenzyl)-piperazin-1-yl]-methanone,
- [76] 3-(4-methoxyphenyl)-1,4-dimethyl-1H-pyrrole-2-carboxylic acid 2,4-dimethoxybenzylamide,
- [77] 1-benzyl-4-methyl-3-phenyl-1H-pyrrole-2-carboxylic acid (2-pyrrolidin-1-ylethyl)-amide,
- [78] 3-(4-chlorophenyl)-1,4-dimethyl-1H-pyrrole-2-carboxylic acid [3-(2-methylpiperidin-1-yl)-propyl]-amide,
- [79] 1-(4-fluorobenzyl)-3-furan-2-yl-4-methyl-1H-pyrrole-2-carboxylic acid cyclohexylamide,
- [80] 3-furan-2-yl-1,4-dimethyl-1H-pyrrole-2-carboxylic acid 4-fluoro-2-trifluoromethylbenzylamide,
- [81] 1-benzyl-3-furan-2-yl-4-methyl-1H-pyrrole-2-carboxylic acid (1-naphthalen-2-ylethyl)-amide,
- [82] 3-(4-chlorophenyl)-1-ethyl-4-methyl-1H-pyrrole-2-carboxylic acid (furan-2-ylmethyl)-amide,
- [83] 1-benzyl-4-methyl-3-phenyl-1H-pyrrole-2-carboxylic acid (3-dimethylamino-propyl)-methylamide,
- [84] [3-(4-methoxyphenyl)-1,4-dimethyl-1H-pyrrol-2-yl]-(4-p-tolylpiperazin-1-yl)-methanone,
- [85] 1-(4-methoxybenzyl)-4-methyl-3-p-tolyl-1H-pyrrole-2-carboxylic acid (thiophen-2-ylmethyl)-amide,
- [86] 4-methyl-1-(4-methylbenzyl)-3-p-tolyl-1H-pyrrole-2-carboxylic acid phenethylamide,
- [87] 1,4-dimethyl-3-p-tolyl-1H-pyrrole-2-carboxylic acid 3,5-difluorobenzylamide,
- [88] 3-(4-methoxyphenyl)-1,4-dimethyl-1H-pyrrole-2-carboxylic acid indan-1-ylamide,
- [89] 1-benzyl-4-methyl-3-phenyl-1H-pyrrole-2-carboxylic acid 4-dimethylaminobenzylamide,
- [90] 1-(4-fluorobenzyl)-3-furan-2-yl-4-methyl-1H-pyrrole-2-carboxylic acid (1-naphthalen-2-ylmethylpyrrolidin-3-yl)-amide,
- [91] [3-furan-2-yl-4-methyl-1-(4-trifluoromethylbenzyl)-1H-pyrrol-2-yl]-(4-methyl-[1,4]diazepan-1-yl)-methanone,
- [92] [1-(2-bromobenzyl)-3-(4-chlorophenyl)-4-methyl-1H-pyrrol-2-yl]-[4-(3-trifluoromethylphenyl)-piperazin-1-yl]-methanone,
- [93] [3-furan-2-yl-1-(4-methoxybenzyl)-4-methyl-1H-pyrrol-2-yl]-(4-thiophen-3-ylmethylpiperazin-1-yl)-methanone,
- [94] 1,4-dimethyl-3-p-tolyl-1H-pyrrole-2-carboxylic acid (2-benzyloxy-cyclohexyl)-amide,
- [95] 2-{4-[1-benzyl-3-(4-chlorophenyl)-4-methyl-1H-pyrrole-2-carbonyl]-piperazin-1-yl}-N-isopropylacetamide,
- [96] (2,6-dimethylmorpholin-4-yl)-[3-(4-methoxyphenyl)-1,4-dimethyl-1H-pyrrol-2-yl]-methanone,
- [97] 3-furan-2-yl-1-(4-methoxybenzyl)-4-methyl-1H-pyrrole-2-carboxylic acid (thiophen-2-ylmethyl)-amide,
- [98] 1,4-dimethyl-3-p-tolyl-1H-pyrrole-2-carboxylic acid (furan-2-ylmethyl)-amide,
- [99] 4-methyl-1-(4-methylbenzyl)-3-p-tolyl-1H-pyrrole-2-carboxylic acid (3-dimethylaminopropyl)-amide,
- [100] 1-(4-fluorobenzyl)-3-(4-methoxyphenyl)-4-methyl-1H-pyrrole-2-carboxylic acid (2-oxo-tetrahydro-furan-3-yl)-amide,
- [101] 3-(4-chlorophenyl)-1,4-dimethyl-1H-pyrrole-2-carboxylic acid (2-phenoxy-ethyl)-amide,
- [102] 3-(4-(1-benzyl-4-methyl-3-p-tolyl-1H-pyrrole-2-carbonyl)piperazin-1-yl)pyrazine-2-carbonitrile
- [103] 2-{[3-(4-methoxyphenyl)-1,4-dimethyl-1H-pyrrole-2-carbonyl]-amino}-3-phenylpropionic acid methyl ester,
- [104] 3-(4-chlorophenyl)-1,4-dimethyl-1H-pyrrole-2-carboxylic acid (2-morpholin-4-ylethyl)-amide,
- [105] 3-furan-2-yl-1,4-dimethyl-1H-pyrrole-2-carboxylic acid indan-2-ylamide,
- [106] (1-butyl-4-methyl-3-p-tolyl-1H-pyrrol-2-yl)-[4-(2-fluorophenyl)-piperazin-1-yl]-methanone,
- [107] [4-(3-chlorophenyl)-piperazin-1-yl]-(1,4-dimethyl-3-p-tolyl-1H-pyrrol-2-yl)-methanone,

[108] [1-(4-fluorobenzyl)-3-furan-2-yl-4-methyl-1H-pyrrol-2-yl]-(4-naphthalen-2-ylmethylpiperazin-1-yl)-methanone,
[109] 3-(4-chlorophenyl)-1-isobutyl-4-methyl-1H-pyrrole-2-carboxylic acid p-tolylamide,
[110] (1-benzyl-4-methyl-3-p-tolyl-1H-pyrrol-2-yl)-[4-(2-hydroxy-ethyl)-piperazin-1-yl]-methanone,
[111] 1-butyl-4-methyl-3-p-tolyl-1H-pyrrole-2-carboxylic acid [2-(2,5-dimethoxyphenyl)-ethyl]-amide,
[112] 1-butyl-4-methyl-3-p-tolyl-1H-pyrrole-2-carboxylic acid (3-imidazol-1-ylpropyl)-amide,
[113] 1-benzyl-3-(4-chlorophenyl)-4-methyl-1H-pyrrole-2-carboxylic acid [2-(3,4-dimethoxyphenyl)-ethyl]-methylamide,
[114] 4-methyl-1-(4-methylbenzyl)-3-p-tolyl-1H-pyrrole-2-carboxylic acid (3-morpholin-4-ylpropyl)-amide,
[115] 4-methyl-1-(4-methylbenzyl)-3-p-tolyl-1H-pyrrole-2-carboxylic acid 4-fluoro-2-trifluoromethylbenzylamide,
[116] 2-{[1-benzyl-3-(4-chlorophenyl)-4-methyl-1H-pyrrole-2-carbonyl]-amino}-3-(4-chlorophenyl)-propionic acid ethyl ester,
[117] 1-benzyl-4-methyl-3-phenyl-1H-pyrrole-2-carboxylic acid 3-fluoro-4-trifluoromethylbenzylamide,
[118] 1-(4-bromobenzyl)-4-methyl-3-p-tolyl-1H-pyrrole-2-carboxylic acid (2-pyridin-2-ylethyl)-amide,
[119] 1-(4-fluorobenzyl)-3-furan-2-yl-4-methyl-1H-pyrrole-2-carboxylic acid benzyl-(2-hydroxy-ethyl)-amide,
[120] 2-[4-(1-butyl-4-methyl-3-p-tolyl-1H-pyrrole-2-carbonyl)-piperazin-1-yl]-N-methyl-N-phenylacetamide,
[121] [4-methyl-1-(4-methylbenzyl)-3-p-tolyl-1H-pyrrol-2-yl]-(4-phenylpiperazin-1-yl)-methanone,
[122] 1-benzyl-4-methyl-3-p-tolyl-1H-pyrrole-2-carboxylic acid (1-benzylpyrrolidin-3-yl)-amide,
[123] [1-(4-fluorobenzyl)-3-furan-2-yl-4-methyl-1H-pyrrol-2-yl]-[4-(3-trifluoromethylphenyl)-piperazin-1-yl]-methanone,
[124] 1-(4-methoxybenzyl)-4-methyl-3-p-tolyl-1H-pyrrole-2-carboxylic acid butylamide,
[125] 1-benzyl-4-methyl-3-p-tolyl-1H-pyrrole-2-carboxylic acid [2-(2-fluorophenyl)-ethyl]-amide,
[126] 4-methyl-1-(4-methylbenzyl)-3-p-tolyl-1H-pyrrole-2-carboxylic acid 3,4-dimethoxybenzylamide,
[127] 3-(4-chlorophenyl)-1-isobutyl-4-methyl-1H-pyrrole-2-carboxylic acid (2-diethylamino-ethyl)-amide,
[128] 1-{4-[3-(4-chlorophenyl)-1-ethyl-4-methyl-1H-pyrrole-2-carbonyl]-piperazin-1-yl}-2-phenylethanone,
[129] 1-(4-fluorobenzyl)-4-methyl-3-p-tolyl-1H-pyrrole-2-carboxylic acid 3-trifluoromethoxybenzylamide,
[130] [1-benzyl-3-(4-chlorophenyl)-4-methyl-1H-pyrrol-2-yl]-(3-methylpiperidin-1-yl)-methanone,
[131] 1-(4-fluorobenzyl)-4-methyl-3-p-tolyl-1H-pyrrole-2-carboxylic acid (2-p-tolylethyl)-amide,
[132] 1-(4-methoxybenzyl)-4-methyl-3-p-tolyl-1H-pyrrole-2-carboxylic acid [2-(2-methyl-5-nitro-imidazol-1-yl)-ethyl]-amide,
[133] 1,4-dimethyl-3-p-tolyl-1H-pyrrole-2-carboxylic acid 2,3-dimethoxybenzylamide,
[134] 1-(2-bromobenzyl)-3-(4-chlorophenyl)-4-methyl-1H-pyrrole-2-carboxylic acid [2-(ethyl-m-tolylamino)-ethyl]-amide,
[135] 1-(4-fluorobenzyl)-3-furan-2-yl-4-methyl-1H-pyrrole-2-carboxylic acid (4-isopropylphenyl)-amide,
[136] 5-chloro-2-methoxybenzoic acid N'-[1-(4-fluorobenzyl)-3-(4-methoxyphenyl)-4-methyl-1H-pyrrole-2-carbonyl]-hydrazide,
[137] (1-benzyl-4-methyl-3-p-tolyl-1H-pyrrol-2-yl)-[1,4']bipiperidinyl-1'-ylmethanone,
[138] 3-furan-2-yl-1,4-dimethyl-1H-pyrrole-2-carboxylic acid (4-butylphenyl)-amide,
[139] 1-benzyl-4-methyl-3-phenyl-1H-pyrrole-2-carboxylic acid [2-(1H-indol-3-yl)-ethyl]-amide,
[140] [4-(4-tert-butylbenzyl)-piperazin-1-yl]-[1-(4-fluorobenzyl)-4-methyl-3-p-tolyl-1H-pyrrol-2-yl]-methanone,
[141] [1-(4-fluorobenzyl)-4-methyl-3-p-tolyl-1H-pyrrol-2-yl]-morpholin-4-ylmethanone,
[142] 3-[(1-benzyl-3-furan-2-yl-4-methyl-1H-pyrrole-2-carbonyl)-amino]-propionic acid ethyl ester,
[143] 1,4-dimethyl-3-phenyl-1H-pyrrole-2-carboxylic acid (naphthalen-2-ylcarbamoylmethyl)-amide,
[144] [3-(4-chlorophenyl)-1,4-dimethyl-1H-pyrrol-2-yl]-[4-(2-ethoxyphenyl)-piperazin-1-yl]-methanone,
[145] 1-(4-fluorobenzyl)-3-furan-2-yl-4-methyl-1H-pyrrole-2-carboxylic acid (4-cyanomethylphenyl)-amide,
[146] 4-[1-benzyl-3-(4-chlorophenyl)-4-methyl-1H-pyrrole-2-carbonyl]-piperazine-1-carboxylic acid tert.-butyl ester,
[147] (1,4-dioxa-8-aza-spiro[4.5]dec-8-yl)-[1-(4-fluorobenzyl)-3-furan-2-yl-4-methyl-1H-pyrrol-2-yl]-methanone,
[148] 3-furan-2-yl-4-methyl-1-(4-trifluoromethylbenzyl)-1H-pyrrole-2-carboxylic acid pentylamide,
[149] 3-furan-2-yl-1-(4-methoxybenzyl)-4-methyl-1H-pyrrole-2-carboxylic acid [3-(methylphenylamino)-propyl]-amide,
[150] 1-(2,6-dichlorobenzyl)-4-methyl-3-p-tolyl-1H-pyrrole-2-carboxylic acid (2-azepan-1-ylethyl)-amide,
[151] 1-(4-bromobenzyl)-4-methyl-3-p-tolyl-1H-pyrrole-2-carboxylic acid cyclopentylamide, -continued

[152] [1-(2,6-dichlorobenzyl)-4-methyl-3-p-tolyl-1H-pyrrol-2-yl]-[4-(2,4-dimethoxyphenyl)-piperazin-1-yl]-methanone,
[153] 3-(4-chlorophenyl)-1-(2-fluorobenzyl)-4-methyl-1H-pyrrole-2-carboxylic acid [2-(2-chlorophenoxy)-ethyl]-amide,
[154] 1-(2,6-dichlorobenzyl)-4-methyl-3-p-tolyl-1H-pyrrole-2-carboxylic acid (3,3-dimethylbutyl)-amide,
[155] 1,4-dimethyl-3-p-tolyl-1H-pyrrole-2-carboxylic acid (2-benzyloxy-cyclohexyl)-amide,
[156] [4-methyl-1-(4-methylbenzyl)-3-p-tolyl-1H-pyrrol-2-yl]-thiomorpholin-4-ylmethanone,
[157] 3-(4-chlorophenyl)-1-isobutyl-4-methyl-1H-pyrrole-2-carboxylic acid (3-dimethylamino-propyl)-methylamide,
[158] [4-(2,5-dimethylphenyl)-piperazin-1-yl]-[3-furan-2-yl-1-(4-methoxybenzyl)-4-methyl-1H-pyrrol-2-yl]-methanone,
[159] 5-chloro-2-methoxybenzoic acid N'-[3-(4-methoxyphenyl)-1,4-dimethyl-1H-pyrrole-2-carbonyl]-hydrazide,
[160] 2-(3,4-difluorophenyl)-1-{4-[1-(4-fluorobenzyl)-3-furan-2-yl-4-methyl-1H-pyrrole-2-carbonyl]-piperazin-1-yl}-ethanone,
[161] 2-{4-[1-(4-fluorobenzyl)-3-furan-2-yl-4-methyl-1H-pyrrole-2-carbonyl]-piperazin-1-yl}-N-isopropylacetamide,
[162] 3-furan-2-yl-4-methyl-1-(4-trifluoromethylbenzyl)-1H-pyrrole-2-carboxylic acid [1-(3-methoxyphenyl)-ethyl]-amide,
[163] 2-[(1-benzyl-3-furan-2-yl-4-methyl-1H-pyrrole-2-carbonyl)-amino]-3-(4-chlorophenyl)-propionic acid methyl ester,
[164] [3-furan-2-yl-1-(4-methoxybenzyl)-4-methyl-1H-pyrrol-2-yl]-(4-methylpiperazin-1-yl)-methanone,
[165] 1,4-dimethyl-3-phenyl-1H-pyrrole-2-carboxylic acid (1-benzylpyrrolidin-3-yl)-amide,
[166] (1,4-dimethyl-3-p-tolyl-1H-pyrrol-2-yl)-(4-thieno[2,3-d]pyrimidin-4-ylpiperazin-1-yl)-methanone,
[167] 4-methyl-1-(4-methylbenzyl)-3-p-tolyl-1H-pyrrole-2-carboxylic acid (3-methoxy-propyl)-amide,
[168] [3-(4-methoxyphenyl)-1,4-dimethyl-1H-pyrrol-2-yl]-[4-(5-trifluoromethylpyridin-2-yl)-piperazin-1-yl]-methanone,
[169] 1-(4-bromobenzyl)-4-methyl-3-p-tolyl-1H-pyrrole-2-carboxylic acid (3-morpholin-4-ylpropyl)-amide,
[170] 1,4-dimethyl-3-p-tolyl-1H-pyrrole-2-carboxylic acid [2-(2,3-dimethoxyphenyl)-ethyl]-amide,
[171] [1-(4-methoxybenzyl)-4-methyl-3-p-tolyl-1H-pyrrol-2-yl]-(3-methyl-4-p-tolylpiperazin-1-yl)-methanone,
[172] [3-(4-chlorophenyl)-1-ethyl-4-methyl-1H-pyrrol-2-yl]-[4-(2,4-dimethoxyphenyl)-piperazin-1-yl]-methanone,
[173] 2-{4-[1-(2-bromobenzyl)-3-(4-chlorophenyl)-4-methyl-1H-pyrrole-2-carbonyl]-piperazin-1-yl}-benzonitrile,
[174] 1-(4-bromobenzyl)-4-methyl-3-p-tolyl-1H-pyrrole-2-carboxylic acid (1-ethylpyrrolidin-2-ylmethyl)-amide,
[175] 3-(4-chlorophenyl)-1-isobutyl-4-methyl-1H-pyrrole-2-carboxylic acid [2-(2-chlorophenoxy)-ethyl]-amide,
[176] 3-(4-chlorophenyl)-1,4-dimethyl-1H-pyrrole-2-carboxylic acid [2-(1H-indol-3-yl)-ethyl]-amide,
[177] 1-(4-fluorobenzyl)-4-methyl-3-p-tolyl-1H-pyrrole-2-carboxylic acid (naphthalen-2-ylcarbamoylmethyl)-amide,
[178] 4-(1-benzyl-3-furan-2-yl-4-methyl-1H-pyrrole-2-carbonyl)-piperazin-1-carboxylic acid benzyl ester,
[179] 1,4-dimethyl-3-phenyl-1H-pyrrole-2-carboxylic acid (1-benzylpyrrolidin-3-yl)-amide,
[180] [3-(4-chlorophenyl)-1-(2-fluorobenzyl)-4-methyl-1H-pyrrol-2-yl]-[4-(4-trifluoromethylphenyl)-piperazin-1-yl]-methanone,
[181] [3-(4-chlorophenyl)-1-isobutyl-4-methyl-1H-pyrrol-2-yl]-(4-phenylpiperazin-1-yl)-methanone,
[182] 2-{4-[1-butyl-3-(4-chlorophenyl)-4-methyl-1H-pyrrole-2-carbonyl]-piperazin-1-yl}-1-pyrrolidin-1-ylethanone,
[183] [1-benzyl-3-(4-chlorophenyl)-4-methyl-1H-pyrrol-2-yl]-[4-(2-chloro-4-fluorobenzoyl)-piperazin-1-yl]-methanone,
[184] (4-benzoylpiperidin-1-yl)-[1-(4-methoxybenzyl)-4-methyl-3-p-tolyl-1H-pyrrol-2-yl]-methanone,
[185] 3-furan-2-yl-1,4-dimethyl-1H-pyrrole-2-carboxylic acid ethylpyridin-4-ylmethylamide,
[186] 1-(4-bromobenzyl)-4-methyl-3-p-tolyl-1H-pyrrole-2-carboxylic acid (2-pyrrolidin-1-ylethyl)-amide,
[187] [3-(4-chlorophenyl)-1-isobutyl-4-methyl-1H-pyrrol-2-yl]-[4-(4-methylbenzoyl)-piperazin-1-yl]-methanone,
[188] [1-benzyl-3-(4-chlorophenyl)-4-methyl-1H-pyrrol-2-yl]-(4-thieno[2,3-d]pyrimidin-4-ylpiperazin-1-yl)-methanone,
[189] 1-(1,4-dimethyl-3-phenyl-1H-pyrrole-2-carbonyl)-hydroxypiperidine-3-carboxylic acid ethyl ester,
[190] 1,4-dimethyl-3-phenyl-1H-pyrrole-2-carboxylic acid (1-phenylethyl)-amide,
[191] [3-furan-2-yl-1-(4-methoxybenzyl)-4-methyl-1H-pyrrol-2-yl]-(1,3,4,9-tetrahydro-b-carbolin-2-yl)-methanone,
[192] 1-{4-[1-benzyl-3-(4-chlorophenyl)-4-methyl-1H-pyrrole-2-carbonyl]-piperazin-1-yl}-2-(3,4-difluorophenyl)-ethanone,
[193] [1-(4-bromobenzyl)-4-methyl-3-p-tolyl-1H-pyrrol-2-yl]-[4-(3-phenylpropyl)-piperazin-1-yl]-methanone,
[194] 1-(2-bromobenzyl)-3-(4-chlorophenyl)-4-methyl-1H-pyrrole-2-carboxylic acid [2-(1H-indol-3-yl)-ethyl]-methylamide,

- [195] 1-(4-{4-[1-(4-bromobenzyl)-4-methyl-3-p-tolyl-1H-pyrrole-2-carbonyl]-piperazin-1-yl}-phenyl)-ethanone,
- [196] 1,4-dimethyl-3-phenyl-1H-pyrrole-2-carboxylic acid 4-fluoro-2-trifluoromethylbenzylamide,
- [197] 4-methyl-1-(4-methylbenzyl)-3-p-tolyl-1H-pyrrole-2-carboxylic acid (4-phenoxyphenyl)-amide,
- [198] (4-hydroxy-piperidin-1-yl)-[1-(4-methoxybenzyl)-4-methyl-3-p-tolyl-1H-pyrrol-2-yl]-methanone,
- [199] 4-diethylaminobenzoic acid N'-(1-benzyl-4-methyl-3-p-tolyl-1H-pyrrole-2-carbonyl)-hydrazide,
- [200] [3-(4-chlorophenyl)-1-isobutyl-4-methyl-1H-pyrrol-2-yl]-[4-(3-chlorophenyl)-piperazin-1-yl]-methanone,
- [201] 1-(4-bromobenzyl)-4-methyl-3-p-tolyl-1H-pyrrole-2-carboxylic acid [2-(3,4-dichlorophenyl)-ethyl]-amide,
- [202] 3-(4-chlorophenyl)-1-ethyl-4-methyl-1H-pyrrole-2-carboxylic acid [2-(1H-indol-3-yl)-ethyl]-amide,
- [203] [1-(4-fluorobenzyl)-4-methyl-3-p-tolyl-1H-pyrrol-2-yl]-[4-(5-trifluoromethylpyridin-2-yl)-piperazin-1-yl]-methanone,
- [204] 1,4-dimethyl-3-phenyl-1H-pyrrole-2-carboxylic acid 3-trifluoromethoxybenzylamide,
- [205] [1-(4-fluorobenzyl)-4-methyl-3-p-tolyl-1H-pyrrol-2-yl]-[4-(4-methylbenzoyl)-piperazin-1-yl]-methanone,
- [206] [4-(3,4-dichlorophenyl)-piperazin-1-yl]-[1-(4-fluorobenzyl)-4-methyl-3-p-tolyl-1H-pyrrol-2-yl]-methanone,
- [207] 3-(4-chlorophenyl)-1-ethyl-4-methyl-1H-pyrrole-2-carboxylic acid 2,6-dimethoxybenzylamide,
- [208] 4-methyl-1-(4-methylbenzyl)-3-p-tolyl-1H-pyrrole-2-carboxylic acid [2-(3,4-dimethoxyphenyl)-ethyl]-amide,
- [209] 1-{4-[3-(4-chlorophenyl)-1-isobutyl-4-methyl-1H-pyrrole-2-carbonyl]-piperazin-1-yl}-2-(3,4-difluorophenyl)-ethanone,
- [210] [1-(4-fluorobenzyl)-4-methyl-3-p-tolyl-1H-pyrrol-2-yl]-[4-(2-methoxyphenyl)-piperidin-1-yl]-methanone,
- [211] [3-furan-2-yl-4-methyl-1-(4-trifluoromethylbenzyl)-1H-pyrrol-2-yl]-thiomorpholin-4-ylmethanone,
- [212] 1,4-dimethyl-3-phenyl-1H-pyrrole-2-carboxylic acid (2-thiophen-2-ylethyl)-amide,
- [213] 4-diethylaminobenzoic acid N'-(1-butyl-4-methyl-3-p-tolyl-1H-pyrrole-2-carbonyl)-hydrazide,
- [214] {1-[1-(4-fluorobenzyl)-3-(4-methoxyphenyl)-4-methyl-1H-pyrrole-2-carbonyl]-pyrrolidin-3-yl}-carbamic acid tert.-butyl ester,
- [215] 2-{4-[3-(4-chlorophenyl)-1-isobutyl-4-methyl-1H-pyrrole-2-carbonyl]-piperazin-1-yl}-1-pyrrolidin-1-ylethanone,
- [216] [4-(2,3-dihydrobenzo[1,4]dioxine-2-carbonyl)-piperazin-1-yl]-(1,4-dimethyl-3-phenyl-1H-pyrrol-2-yl)-methanone,
- [217] 3-furan-2-yl-1,4-dimethyl-1H-pyrrole-2-carboxylic acid 3,4-dimethoxybenzylamide,
- [218] [3-furan-2-yl-4-methyl-1-(4-trifluoromethylbenzyl)-1H-pyrrol-2-yl]-(4-pyridin-2-ylpiperazin-1-yl)-methanone,
- [219] [4-(furan-2-carbonyl)-piperazin-1-yl]-[3-furan-2-yl-4-methyl-1-(4-trifluoromethylbenzyl)-1H-pyrrol-2-yl]-methanone,
- [220] 3-furan-2-yl-4-methyl-1-(4-trifluoromethylbenzyl)-1H-pyrrole-2-carboxylic acid (4-tert.-butylphenyl)-amide,
- [221] 2-{4-[3-(4-chlorophenyl)-1-isobutyl-4-methyl-1H-pyrrole-2-carbonyl]-piperazin-1-yl}-benzonitrile,
- [222] (3-furan-2-yl-1,4-dimethyl-1H-pyrrol-2-yl)-[4-(4-trifluoromethylpyridin-2-yl)-piperazin-1-yl]-methanone,
- [223] 1,4-dimethyl-3-phenyl-1H-pyrrole-2-carboxylic acid 3,5-difluorobenzylamide,
- [224] 1,4-dimethyl-3-phenyl-1H-pyrrole-2-carboxylic acid (pyridin-4-ylmethyl)-amide,
- [225] 2-[4-(3-furan-2-yl-1,4-dimethyl-1H-pyrrole-2-carbonyl)-piperazin-1-yl]-benzonitrile,
- [226] 3-furan-2-yl-1,4-dimethyl-1H-pyrrole-2-carboxylic acid methyl-(2-pyridin-2-ylethyl)-amide,
- [227] 3-furan-2-yl-1,4-dimethyl-1H-pyrrole-2-carboxylic acid (3-methoxybenzyl)-(tetrahydro-furan-2-ylmethyl)-amide,
- [228] 3-furan-2-yl-1,4-dimethyl-1H-pyrrole-2-carboxylic acid (4-phenoxyphenyl)-amide,
- [229] 3-furan-2-yl-1,4-dimethyl-1H-pyrrole-2-carboxylic acid pentylamide,
- [230] 2-(3,4-difluorophenyl)-1-[4-(3-furan-2-yl-1,4-dimethyl-1H-pyrrole-2-carbonyl)-piperazin-1-yl]-ethanone,
- [231] 3-furan-2-yl-1,4-dimethyl-1H-pyrrole-2-carboxylic acid phenylamide,
- [232] [4-(2,4-dimethoxyphenyl)-piperazin-1-yl]-(3-furan-2-yl-1,4-dimethyl-1H-pyrrol-2-yl)-methanone,
- [233] 3-furan-2-yl-1,4-dimethyl-1H-pyrrole-2-carboxylic acid [2-(3,4-dichlorophenyl)-ethyl]-amide,
- [234] 3-furan-2-yl-1,4-dimethyl-1H-pyrrole-2-carboxylic acid [2-(2-chlorophenoxy)-ethyl]-amide,
- [235] 3-furan-2-yl-1,4-dimethyl-1H-pyrrole-2-carboxylic acid 3-methoxybenzylamide,
- [236] 3-furan-2-yl-4-methyl-1-(4-trifluoromethylbenzyl)-1H-pyrrole-2-carboxylic acid phenethylamide,
- [237] 3-furan-2-yl-1,4-dimethyl-1H-pyrrole-2-carboxylic acid cyclopentylamide,
- [238] 3-furan-2-yl-1,4-dimethyl-1H-pyrrole-2-carboxylic acid (pyridin-2-ylmethyl)-amide,
- [239] 3-furan-2-yl-4-methyl-1-(4-trifluoromethylbenzyl)-1H-pyrrole-2-carboxylic acid [2-(3,4-dimethoxyphenyl)-ethyl]-amide,
- [240] [1-(4-bromobenzyl)-4-methyl-3-p-tolyl-1H-pyrrol-2-yl]-(2,6-dimethylmorpholin-4-yl)-methanone,

[241] 1,4-dimethyl-3-phenyl-1H-pyrrole-2-carboxylic acid (2-p-tolylethyl)-amide,
[242] (1,4-dimethyl-3-phenyl-1H-pyrrol-2-yl)-[4-(4-fluorophenyl)-piperazin-1-yl]-methanone
[243] 4-methyl-1-(4-methylbenzyl)-3-p-tolyl-1H-pyrrole-2-carboxylic acid [2-(1H-indol-3-yl)-ethyl]-methylamide, Pharmacological Data:

The noradrenalin reuptake inhibition (NA uptake inhibition) and the serotonin reuptake inhibition (5-HT uptake inhibition) of the 1,3-disubstituted 4-methyl-1H-pyrrole-2-carboxamides according to the invention was determined as described above. The 1,3-disubstituted 4-methyl-1H-pyrrole-2-carboxamides according to the invention exhibit excellent affinity for the noradrenalin receptor and for the 5-HT receptor. Furthermore, these compounds according to the invention also exhibit excellent affinities for the batrachotoxin (BTX) binding site of the sodium channel. The following Table I gives the respective pharmacological data for some example 1,3-disubstituted 4-methyl-1H-pyrrole-2-carboxamides.

TABLE 1

| Compound according to Example | 5-HT uptake (% inhibition at 10 μM) | NA uptake (% inhibition at 10 μM) | BTX (Na+ channel) (% inhibition at 10 μM) |
|---|---|---|---|
| 3 | 58 | | |
| 4 | 39 | | |
| 8 | | 70 | |
| 18 | 50 | | |
| 19 | 39 | | |
| 24 | 54 | 33 | |
| 35 | | 37 | |
| 26 | | 33 | |
| 29 | 52 | | |
| 32 | | 35 | |
| 34 | 37 | | |
| 35 | | | 48 |
| 36 | 74 | | |
| 37 | 68 | | |
| 38 | | | 94 |
| 39 | 54 | | 74 |
| 40 | | | 81 |
| 41 | 37 | | 77 |
| 42 | | | 88 |
| 43 | | | 31 |
| 44 | | | 47 |
| 45 | | | 89 |
| 46 | 34 | 63 | 55 |
| 47 | 67 | | 55 |
| 48 | | | 36 |
| 49 | 30 | | 89 |
| 50 | | | 77 |
| 51 | | | 43 |
| 52 | | | 76 |
| 53 | | | 44 |
| 54 | | | 42 |
| 55 | | | 44 |
| 57 | 66 | | 76 |
| 58 | 50 | | 93 |
| 59 | | | 75 |
| 60 | 67 | | |
| 61 | 52 | 34 | 64 |
| 62 | 73 | | 50 |
| 63 | 50 | 57 | 75 |
| 64 | | | 96 |
| 65 | | 35 | 88 |
| 66 | | | 73 |
| 68 | | | 84 |
| 69 | | | 91 |
| 70 | 54 | 69 | 59 |
| 71 | | | 83 |
| 72 | | | 81 |
| 73 | | | 49 |
| 74 | | | 101 |

TABLE 1-continued

| Compound according to Example | 5-HT uptake (% inhibition at 10 μM) | NA uptake (% inhibition at 10 μM) | BTX (Na+ channel) (% inhibition at 10 μM) |
|---|---|---|---|
| 75 | | | 89 |
| 76 | | | 41 |
| 77 | | | 91 |
| 78 | | 32 | 86 |
| 80 | | 30 | |
| 81 | | 57 | 35 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A 1,3-disubstituted 4-methyl-1H-pyrrole-2-carboxamide compound corresponding to formula I

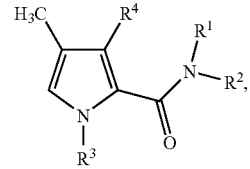

wherein
R$^1$ denotes
C$_{1-6}$ alkyl, C$_{2-6}$ alkenyl or —C$_{2-6}$ alkynyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluyl), —N(C$_2$H$_5$)-(p-toluyl), —N(CH$_3$)-(p-toluoyl) and —NH—C(=O)—O—C(CH$_3$)$_3$;

2- to 6-membered heteroalkyl, which is in each case unsubstituted or optionally substituted with 1, 2, 3, 4 or 5 substituents independently selected from the group consisting of F, Cl, Br, I, —NO$_2$, —CN, —OH, —SH and —NH$_2$ and in each case 1 or 2 heteroatom(s) independently selected from the group consisting of oxygen, sulfur and nitrogen (NH) as chain link(s);

C$_{3-7}$ cycloalkyl, C$_{5-6}$ cycloalkenyl, 5- to 7-membered heterocycloalkyl, 5- to 7-membered heterocycloalkenyl, (1,2,3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1,4]dioxinyl or benzo[1,3]diox-olyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—$CH_3$, —O—$C_2H_5$, —O—$C_3H_7$, —O-phenyl, —O—$CH_2$-phenyl, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —S—$CH_3$, —S—$C_2H_5$, —C(=O)—$CH_3$, —C(=O)—$C_2H_5$, —C(=O)—$C(CH_3)_3$, —C(=O)—NH—$CH_3$, —C(=O)—NH—$C_2H_5$, —$CH_2$-naphthyl, benzyl and phenyl and/or in each case may be attached via an unsubstituted $C_{1-3}$ alkylene, $C_{2-3}$ alkenylene or $C_{2-3}$ alkynylene group and/or in each case may comprise 1 or 2 heteroatom(s) independently selected from the group consisting of oxygen, sulfur and nitrogen (NH) as ring member(s);

phenyl, which in each case may optionally be attached via a $C_{1-3}$ alkylene, $C_{2-3}$ alkenylene or $C_{2-3}$ alkynylene group, which is in each case unsubstituted or substituted with 1 or 2 substituents selected from the group consisting of F, —C(=O)—O—$CH_3$ and —C(=O)—O—$C_2H_5$, or via a —$CH_2$—$CH_2$—O—, —$CH_2$—O— or —$CH_2$—$CH_2$—$CH_2$—O— group and/or is in each case unsubstituted or substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—$Si(CH_3)_3$, —C≡C—$Si(C_2H_5)_3$, —$CH_2$—O—$CH_3$, —$CH_2$—O—$C_2H_5$, —$NH_2$, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, —$N(CH_3)_2$, —$N(C_2H_5)_2$, —NH—$CH_3$, —NH—$C_2H_5$, —$CH_2$—O—C(=O)-phenyl, —NH—S(=O)$_2$—$CH_3$, —C(=O)—H, —C(=O)—$CH_3$, —C(=O)—NH—C(=O)—$CH_3$, —NH—C(=O)—$C_2H_5$, —O—C(=O)-phenyl, —C(=O)—$NH_2$, —C(=O)—NH—$CH_3$, —C(=O)—NH—$C_2H_5$, —C(=O)O—NH—$C(CH_3)_3$, —C(=O)—N$(C_2H_5)_2$, —S(=O)—$NH_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —$NO_2$, —OH, —SH, —$NH_2$, methyl, ethyl, n-propyl, isopropyl, n-butyl, isobutyl, 2-butyl, tert.-butyl, n-pentyl, neopentyl, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$ and —O—$CH_2F$;

a residue selected from the group consisting of naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—$Si(CH_3)_3$, —C≡C—$Si(C_2H_5)_3$, —$CH_2$—O—$CH_3$, —$CH_2$—O—$C_2H_5$, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, —$N(CH_3)_2$, —$N(C_2H_5)_2$, —NH—$CH_3$, —NH—$C_2H_5$, —$CH_2$—O—C(=O)-phenyl, —NH—S(=O)$_2$—$CH_3$, —C(=O)—O—$CH_3$, —C(=O)—O—$C_2H_5$, —C(=O)—O—$C(CH_3)_3$, —C(=O)—H, —C(=O)—$CH_3$, —C(=O)—NH—$CH_3$, —C(=O)—$N(CH_3)_2$, —C(=O)—O—$CH(CH_3)_2$, —C(=O)—O—$(CH_2)_3$—$CH_3$, —C(=O)—NH—$C(CH_3)_3$, —C(=O)—$N(C_2H_5)_2$, —C(=O)—NH-phenyl, —C(=O)—$N(CH_3)$-phenyl, —C(=O)—$N(C_2H_5)$-phenyl, —S(=O)—$NH_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —$NO_2$, —OH, —SH, —$NH_2$ methyl, ethyl, n-propyl, isopropyl, n-butyl, isobutyl, 2-butyl, tert.-butyl, n-pentyl, neopentyl, ethenyl, allyl, ethynyl, propynyl, —O—$CH_3$, —O—$C_2H_5$, —O—$C_3H_7$, —O—$C(CH_3)_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$; or —NH—C(=O)—$R^5$;

$R^2$ denotes
H;
$C_{1-6}$ alkyl, $C_{2-6}$ alkenyl or $C_{2-6}$ alkynyl, which is in each case unsubstituted or optionally substituted with 1, 2, 3, 4 or 5 substituents independently selected from the group consisting of F, Cl, Br, I, —$NO_2$, —CN, —OH, —SH, —$NH_2$, —$N(CH_3)_2$, —$N(C_2H_5)_2$, —$N(CH_3)(C_2H_5)$, —C(=O)—OH, —C(=O)—O—$CH_3$, —C(=O)—O—$C_2H_5$, —C(=O)—O—$CH_2$-phenyl, —C(=O)—NH-naphthyl, —$N(CH_3)$-phenyl, —$N(C_2H_5)$-phenyl, —$N(C_2H_5)$-(m-toluyl), —$N(C_2H_5)$-(p-toluyl), —$N(CH_3)$-(p-toluyl) and —NH—C(=O)—O—$C(CH_3)_3$; or a residue selected from the group consisting of phenyl and naphthyl, which in each case may optionally be attached via a $C_{1-3}$ alkylene, $C_{2-3}$ alkenylene or $C_{2-3}$ alkynylene group and/or is in each case unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —NH$_2$, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(═O)-phenyl, —NH—S(═O)$_2$—CH$_3$, —C(═O)—H, —C(═O)—CH$_3$, —C(═O)—C$_2$H$_5$, —NH—C(═O)—CH$_3$, —NH—C(═O)—C$_2$H$_5$, —O—C(═O)-phenyl, —C(═O)—NH$_2$, —C(═O)—NH—CH$_3$, —C(═O)—NH—C$_2$H$_5$, —C(═O)—NH—C(CH$_3$)$_3$, —C(═O)—N(C$_2$H$_5$)$_2$, —S(═O)—NH$_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F; or $R^1$ and $R^2$, together with the nitrogen atom to which they are bound, form a heterocycle selected from the group consisting of imidazolidinyl, [1,3,4,9]-tetrahydro-[b]-carbolinyl, piperidinyl, morpholinyl, thiomorpholinyl, pyrrolidinyl, azepanyl, diazepanyl and (1,4)-dioxo-8-aza-spiro[4.5]decyl, which in each case may be unsubstituted or optionally substituted with 1 or 2 $R^6$ residues;

$R^3$ denotes $C_{1-6}$ alkyl, $C_{2-6}$ alkenyl or —$C_{2-6}$ alkynyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(═O)—OH, —C(═O)—O—CH$_3$, —C(═O)—O—C$_2$H$_5$, —C(═O)—O—C(CH$_3$)$_3$, —C(═O)—O—CH$_2$-phenyl, —N(C$_2$H$_5$)-(p-toluyl), —N(CH$_3$)-(p-toluyl) and —NH—C(═O)—O—C(CH$_3$)$_3$; or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which is in each case attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —CH$_2$—O—CH$_3$, —CH$_2$—O—C$_2$H$_5$, —NH$_2$, —C(═O)—OH, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CH$_2$F, —N(CH$_3$)$_2$, —N(C$_2$H$_5$)$_2$, —NH—CH$_3$, —NH—C$_2$H$_5$, —C(═O)—H, —C(═O)—CH$_3$, —C(═O)—C$_2$H$_5$, —C(═O)—NH$_2$, —C(═O)—NH—CH$_3$ and —C(═O)—N(CH$_3$)$_2$;

$R^4$ denotes phenyl, which is in each case unsubstituted or substituted with 1, 2, 3, 4 or 5 substituents independently selected from the group consisting of F, Cl, Br, I, —CN, —CH$_2$—CN, —OH, —SH, —NH$_2$, —C(═O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, —S(═O)$_2$—C$_{1-5}$-alkyl, —S(═O)—C$_{1-5}$-alkyl, —NH—C$_{1-5}$-alkyl, —N(C$_{1-5}$-alkyl)$_2$, —C(═O)—O—C$_{1-5}$-alkyl, —C(═O)—H, —C(═O)—C$_{1-5}$-alkyl, —CH$_2$—O—C(═O)-phenyl, —O—C(═O)-phenyl, —NH—S(═O)$_2$—C$_{1-5}$-alkyl, —NH—C(═O)—C$_{1-5}$-alkyl, —C(═O)—NH$_2$, —C(═O)—NH—C$_{1-5}$-alkyl, —C(═O)—N(C$_{1-5}$-alkyl)$_2$, —S(═O)$_2$—NH$_2$, —S(═O)$_2$—NH—C$_{1-5}$-alkyl, —S(═O)$_2$—N(C$_{1-5}$-alkyl)$_2$, —S(═O)$_2$—NH-phenyl, [1,2,3]-thiadiazolyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, wherein the cyclic substituents or the cyclic residues of these substituents themselves may in each case be unsubstituted or optionally substituted with 1, 2, 3, 4, or 5 substituents independently selected from the group consisting of F, Cl, Br, I, —CN, —NO$_2$, —OH, —SH, —NH$_2$, —C(═O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F; or a residue selected from the group consisting of naphthyl, benzimidazolyl, triazinyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, isoindolyl, benzo[b]furanyl, benzo[b]thiophenyl, benzo[d]thiazolyl, benzodiazolyl, benzotriazolyl, benzoxazolyl, benzisoxazolyl, thiadiazolyl, oxadiazolyl, pyridazinyl, quinoxalinyl, quinazolinyl, quinolinyl, naphthridinyl and isoquinolinyl, which is in each case unsubstituted or optionally substituted with 1, 2, 3, 4 or 5 substituents independently selected from the group consisting of F, Cl, Br, I, —CN, —CH$_2$—CN, —NO$_2$, —OH, —SH, —NH$_2$, —C(═O)—OH, —C$_{1-5}$-alkyl, —(CH$_2$)—O—C$_{1-5}$- alkyl, —$C_{2-5}$-alkynyl, —C≡C—Si(CH$_3$)$_3$, —C≡C—Si(C$_2$H$_5$)$_3$, —S—$C_{1-5}$-alkyl, —S-phenyl, —S—CH$_2$-phenyl, —O—$C_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—$C_{1-5}$-alkyl, —S(=O)—$C_{1-5}$-alkyl, —NH—$C_{1-5}$-alkyl, —N($C_{1-5}$-alkyl)$_2$, —C(=O)—O—$C_{1-5}$-alkyl, —C(=O)—H, —C(=O)—$C_{1-5}$-alkyl, —CH$_2$-O—C(=O)-phenyl, —O—C(=O)-phenyl, —NH—S(=O)$_2$—$C_{1-5}$-alkyl, —NH—C(=O)—$C_{1-5}$-alkyl, —C(=O)—NH$_2$, —C(=O)—NH—$C_{1-5}$-alkyl, —C(=O)—N($C_{1-5}$-alkyl)$_2$, —S(=O)$_2$—NH$_2$, —S(=O)$_2$—NH—$C_{1-5}$-alkyl, —S(=O)$_2$—N($C_{1-5}$-alkyl)$_2$, —S(=O)$_2$—NH-phenyl, [1,2,3]-thiadiazolyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —NO$_2$, —OH, —SH, —NH$_2$, —C(=O)—OH, —$C_{1-5}$-alkyl, —(CH$_2$)—O—$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —S—$C_{1-5}$-alkyl, —S-phenyl, —S—CH$_2$-phenyl, —O—$C_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

$R^5$ denotes unsubstituted or at least monosubstituted alkyl, alkenyl or alkynyl; unsubstituted or at least monosubstituted heteroalkyl, heteroalkenyl or heteroalkynyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

$R^6$ denotes —OH; F; Cl; Br; I; —SH; —NO$_2$; —NH$_2$; —NH—C(=O)—O—$R^7$; —C(=O)—O—$R^8$; —C(=O)—$R^9$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl; and $R^7$, $R^8$ and $R^9$ each independently denote unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

or a pharmaceutically acceptable salt thereof.

2. A compound as claimed in claim 1, wherein said compound is present in the form of an isolated stereoisomer.

3. A compound as claimed in claim 1, wherein said compound is present in the form of a mixture of stereoisomers in any mixing ratio.

4. A compound as claimed in claim 3, wherein said mixture is a racemic mixture.

5. A compound as claimed in claim 1, wherein:

$R^1$ denotes $C_{1-6}$ alkyl, $C_{2-6}$ alkenyl or —$C_{2-6}$ alkynyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluyl), —N(C$_2$H$_5$)-(p-toluyl), —N(CH$_3$)-(p-toluyl) and —NH—C(=O)—O—C(CH$_3$)$_3$;

2- to 6-membered heteroalkyl, which is in each case unsubstituted or optionally substituted with 1, 2, 3, 4 or 5 substituents independently selected from the group consisting of F, Cl, Br, I, —NO$_2$, —CN, —OH, —SH and —NH$_2$ and in each case 1 or 2 heteroatom(s) independently selected from the group consisting of oxygen, sulfur and nitrogen (NH) as chain link(s);

$C_{3-7}$ cycloalkyl, $C_{5-6}$ cycloalkenyl, 5- to 7-membered heterocycloalkyl, 5- to 7-membered heterocycloalkenyl, (1,2,3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1.4]dioxinyl or benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH₂-phenyl, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃, —S—C₂H₅, —C(=O)—CH₃, —C(=O)—C₂H₅, —C(=O)—C(CH₃)₃, —C(=O)—NH—CH₃, —C(=O)—NH—C₂H₅, —CH₂-naphthyl, benzyl and phenyl and/or in each case may be attached via an unsubstituted C₁₋₃ alkylene, C₂₋₃ alkenylene or C₂₋₃ alkynylene group and/or in each case may comprise 1 or 2 heteroatom(s) independently selected from the group consisting of oxygen, sulfur and nitrogen (NH) as ring member(s);

phenyl, which in each case may optionally be attached via a C₁₋₃ alkylene, C₂₋₃ alkenylene or C₂₋₃ alkynylene group, which is in each case unsubstituted or substituted with 1 or 2 substituents selected from the group consisting of F, —C(=O)—O—CH₃ and —C(=O)—O—C₂H₅, or via a —CH₂—CH₂—O—, —CH₂—O— or —CH₂—CH₂—CH₂—O— group and/or is in each case unsubstituted or substituted with 1, 2, 3, 4 or 5 substituents independently selected from the group consisting of F, Cl, Br, I, —CN, —CH₂—CN, —NO₂, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH₃)₃, —C≡C—Si(C₂H₅)₃, —CH₂—O—CH₃, —CH₂—O—C₂H₅, —, —NH₂, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂, —S—CH₂F, —S(=O)₂-phenyl, pyrazolyl, —N(CH₃)₂, —N(C₂H₅)₂, —NH—CH₃, —NH—C₂H₅, —NH—C₂H₅, —CH₂—O—C(=O)-phenyl, —NH—S(=O)₂—CH₃, —C(=O)—H, —C(=O)—CH₃, —C(=O)—C₂H₅, —NH—C(=O)—CH₃, —NH—C(=O)—C₂H₅, —C(=O)—NH—C(CH₃)₃, —C(=O)—N(C₂H₅)₂, —S(=O)—NH₂, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO, —OH, —SH, —NH₂, methyl, ethyl, n-propyl, isopropyl, n-butyl, isobutyl, 2-butyl, tert.-butyl, n-pentyl, neopentyl, —O—CH₃, —O—C₂H₅, —O—C₃H₇, —O—C(CH₃)₃, —CF₃, —CHF₂, —CH₂F, —O—CF₃, —O—CHF₂ and —O—CH₂F;

a residue selected from the group consisting of naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a C₁₋₃ alkylene, C₂₋₃ alkenylene or C₂₋₃ unsubstituted or optionally substituted with 1, 2, 3, 4 or 5 substituents independently selected from the group consisting of F, Cl, Br, I, —CN, —CH₂—CN, —NO₂, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propenyl, —C≡C—Si(CH₃)₃, —C≡C—Si(C₂H₅)₃, —CH₂—O—CH₃, —CH₂—O—C₂H₅, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂—CH₂F, —O—CF₃, —O—CHF₂, —O—CH₂F, —C(=O)—CF₃, —S—CF₃, —S—CHF₂, —S—CH₂F, —S(=O)₂-phenyl, pyrazolyl, —N(CH₃)₂, —N(C₂H₅)₂, —NH—CH₃, —NH—C₂H₅, —CH₂—O—C(=O)-phenyl, —NH—S(=O)₂—CH₃, —C(=O)—O—CH₃, —C(=O)—O—C₂H₅, —C(=O)—O—C(CH₃)₃, —C(=O)—CH₃, —C(=O)—C₂H₅, —NH—C(=O)—CH₃, —NH—C(=O)—C₂H₅, —O—C(=O)-phenyl, —C(=O)—NH₂, —C(=O)—NH—CH₃, —C(=O)—N(CH₃)₂, —C(=O)—O—CH(CH₃)₂, —C(=O)—O—(CH₂)₃—CH₃, —C(=O)—O-phenyl, —O—C(=O)—CH₃, —O—C(=O)—C₂H₅, —C(=O)—NH—C₂H₅, —C(=O)—NH—C(CH₃)₃, —C(=O)—N(C₂H₅)₂, —C(=O)—NH-phenyl, —C(=O)—N(CH₃)-phenyl, —C(=O)—N(C₂H₅)-phenyl, —S(=O)—NH₂, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO₂, —OH, —SH, —NH₂, methyl, ethyl, n-propyl, isopropyl, n-butyl, isobutyl, 2-butyl, tert.-butyl, n-pentyl, neopentyl, ethenyl, allyl, ethynyl, propynyl, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂ and —S—CH₂F; or —NH—C(=O)—R⁵;

R² denotes
H
C₁₋₆ alkyl, C₂₋₆ alkenyl or C₂₋₆ alkynyl, which is in each case unsubstituted or optionally substituted with 1, 2, 3, 4 or 5 substituents independently selected from the group consisting of F, Cl, Br, I, —NO₂, —CN, —OH, —SH, —NH₂, —N(CH₃)₂, —N(C₂H₅)₂, —N(CH₃)(C₂H₅), —C(=O)—OH, —C(=O)—O—CH₃, —C(=O)—O—C₂H₅, —C(=O)—O—CH₂-phenyl, —C(=O)—NH-naphthyl, —N(CH₃)-phenyl, —N(C₂H₅)-phenyl, —N(C₂H₅)-(m-toluyl), —N(C₂H₅)-(p-toluyl), —N(CH₃)-(p-toluyl) and —NH—C(=O)—O—C(CH₃)₃; or a residue selected from the group consisting of phenyl and naphthyl, which in each case may optionally be attached via a C₁₋₃ alkylene, C₂₋₃ alkenylene or C₂₋₃ alkynylene group and/or is in each case unsubstituted or optionally substituted with 1, 2, 3, 4 or 5 substituents independently selected from the group consisting of F, Cl, Br, I, —CN, —CH₂—CN, —NO₂, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH₃)₃, —C≡C—Si(C₂H₅)₃, —CH₂—

O—CH$_3$, —CH$_2$—O—C$_2$H$_5$, —NH$_2$—S—CH$_3$, —S—C$_2$H$_5$, —S(=O)—CH$_3$, —S(=O)$_2$—CH$_3$, =S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—NH—C$_2$H$_5$, —C(=O)—NH—C(CH$_3$)$_3$, —C(=O)—N(C$_2$H$_5$)$_2$, —S(=O)—NH$_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F; or $R^1$ and $R^2$, together with the nitrogen atom to which they are bound, form a heterocycle selected from the group consisting of imidazolidinyl, [1,3,4,9]-tetrahydro-[b]-carbolinyl, piperidinyl, morpholinyl, thiomorpholinyl, pyrrolidinyl, azepanyl, diazepanyl and (1,4)-dioxo-8-aza-spiro[4.5]decyl, which in each case may be unsubstituted or optionally substituted with 1 or 2 $R^6$ residues;

$R^3$ denotes $C_{1-6}$ alkyl, $C_{2-6}$ alkenyl or —$C_{2-6}$ alkynyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$, —C(=O)—O—C(CH$_3$)$_3$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluyl), —N(C$_2$H$_5$)-(p-toluyl), —N(CH$_3$)-(p-toluyl) and —NH—C(=O)—O—C(CH$_3$)$_3$; or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which is in each case attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —CH$_2$—O—CH$_3$, —CH$_2$—O—C$_2$H$_5$, —NH$_2$—C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$—N(C$_2$H$_5$)$_2$—NH—CH$_3$, —NH—C$_2$H$_5$, —C(=O)—H, —C(=O)—CH$_3$, —C(=O)—C$_2$H$_5$, —C(=O)—NH$_2$, —C(=O)—NH—CH$_3$ and —C(=O)—N(CH$_3$)$_2$;

$R^4$ denotes phenyl, which is in each case unsubstituted or substituted with 1, 2, 3, 4 or 5 substituents independently selected from the group consisting of F, Cl, Br, I, —CN, —CH$_2$—CN, —OH, —SH, —NH$_2$, —C(=O)—OH, —$C_{1-5}$-alkyl, —(CH$_2$)—O—$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —S—$C_{1-5}$-alkyl, —S-phenyl, —S—CH$_2$-phenyl, —O—$C_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—$C_{1-5}$-alkyl, —S(=O)—$C_{1-5}$-alkyl, —NH—$C_{1-5}$-alkyl, —N($C_{1-5}$-alkyl)$_2$, —C(=O)—O—$C_{1-5}$-alkyl, —C(=O)—H, —C(=O)—$C_{1-5}$-alkyl, —CH$_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—NH$_2$, —C(=O)—NH—$C_{1-5}$-alkyl, —C(=O)—N($C_{1-5}$-alkyl)$_2$, —S(=O)$_2$—NH$_2$, —S(=O)$_2$—NH—$C_{1-5}$-alkyl, —S(=O)$_2$—N($C_{1-5}$-alkyl)$_2$, —S(=O)$_2$—NH-phenyl, [1,2,3]-thiadiazolyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —NO$_2$, —OH, —SH, —NH$_2$, —C(=O)—OH, —$C_{1-5}$-alkyl, —(CH$_2$)—O—$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —S—$C_{1-5}$-alkyl, —S-phenyl, —S—CH$_2$-phenyl, —O—$C_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F; or a residue selected from the group consisting of naphthyl, benzimidazolyl, triazinyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, isoindolyl, benzo[b]furanyl, benzo[b]thiophenyl, benzo[d]thiazolyl, benzodiazolyl, benzotriazolyl, benzoxazolyl, benzisoxazolyl, thiadiazolyl, oxadiazolyl, pyridazinyl, quinoxalinyl, quinazolinyl, quinolinyl, naphthridinyl and isoquinolinyl, which is in each case unsubstituted or optionally substituted with 1, 2, 3, 4 or 5 substituents independently selected from the group consisting of F, Cl, Br, I, —CN, —NO$_2$, —OH, —CH$_2$—CN, —SH, —NH$_2$, —C(=O)—OH, —$C_{1-5}$-alkyl, —(CH$_2$)—O—$C_{1-5}$-alkyl, —$C_{2-5}$-alkynyl, —C≡C—Si(CH$_3$)$_3$, —C≡C—Si(C$_2$H$_5$)$_3$, —S—$C_{1-5}$-alkyl, —S-phenyl, —S—CH$_2$-phenyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)₂—C₁₋₅-alkyl, —S(=O)—C₁₋₅-alkyl, —N(C₁₋₅-alkyl)₂, —C(=O)—O—C₁₋₅-alkyl, —C(=O)—H, —C(=O)—C₁₋₅-alkyl, —CH₂—O—C(=O)-phenyl, —O—C(=O)-phenyl, —NH—S(=O)₂—C₁₋₅-alkyl, —NH—C(=O)—C₁₋₅-alkyl, —C(=O)—NH₂, —C(=O)—NH—C₁₋₅-alkyl, —C(=O)—N(C₁₋₅-alkyl)₂, —S(=O)₂—NH₂, —S(=O)₂—NH—C₁₋₅-alkyl, —S(=O)₂—N(C₁₋₅-alkyl)₂, —S(=O)₂—NH-phenyl, [1,2,3]-thiadiazolyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —NO₂, —OH, —SH, —NH₂, —C(=O)—OH, —C₁₋₅-alkyl, —(CH₂)—O—C₁₋₅-alkyl, —C₂₋₅-alkenyl, —C₂₋₅-alkynyl, —C≡C—Si(CH₃)₃, —C≡C—Si(C₂H₅)₃, —S—C₁₋₅-alkyl, —S-phenyl, —S—CH₂-phenyl, —O—C₁₋₅-alkyl, —O-phenyl, —O—CH₂-phenyl, —CF₃, —CHF₂, —CH₂F, —O—CF₃, —O—CHF₂, —O—CH₂F, —C(=O)—CF₃, —S—CF₃, —S—CHF₂ and —S—CH₂F;

R⁵ denotes unsubstituted or at least monosubstituted alkyl, alkenyl or alkynyl; unsubstituted or at least monosubstituted heteroalkyl, heteroalkenyl or heteroalkynyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

R⁶ denotes —OH; F; Cl; Br; I; —SH; —NO₂; —NH₂; —NH—C(=O)—O—R⁷; —C(=O)—O—R⁸; —C(=O)—R⁹; denotes unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl; and R⁷, R⁸ and R⁹ each independently denote unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

wherein
the above-stated alkyl residues are in each case branched or straight-chain and comprise 1, 2, 3, 4, 5, 6, 7, 8, 9, 10, 11 or 12 carbon atoms as chain links;
the above-stated alkenyl residues are in each case branched or straight-chain and comprise 2, 3, 4, 5, 6, 7, 8, 9, 10, 11 or 12 carbon atoms as chain links;
the above-stated alkynyl residues are in each case branched or straight-chain and comprise 2, 3, 4, 5, 6, 7, 8, 9, 10, 11 or 12 carbon atoms as chain links;
the above-stated heteroalkyl residues, heteroalkenyl residues and heteroalkynyl residues are in each case 2-, 3-, 4-, 5-, 6-, 7-, 8-, 9-, 10-, 11- or 12-membered;
the above-stated heteroalkyl residues, heteroalkenyl residues and heteroalkynyl residues in each case optionally comprise 1, 2 or 3 heteroatom(s) independently selected from the group consisting of oxygen, sulfur and nitrogen as chain link(s);
the above-stated alkyl residues, alkenyl residues, alkynyl residues, heteroalkyl residues, heteroalkenyl residues and heteroalkynyl residues may be substituted in each case with optionally 1, 2, 3, 4 or 5 substituents independently selected from the group consisting of F, Cl, Br, I, —NO₂, —CN, —OH, —SH, —NH₂, —N(C₁₋₅-alkyl)₂, —N(C₁₋₅-alkyl)(phenyl), —N(C₁₋₅-alkyl)(CH₂-phenyl), —N(C₁₋₅-alkyl)(CH₂—CH₂-phenyl), —NH—C(=O)—O—C₁₋₅-alkyl, —C(=O)—H, —C(=O)—C₁₋₅-alkyl, —C(=O)-phenyl, —C(=S)—C₁₋₅-alkyl, —C(=S)-phenyl, —C(=O)—OH, —C(=O)—O—C₁₋₅-alkyl, —C(=O)—O-phenyl, —C(=O)—O—CH₂-phenyl, —C(=O)—NH₂, —C(=O)—NH—C₁₋₅-alkyl, —C(=O)—N(C₁₋₅-alkyl)₂, —C(=O)—NH-phenyl, —C(=O)—N(C₁₋₅-alkyl)-phenyl, —C(=O)—NH-naphthyl, —C(=O)-pyrrolidinyl, —C(=O)-piperidinyl, —S(=O)—C₁₋₅-alkyl, —S(=O)-phenyl, —S(=O)₂—C₁₋₅-alkyl, —S(=O)₂-phenyl, —S(=O)₂—NH₂ and —SO₃H, wherein the above-stated C₁₋₅ alkyl residues may in each case be linear or branched and the above-stated phenyl or naphthyl residues may in each case be unsubstituted or substituted with 1, 2, 3, 4 or 5, preferably with 1, 2 or 3, substituents independently selected from the group consisting of F, Cl, Br, I, —CN, —CF₃, —OH, —NH₂, —O—CF₃, —SH, —O—CH₃, —O—C₂H₅, —O—C₃H₇, methyl, ethyl, n-propyl, isopropyl, n-butyl, 2-butyl, isobutyl and tert.-butyl;
the above-stated cycloalkyl residues in each case comprise 3, 4, 5, 6, 7, 8 or 9 carbon atoms as ring members;

the above-stated cycloalkenyl residues in each case comprise 3, 4, 5, 6, 7, 8 or 9 carbon atoms as ring members;

the above-stated heterocycloalkyl residues are in each case 3-, 4-, 5-, 6-, 7-, 8- or 9-membered;

the above-stated heterocycloalkenyl residues are in each case 4-, 5-, 6-, 7-, 8- or 9-membered;

the above-stated heterocycloalkyl residues and heterocycloalkenyl residues in each case optionally comprise 1, 2 or 3 heteroatom(s) independently selected from the group consisting of oxygen, sulfur and nitrogen (NH) as ring member(s);

the above-stated cycloalkyl residues, heterocycloalkyl residues, cycloalkenyl residues or heterocycloalkenyl residues may be substituted in each case with optionally 1, 2, 3, 4 or 5 substituents independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, =C(=O)—O—C$_{1-5}$-alkyl, —C(=O)—CF$_3$, —S(=O)$_2$—C$_{1-5}$-alkyl, —S(=O)—C$_{1-5}$-alkyl, —S(=O)$_2$-phenyl, oxo (=O), thioxo (=S), —N(C$_{1-5}$-alkyl)$_2$, —N(H)(C$_{1-5}$-alkyl), —NO$_2$, —S—CF$_3$, —C(=O)—OH, —NH—S(=O)$_2$—C$_{1-5}$-alkyl, —NH—C(=O)—C$_{1-5}$-alkyl, —NH—C(=O)—O—C$_{1-5}$-alkyl, —NH—C(=O)—CF$_3$, —C(=O)—H, —C(=O)—C$_{1-5}$-alkyl, —C(=O)—NH$_2$, —C(=O)—N(C$_{1-5}$-alkyl)$_2$, —C(=O)—N(H)(C$_{1-5}$-alkyl); —(CH$_2$)-pyrrolidinyl, benzyl, phenethyl, naphthyl, —(CH$_2$)-naphthyl and phenyl, wherein the above-stated C$_{1-5}$ alkyl residues may in each case be linear or branched and the cyclic substituents or the cyclic residues of these substituents themselves may be in each case unsubstituted or substituted with 1, 2, 3, 4 or 5, preferably with 1, 2, 3 or 4, substituents independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl and —C(=O)—CF$_3$;

the above-stated alkylene residues are in each case branched or straight-chain and comprise 1, 2, 3, 4, 5, 6, 7, 8, 9, 10, 11 or 12 carbon atoms as chain links;

the above-stated alkenylene residues are in each case branched or straight-chain and comprise 2, 3, 4, 5, 6, 7, 8, 9, 10, 11 or 12 carbon atoms as chain links;

the above-stated alkynylene residues are in each case branched or straight-chain and comprise 2, 3, 4, 5, 6, 7, 8, 9, 10, 11 or 12 carbon atoms as chain links;

the above-stated heteroalkylene residues and heteroalkenylene residues are in each case 2-, 3-, 4-, 5-, 6-, 7-, 8-, 9-, 10-, 11- or 12-membered;

the above-stated heteroalkylene and heteroalkenylene groups may in each case optionally comprise 1, 2 or 3 heteroatom(s) independently selected from the group consisting of oxygen, nitrogen and sulfur (NH) as chain link(s);

the above-stated alkylene, alkenylene, alkynylene, heteroalkylene or heteroalkenylene groups may in each case be unsubstituted or optionally substituted with 1, 2, 3, 4 or 5 substituents independently selected from the group consisting of phenyl, F, Cl, Br, I, —NO$_2$, —CN, —OH, —O-phenyl, —O—CH$_2$-phenyl, —SH, —S-phenyl, —S—CH$_2$-phenyl, —NH$_2$, —N(C$_{1-5}$-alkyl)$_2$, —NH-phenyl, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated C$_{1-5}$ alkyl residues may in each case be linear or branched and the above-stated phenyl residues may be substituted with 1, 2, 3, 4 or 5 substituents independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

the above-stated aryl residues are mono- or bicyclic and comprise 6, 10 or 14 carbon atoms;

the above-stated heteroaryl residues are mono-, di- or tricyclic and 5-, 6-, 7-, 8-, 9-, 10-, 11-, 12-, 13- or 14-membered;

the above-stated heteroalkyl residues optionally comprise 1, 2, 3, 4 or 5 heteroatom(s) independently selected from the group consisting of oxygen, sulfur and nitrogen (NH) as ring member(s);

unless otherwise stated, the above-stated aryl residues and heteroaryl residues may optionally in each case be substituted with 1, 2, 3, 4 or 5 substituents independently selected from the group consisting of F, Cl, Br, I, —CN, —CH$_2$—CN, —NO$_2$, —OH, —SH, —NH$_2$, —C(=O)—OH, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, —N(C$_{1-5}$-alkyl)$_2$, —C(=O)—O-phenyl, —C(=O)—H; —CH$_2$—O—C(=O)-phenyl, —O—C(=O)—C$_{1-5}$-alkyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, —C(=O)—N(C$_{1-5}$-alkyl)(phenyl), —C(=O)—NH-phenyl, —S(=O)$_2$—NH$_2$, —S(=O)$_2$—NH—C$_{1-5}$-alkyl, —S(=O)$_2$—N(C$_{1-5}$-alkyl)$_2$, —S(=O)$_2$—NH-phenyl, [1,2,3]-thiadiazolyl, cyclopropyl, cyclobutyl, cyclopentyl, cyclohexyl, piperazinyl, pyrrolidinyl, piperidinyl, pyrazolyl, phenyl, furyl (furanyl), thiazolyl, thiadiazolyl, thiophenyl (thienyl), benzyl and phenethyl, wherein the above-stated C$_{1-5}$ alkyl residues may in each case be linear or branched and the cyclic substituents or the cyclic residues of these substituents themselves may in each case be unsubstituted or optionally substituted with 1, 2, 3, 4 or 5 substituents independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

the above-stated aryl residues, heteroaryl residues, cycloalkyl residue, heterocycloalkyl residue, cycloalkenyl residue or heterocyclalkenyl residue may be fused (anellated) with an unsubstituted or at least monosubstituted mono- or bicyclic ring system;

wherein a mono- or polycyclic ring system is taken to mean mono- or polycyclic hydrocarbon residues, which may be saturated, unsaturated or aromatic;

wherein the rings of the above-stated mono- or bicyclic ring systems are in each case 4-, 5- or 6-membered and may in each case optionally comprise 0, 1, 2, 3, 4 or 5 heteroatom(s) as ring member(s), which are independently selected from the group consisting of oxygen, nitrogen and sulfur;

wherein the above-stated mono- or bicyclic ring systems may in each case be optionally substituted with 1, 2, 3, 4 or 5 substituents independently selected from the group consisting of F, Cl, Br, I, —CN, —NO$_2$, —OH, —SH, —NH$_2$, oxo (=O), thioxo (=S), —C(=O)—OH, C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —(CH$_2$)—O—C$_{1-5}$-alkyl, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$-alkyl)(C$_{1-5}$-alkyl), —C(=O)—O—C$_{1-5}$-alkyl, —C(=O)—H, —C(=O)—C$_{1-5}$-alkyl, —CH$_2$-O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, pyrazolyl, phenyl, furyl (furanyl), thiadiazolyl, thiophenyl (thienyl) and benzyl, wherein the above-stated C$_{1-5}$ alkyl residues may in each case be linear or branched and the cyclic substituents or the cyclic residues of these substituents themselves may in each case be optionally substituted with 1, 2, 3, 4 or 5 substituents independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl and —C(=O)—CF$_3$; and wherein the above-stated cycloalkyl residues, heterocycloalkyl residues, cycloalkenyl residues or heterocyclalkenyl residues may, together with a further cycloalkyl residue, heterocycloalkyl residue, cycloalkenyl residue or heterocyclalkenyl residue, form a spirocyclic residue by way of a common carbon atom in the ring.

6. A compound as claimed in claim 1, wherein:
R$^4$ denotes
phenyl, which may be unsubstituted or substituted with 1, 2, 3, 4 or 5 substituents independently selected from the group consisting of F, Cl, Br, I, —CN, —CH$_2$—CN, —OH, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —S—CH$_3$, —S—C$_2$H$_5$, —S-phenyl, —S—CH$_2$-phenyl, —O—CH$_3$, —O—C$_2$H$_5$, —O—C$_3$H$_7$, —O—C(CH$_3$)$_3$, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —S(=O)$_2$—NH$_2$, —S(=O)$_2$—NH-phenyl, [1,2,3]-thiadiazolyl, cyclopropyl, cyclobutyl, cyclopentyl, cyclohexyl, phenyl, benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F; or a residue selected from the group consisting of thienyl, furyl, pyrrolyl, pyrazolyl, pyrazinyl, pyranyl, triazolyl, pyridinyl, imidazolyl, thiadiazolyl, oxadiazolyl and pyridazinyl, which is in each case unsubstituted or optionally substituted with 1, 2, 3, 4 or 5 substituents independently selected from the group consisting of F, Cl, Br, I, —CN, —NO$_2$, —OH, —CH$_2$—CN, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —S—CH$_3$, —S—C$_2$H$_5$, —S-phenyl, —S—CH$_2$-phenyl, —O—CH$_3$, —O—C$_2$H$_5$, —O—C$_3$H$_7$, —O—C(CH$_3$)$_3$, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —S(=O)$_2$—NH$_2$—NH$_2$, cyclopropyl, cyclobutyl, cyclopentyl, cyclohexyl, phenyl and benzyl, wherein the cyclic substituents or the cyclic residues of these substituents themselves may in each case be unsubstituted or optionally substituted with 1, 2, 3, 4, or 5 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

7. A compound as claimed in claim 1, wherein:

R$^5$ denotes a residue selected from the group consisting of phenyl, naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—H, —C(=O)—CH$_3$, —C(=O)—C$_2$H$_5$, —C(=O)—NH$_2$, —C(=O)—NH—CH$_3$ and —C(=O)—N(CH$_3$)$_2$.

8. A compound as claimed in claim 1, wherein:

R$^6$ denotes

—OH; F; Cl; Br; I; —SH; —NO$_2$; —NH$_2$; —NH—C(=O)—O—R$^7$; —C(=O)—O—R$^8$; —C(=O)—R$^9$;

C$_{1-6}$ alkyl, C$_{2-6}$ alkenyl or C$_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —C(=O)-pyrrolidinyl, —C(=O)—N(CH$_3$)-phenyl and —C(=O)—NH—CH(CH$_3$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$;

C$_{3-7}$ cycloalkyl, C$_{5-6}$ cycloalkenyl, 5- to 7-membered heterocycloalkyl or 5- to 7-membered heterocycloalkenyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl and/or in each case may be attached via an unsubstituted C$_{1-3}$ alkylene, C$_{2-3}$ alkenylene or C$_{2-3}$ alkynylene group and/or in each case may comprise 1 or 2 heteroatom(s) independently selected from the group consisting of oxygen, sulfur and nitrogen (NH) as ring member(s); or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl, thieno[2,3-d]pyrimidinyl and isoquinolinyl, which in each case optionally may be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—NH—C$_2$H$_5$, —C(=O)—NH—C(CH$_3$)$_3$, —C(=O)—N(C$_2$H$_5$)$_2$, cyclopropyl, cyclobutyl, cyclopentyl, cyclohexyl, phenyl, furyl (furanyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

9. A compound as claimed in claim 1, wherein:

R$^7$, R$^8$ and R$^9$ each independently denote

C$_{1-6}$ alkyl, C$_{2-6}$ alkenyl or C$_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$; or a residue selected from the group consisting of indolinyl, indanyl, (1,2,3,4)-tetrahydronaphthyl, (2,3)-dihydrobenzo[1.4] dioxinyl and benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl; or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —$NH_2$, —C(=O)—OH, —S—$CH_3$, —S—$C_2H_5$, —O—$CH_3$, —O—$C_2H_5$, —O—$C_3H_7$, —O—C$(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —N$(CH_3)_2$, —N$(C_2H_5)_2$, —NH—$CH_3$, —NH—$C_2H_5$, —C(=O)—O—$CH_3$, —C(=O)—O—$C_2H_5$, —C(=O)—O—C$(CH_3)_3$, —C(=O)—H, —C(=O)—$CH_3$, —C(=O)—$C_2H_5$, —NH—C(=O)—$CH_3$, —NH—C(=O)—$C_2H_5$, —C(=O)—$NH_2$, —C(=O)—NH—$CH_3$, —C(=O)—N$(CH_3)_2$, —C(=O)—O—CH$(CH_3)_2$, —C(=O)—O—$(CH_2)_3$—$CH_3$, —C(=O)—NH—$C_2H_5$, —C(=O)—NH—C$(CH_3)_3$, —C(=O)—N$(C_2H_5)_2$, cyclopropyl, cyclobutyl, cyclopentyl, cyclohexyl, phenyl, furyl and benzyl.

10. A compound as claimed in claim 1, wherein:
$R^1$ denotes
$C_{1-6}$ alkyl, $C_{2-6}$ alkenyl or —$C_{2-6}$ alkynyl, which in each case may be unsubstituted or optionally substituted with 1, 2, 3, 4 or 5 substituents independently selected from the group consisting of F, Cl, Br, I, —$NO_2$, —CN, —OH, —SH, —$NH_2$, —N$(CH_3)_2$, —N$(C_2H_5)_2$, —N$(CH_3)(C_2H_5)$, —C(=O)—OH, —C(=O)—O—$CH_3$, —C(=O)—O—$C_2H_5$, —C(=O)—O—$CH_2$-phenyl, —C(=O)—NH-naphthyl, —N$(CH_3)$-phenyl, —N$(C_2H_5)$-phenyl, —N$(C_2H_5)$-(m-toluyl), —N$(C_2H_5)$-(p-toluyl), —N$(CH_3)$-(p-toluyl) and —NH—C(=O)—O—C$(CH_3)_3$;
2- to 6-membered heteroalkyl, which is in each case unsubstituted or optionally substituted with 1, 2, 3 4 or 5 substituents independently selected from the group consisting of F, Cl, Br, I, —$NO_2$, —CN, —OH, —SH, and —$NH_2$ and in each case comprises 1 or 2 heteroatom(s) independently selected from the group consisting of oxygen, sulfur and nitrogen (NH) as a chain link(s);
$C_{3-7}$ cycloalkyl, $C_{5-6}$ cycloalkenyl, 5- to 7-membered heterocycloalkyl, 5- to 7-membered heterocycloalkenyl, (1,2,3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1.4]dioxinyl or benzo[1.3]dioxolyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—$CH_3$, —O—$C_2H_5$, —O—$C_3H_7$, —O-phenyl, —O—$CH_2$-phenyl, —$NH_2$, —N$(CH_3)_2$, —N$(C_2H_5)_2$, —NH—$CH_3$, —NH—$C_2H_5$, —$NO_2$, —$CF_3$, —O—$CF_3$, —S—$CF_3$, —SH, —S—$CH_3$, —S—$C_2H_5$, —C(=O)—$CH_3$, —C(=O)—$C_2H_5$, —C(=O)—C$(CH_3)_3$, —C(=O)—NH—$CH_3$, —C(=O)—NH—$C_2H_5$, —$CH_2$-naphthyl, benzyl and phenyl and/or in each case may be attached via an unsubstituted $C_{1-3}$ alkylene, $C_{2-3}$ alkenylene or $C_{2-3}$ alkynylene group and/or in each case may comprise 1 or 2 heteroatom(s) independently selected from the group consisting of oxygen, sulfur and nitrogen (NH) as ring member(s);
phenyl, which optionally may be attached via a $C_{1-3}$-alkylene, $C_{2-3}$-alkenylene or $C_{2-3}$-alkynylene group, and which in each case may be unsubstituted or substituted with 1 or 2 substituents selected from the group consisting of F, —C(=O)—O—$CH_3$ and —C(=O)—O—$C_2H_5$, or via a —$CH_2$—$CH_2$—O, —$CH_2$—O— or —$CH_2$—$CH_2$—$CH_2$—O group and/or is in each case unsubstituted or substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si$(CH_3)_3$, —C≡C—Si$(C_2H_5)_3$, —$CH_2$—O—$CH_3$, —$CH_2$—O—$C_2H_5$, —$NH_2$, —S—$CH_3$, —S—$C_2H_5$, —S(=O)—$CH_3$, —S$(=O)_2$—$CH_3$, —S(=O)—$C_2H_5$, —S$(=O)_2$—$C_2H_5$, —O—$CH_3$, —O—$C_2H_5$, —O—$C_3H_7$, —O—C$(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S$(=O)_2$-phenyl, pyrazolyl, —N$(CH_3)_2$, —N$(C_2H_5)_2$, —NH—$CH_3$, —NH—$C_2H_5$, —$CH_2$—O—C(=O)-phenyl, —NH—S$(=O)_2$—$CH_3$, —C(=O)—H, —C(=O)—$CH_3$, —C(=O)—$C_2H_5$, —NH—C(=O)—$CH_3$, —NH—C(=O)—$C_2H_5$, —O—C(=O)-phenyl, —C(=O)—$NH_2$, —C(=O)—NH—$CH_3$, —C(=O)—NH—$C_2H_5$, —C(=O)—NH—C$(CH_3)_3$, —C(=O)—N$(C_2H_5)_2$, —S(=O)—$NH_2$, [1,2,3]-thiadiazolyl, cyclopropyl, cyclobutyl, cyclopentyl, cyclohexyl, piperazinyl, pyrrolidinyl, piperidinyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —$NO_2$, —OH, —SH, —$NH_2$, methyl, ethyl, n-propyl, isopropyl, n-butyl, isobutyl, 2-butyl, tert.-butyl, n-pentyl, neopentyl, —O—$CH_3$, —O—$C_2H_5$, —O—$C_3H_7$, —O—C$(CH_3)_3$, —$CF_3$, —$CHF_2$, —$CH_2F$, —O—$CF_3$, —O—$CHF_2$ and —O—$CH_2F$;
a residue selected from the group consisting of naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—O-phenyl, —O—C(=O)—CH$_3$, —O—C(=O)—C$_2$H$_5$, —C(=O)—NH—C$_2$H$_5$, —C(=O)—NH—C(CH$_3$)$_3$, —C(=O)—N(C$_2$H$_5$)$_2$, —C(=O)—NH-phenyl, —C(=O)—N(CH$_3$)-phenyl, —C(=O)—N(C$_2$H$_5$)-phenyl, —S(=O)—NH$_2$, [1,2,3]-thiadiazolyl, cyclopropyl, cyclobutyl, cyclopentyl, cyclohexyl, piperazinyl, pyrrolidinyl, piperidinyl, phenyl, furyl, thiadiazolyl, thiophenyl and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, ethenyl, allyl, ethynyl, propynyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F; or —NH—C(=O)—R$^5$;

R$^2$ denotes
H;
C$_{1-6}$-alkyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluyl), —N(C$_2$H$_5$)-(p-toluyl), —N(CH$_3$)-(p-toluyl) and —NH—C(=O)—O—C(CH$_3$)$_3$; or
a residue selected from the group consisting of phenyl and naphthyl, which may in each case be attached via a C$_{1-3}$ alkylene, C$_{2-3}$ alkenylene or C$_{2-3}$ alkynylene group and/or is in each case unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —NH$_2$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$ and —NH—C$_2$H$_5$; or R$^1$ and R$^2$, together with the nitrogen atom to which they are bound, form a residue selected from the group consisting of

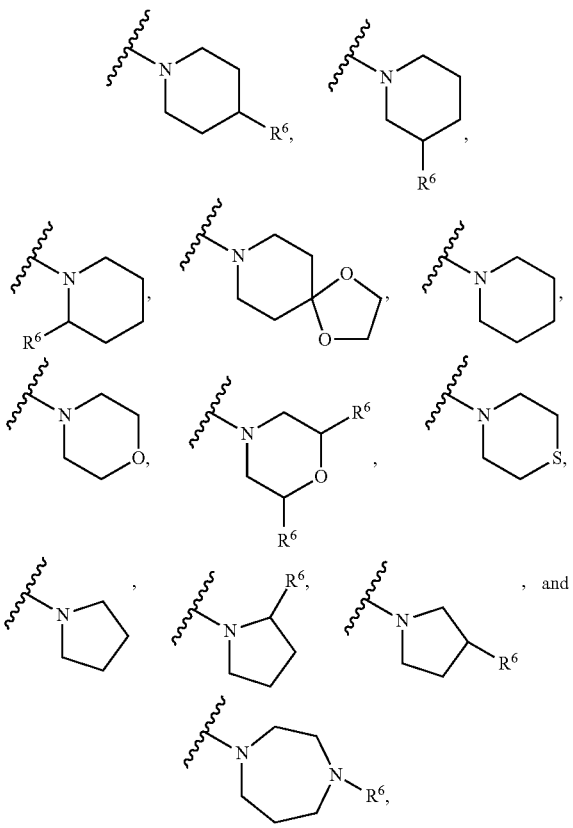

R$^3$ denotes
C$_{1-6}$ alkyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—C$_2$H$_5$ and —C(=O)—O—C(CH$_3$)$_3$; or
a residue selected from the group consisting of phenyl, isoxazolyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, pyridazinyl and isoquinolinyl, which is in each case attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —CH$_2$—O—CH$_3$, —CH$_2$—O—C$_2$H$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—H, —C(=O)—CH$_3$, —C(=O)—C$_2$H$_5$, —C(=O)—NH$_2$, —C(=O)—NH—CH$_3$ and —C(=O)—N(CH$_3$)$_2$;

R$^4$ denotes
phenyl, which may be unsubstituted or substituted with 1, 2, 3, 4 or 5 substituents independently selected from the group consisting of F, Cl, Br, I, —CN, —CH$_2$—CN, —OH, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —S—CH$_3$, —S—C$_2$H$_5$, —S-phenyl, —S—CH$_2$-phenyl, —O—CH$_3$, —O—C$_2$H$_5$, —O—C$_3$H$_7$, —O—C(CH$_3$)$_3$, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —S(=O)$_2$—NH$_2$, —S(=O)$_2$—NH-phenyl, [1,2,3]-thiadiazolyl, cyclopropyl, cyclobutyl, cyclopentyl, cyclohexyl, phenyl, benzyl and phenethyl, wherein the cyclic substituents or the cyclic residues of these substituents may themselves in each case be unsubstituted or optionally substituted with 1, 2, 3, 4 or 5 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F; or
a residue selected from the group consisting of thienyl, furyl, pyrrolyl, pyrazolyl, pyrazinyl, pyranyl, triazolyl, pyridinyl, imidazolyl, thiadiazolyl, oxadiazolyl and pyridazinyl, which is in each case unsubstituted or optionally substituted with 1, 2, 3, 4 or 5 substituents independently selected from the group consisting of F, Cl, Br, I, —CN, —NO$_2$, —OH, —CH$_2$—CN, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —S—CH$_3$, —S—C$_2$H$_5$, —S-phenyl, —S—CH$_2$-phenyl, —O—CH$_3$, —O—C$_2$H$_5$, —O—C$_3$H$_7$, —O—C(CH$_3$)$_3$, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —S(=O)$_2$—NH$_2$, cyclopropyl, cyclobutyl, cyclopentyl, cyclohexyl, phenyl and benzyl, wherein the cyclic substituents or the cyclic residues of these substituents themselves may in each case be unsubstituted or optionally substituted with 1, 2, 3, 4, or 5 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

R$^5$ denotes a residue selected from the group consisting of phenyl, naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a C$_{1-3}$ alkylene, C$_{2-3}$ alkenylene or C$_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$ and —NH—C$_2$H$_5$;

R$^6$ denotes
—OH; F; Cl; Br; I; —SH; —NO$_2$; —NH$_2$; —NH—C(=O)—O—R$^7$; —C(=O)—O—R$^{8-}$;
—C(=O)—R$^9$;
C$_{1-6}$ alkyl, C$_{2-6}$ alkenyl or C$_{2-6}$ alkynyl, which in each case may be unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —C(=O)-pyrrolidinyl, —C(=O)—N(CH$_3$)-phenyl and —C(=O)—NH—CH(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$;
C$_{3-7}$ cycloalkyl, C$_{5-6}$ cycloalkenyl, 5- to 7-membered heterocycloalkyl or 5- to 7-membered heterocycloalkenyl, which is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl and/or in each case may be attached via an unsubstituted C$_{1-3}$ alkylene, C$_{2-3}$ alkenylene or C$_{2-3}$ alkynylene group and/or in each case may comprise 1 or 2 heteroatom(s) independently selected from the group consisting of oxygen, sulfur and nitrogen (NH) as ring member(s); or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl, thieno[2,3-d]pyrimidinyl and isoquinolinyl, which in each case may optionally be attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—NH—C$_2$H$_5$, —C(=O)—NH—C(CH$_3$)$_3$, —C(=O)—N(C$_2$H$_5$)$_2$, cyclopropyl, cyclobutyl, cyclopentyl, cyclohexyl, phenyl, furyl (furanyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, —OH, —SH, —NH$_2$, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F; and $R^7$, $R^8$ and $R^9$ each independently denote $C_{1-6}$ alkyl, $C_{2-6}$ alkenyl or $C_{2-6}$ alkynyl, which is in each case unsubstituted or optionally substituted with 1, 2, 3, 4 or 5 substituents independently selected from the group consisting of F, Cl, Br, I, —NO$_2$, —CN, —OH, —SH, —NH$_2$, —N(CH$_3$)$_2$, —N(C$_2$H$_5$)$_2$, —N(CH$_3$)(C$_2$H$_5$), —C(=O)—OH, —C(=O)—O—CH$_3$, —C(=O)—O—C$_2$H$_5$ and —C(=O)—O—C(CH$_3$)$_3$; or a residue selected from the group consisting of indolinyl, indanyl, (1,2,3,4)-tetrahydronaphthyl, (2,3)-dihydrobenzo[1.4]dioxinyl and benzo[1.3]dioxolyl, which in each case may be unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —O-phenyl, —O—CH$_2$-phenyl, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl; or a residue selected from the group consisting of phenyl, naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a $C_{1-3}$ alkylene, $C_{2-3}$ alkenylene or $C_{2-3}$ alkynylene group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —NH—C(=O)—CH$_3$, —NH—C(=O)—C$_2$H$_5$, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—NH—C$_2$H$_5$, —C(=O)—NH—C(CH$_3$)$_3$, —C(=O)—N(C$_2$H$_5$)$_2$, cyclopropyl, cyclobutyl, cyclopentyl, cyclohexyl, phenyl, furyl (furanyl) and benzyl.

11. A compound as claimed in claim 1, wherein:

$R^1$ denotes an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or optionally substituted with 1, 2, 3, 4 or 5 substituents independently selected from the group consisting of F, Cl, Br, I, —CN, —OH, —SH, —NH$_2$, —N(CH$_3$)$_2$, —N(C$_2$H$_5$)$_2$, —N(CH$_3$)(C$_2$H$_5$), —C(=O)—O—CH$_3$, —C(=O)—O—C$_2$H$_5$, —C(=O)—O—CH$_2$-phenyl, —C(=O)—NH-naphthyl, —N(CH$_3$)-phenyl, —N(C$_2$H$_5$)-phenyl, —N(C$_2$H$_5$)-(m-toluyl), —N(C$_2$H$_5$)-(p-toluyl), —N(CH$_3$)-(p-toluyl) and —NH—C(=O)—O—C(CH$_3$)$_3$;

a heteroalkyl residue selected from the group consisting of —CH$_2$—O—CH$_3$, —CH$_2$—O—C$_2$H$_5$, —CH$_2$—CH$_2$—O—CH$_3$, —CH$_2$—CH$_2$—O—C$_2$H$_5$, —CH$_2$—CH$_2$—CH$_2$—O—CH$_3$ and —CH$_2$—CH$_2$—CH$_2$—O—C$_2$H$_5$, which in each case may be unsubstituted or optionally substituted with 1, 2, 3, 4 or 5 substituents independently selected from the group consisting of F, Cl and Br;

a residue selected from the group consisting of cyclopropyl, cyclobutyl, cyclopentyl, cyclohexyl, cycloheptyl, cyclohexenyl, cyclopentenyl, pyrrolidinyl, tetrahydrothiophenyl, tetrahydrofuranyl, piperidinyl, morpholinyl, piperazinyl, azepanyl, diazepanyl, (1,2, 3,4)-tetrahydroquinolinyl, (1,2,3,4)-tetrahydroisoquinolinyl, (2,3)-dihydro-1H-isoindolyl, indolinyl, indanyl, (1,2,3,4)-tetrahydronaphthyl, (2,3)-dihydrobenzo[1.4]dioxinyl and benzo[1.3]dioxolyl, which in each case may be unsubstituted or optionally substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert.-butyl, —OH, oxo, —O—CH$_3$, —O—C$_2$H$_5$, —O—C$_3$H$_7$, —O-phenyl, —O—CH$_2$-phenyl, —C(=O)—CH$_3$, —C(=O)—C$_2$H$_5$, —C(=O)—C(CH$_3$)$_3$, —C(=O)—NH—CH$_3$, —C(=O)—NH—C$_2$H$_5$, —CH$_2$-naphthyl, benzyl and phenyl and/or may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group;

phenyl, which may optionally be attached via a —CH$_2$—CH$_2$—O—, —CH$_2$—O—, —CH$_2$—CH$_2$—CH$_2$—O—, —CH[C(=O)—O—CH$_3$]—CH$_2$—, —CH[C(=O)—O—C$_2$H$_5$]—CH$_2$—, —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group and/or in each case may be unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —NH$_2$, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —N(CH$_3$)$_2$, —N(C$_2$H$_5$)$_2$, —NH—CH$_3$, —NH—C$_2$H$_5$, —NH—S(=O)$_2$—CH$_3$, —C(=O)—H, —C(=O)—CH$_3$, —C(=O)—C$_2$H$_5$, —NH—C(=O)—CH$_3$, —NH—C(=O)—C$_2$H$_5$, —S(=O)—NH$_2$, [1,2,3]-thiadiazolyl, cyclopropyl, cyclobutyl, cyclopentyl, cyclohexyl, phenyl, furyl (furanyl), thiadiazolyl, thiophenyl (thienyl) and benzyl, wherein the cyclic substituents or the cyclic residues of these substituents themselves may in each case be optionally substituted with 1, 2, 3, 4, or 5 substituents independently selected from the group consisting of F, Cl, Br, I, —CN, —NO$_2$, methyl, ethyl, n-propyl, isopropyl, n-butyl, isobutyl, 2-butyl, tert.-butyl, —O—CH$_3$, —O—C$_2$H$_5$, —O—C$_3$H$_7$ and —O—C(CH$_3$)$_3$;

a residue selected from the group consisting of naphthyl, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, indazolyl, quinoxalinyl, quinazolinyl, quinolinyl, naphthridinyl and isoquinolinyl, which may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$ group and/or is unsubstituted or optionally substituted with 1, 2, 3, 4 or 5 substituents independently selected from the group consisting of F, Cl, Br, I, —CN, —CH$_2$—CN, —NO$_2$, —OH, —SH, —O-phenyl, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —C(=O)—NH$_2$, —C(=O)—NH—CH$_3$, —C(=O)—N(CH$_3$)$_2$, —C(=O)—O—CH(CH$_3$)$_2$ and —C(=O)—O—(CH$_2$)$_3$—CH$_3$, or —NH—C(=O)—R$^5$;

R$^2$ denotes
H;
an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or
a residue selected from the group consisting of phenyl and naphthyl, which may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group and/or is in each case unsubstituted or optionally substituted with 1, 2, 3, 4 or 5 substituents independently selected from the group consisting of F, Cl, Br, I, —CN, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$ and —CH$_2$F; or R$^1$ and R$^2$, together with the nitrogen atom to which they are bound, form a residue selected from the group consisting of

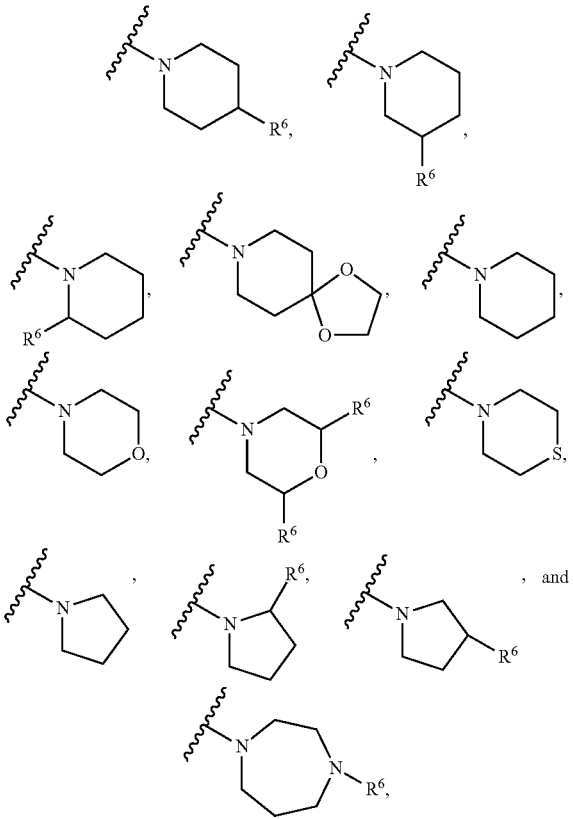

$R^3$ denotes
- an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or
- a phenyl residue, which in each case may optionally be attached via a —$CH_2$—, —$CH(CH_3)$—, —$CH_2$—$CH_2$—, —$CH(CH_3)$—$CH_2$—, —$CH_2$—$CH(CH_3)$— or —$CH_2$—$CH_2$—$CH_2$— group and/or in each case may be unsubstituted or optionally substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, allyl, ethynyl, propynyl, —$CH_2$—O—$CH_3$, —$CH_2$—O—$C_2H_5$, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$ and —O—$CH_2F$;

$R^4$ denotes
- phenyl which may be unsubstituted or optionally substituted with 1, 2, 3, 4 or 5 substituents independently selected from the group consisting of F, Cl, Br, I, —CN, —$CH_2$—CN, —OH, —SH, —$NH_2$, —C(=O)—OH, methyl, ethyl, n-propyl, isopropyl, n-butyl, isobutyl, 2-butyl, tert.-butyl, n-pentyl, —S—$CH_3$, —S—$C_2H_5$, —CO—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —$N(CH_3)_2$ and —NH—$CH_3$; or
- a residue selected from the group consisting of thienyl, furyl, pyrrolyl, pyrazolyl, pyrazinyl, pyranyl, triazolyl, pyridinyl, imidazolyl, thiadiazolyl, oxadiazolyl and pyridazinyl, which is in each case unsubstituted or optionally substituted with 1, 2, 3, 4 or 5 substituents independently selected from the group consisting of F, Cl, Br, I, —CN, —$NO_2$, —OH, —$CH_2$—CN, —SH, —$NH_2$, —C(=O)—OH, methyl, ethyl, n-propyl, isopropyl, n-butyl, isobutyl, 2-butyl, tert.-butyl, n-pentyl, neopentyl, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —$N(CH_3)_2$ and —NH—$CH_3$;

$R^5$ denotes a residue selected from the group consisting of phenyl and naphthyl, which is in each case unsubstituted or substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, n-pentyl, neopentyl, ethenyl, allyl, ethynyl, propynyl, —$NH_2$, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —$N(CH_3)_2$, —$N(C_2H_5)_2$, —NH—$CH_3$ and —NH—$C_2H_5$;

$R^6$ denotes
- —OH; F; Cl; Br; I; —SH; —$NO_2$; —$NH_2$; —NH—C(=O)—O—$R^7$; —C(=O)—O—$R^8$; —C(=O)—$R^9$;
- an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or optionally substituted with 1, 2, 3, 4 or 5 substituents independently selected from the group consisting of F, Cl, Br, I, —$NO_2$, —CN, —OH, —SH, —$NH_2$, —$N(CH_3)_2$, —$N(C_2H_5)_2$, —$N(CH_3)(C_2H_5)$, —C(=O)-pyrrolidinyl, —C(=O)—$N(CH_3)$-phenyl and —C(=O)—NH—$CH(CH_3)_2$, —C(=O)—OH, —C(=O)—O—$CH_3$, —C(=O)—O—$C_2H_5$ and —C(=O)—O—$C(CH_3)_3$;
- a residue selected from the group consisting of cyclopropyl, cyclobutyl, cyclopentyl, cyclohexyl, cycloheptyl, cyclohexenyl, cyclopentenyl, pyrrolidinyl, tetrahydrothiophenyl, tetrahydrofuranyl, piperidinyl, morpholinyl, piperazinyl, azepanyl and diazepanyl, which is in each case unsubstituted or optionally substituted with 1, 2, 3, 4 or 5 substituents independently selected from the group consisting of methyl, ethyl, n-propyl, isopropyl, n-butyl, 2-butyl, isobutyl, tert.-butyl, —OH, —O—$CH_3$, —O—$C_2H_5$, —O—$C_3H_7$, —O—$CF_3$, —C(=O)—$CH_3$, —C(=O)—$C_2H_5$, —C(=O)—$C(CH_3)_3$, —C(=O)—NH—$CH_3$ and —C(=O)—NH—$C_2H_5$ and/or may in each case be attached via a —$CH_2$—, —$CH(CH_3)$—, —$CH_2$—$CH_2$—, —$CH(CH_3)$—$CH_2$—, —$CH_2$—$CH(CH_3)$— or —$CH_2$—$CH_2$—$CH_2$— group; or
- a residue selected from the group consisting of phenyl, naphthyl, indolizinyl, benzimidazolyl, tetrazolyl, triazinyl, isoxazolyl, phthalazinyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl, pyridazinyl, thieno[2,3-d]pyrimidinyl and isoquinolinyl, which may in each case be attached via a $CH_2$—, —CH($CH_3$)—, —$CH_2$—$CH_2$—, —CH($CH_3$)—$CH_2$—, —$CH_2$—CH($CH_3$)— or —$CH_2$—$CH_2$—$CH_2$— group and/or is unsubstituted or optionally substituted with 1, 2, 3, 4 or 5 substituents independently selected from the group consisting of F, Cl, Br, I, —CN, —$CH_2$—CN, —$NO_2$, —OH, —SH, —O-phenyl, methyl, ethyl, n-propyl, isopropyl, n-butyl, isobutyl, 2-butyl, tert.-butyl, n-pentyl, neopentyl, ethenyl, —O—$CH_3$, —O—$C_2H_5$, —O—$C_3H_7$, —O—$C(CH_3)_3$, —$CF_3$, —$CHF_2$, —$CH_2F$, —O—$CF_3$, —O—$CHF_2$, —O—CHEF, —C(=O)—$CF_3$, —C(=O)—H, —C(=O)—$CH_3$ and —C(=O)—$C_2H_5$; and $R^7$, $R^8$ and $R^9$ each independently denote
- an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or optionally substituted with 1, 2, 3, 4 or 5 substituents independently selected from the group consisting of F, Cl, Br, I, —$NO_2$, —CN, —OH, —SH, —$NH_2$, —$N(CH_3)_2$, —$N(C_2H_5)_2$ and —$N(CH_3)(C_2H_5)$;
- a residue selected from the group consisting of indolinyl, indanyl, (1,2,3,4)-tetrahydronaphthyl, (2,3)-dihydrobenzo[1.4] dioxinyl and benzo[1.3]dioxolyl, which is in each case unsubstituted; or
- a residue selected from the group consisting of phenyl, naphthyl, isoxazolyl, thienyl, furyl, pyrrolyl, pyrazolyl, pyrazinyl, pyranyl, triazolyl, pyridinyl, imidazolyl, indolyl, isoindolyl, thiazolyl, thiadiazolyl, oxazolyl, oxadiazolyl, isoxazolyl and pyridazinyl, which may in each case be attached via a —$CH_2$—, —CH(CH₃)—, —CH₂—CH₂—, —CH(CH₃)—CH₂—, —CH₂—CH(CH₃)— or —CH₂—CH₂—CH₂— group and/or is in each case unsubstituted or optionally substituted with 1, 2, 3, 4 or 5 substituents independently selected from the group consisting of F, Cl, Br, I, —CN, —NO₂, —O-phenyl, methyl, ethyl, n-propyl, isopropyl, n-butyl, isobutyl, 2-butyl, tert.-butyl, n-pentyl, neopentyl, —S—CH₃, —S—C₂H₅, —O—CH₃, —O—C₂H₅, —O—C₃H₇, —O—C(CH₃)₃, —CF₃, —CHF₂, —CH₂F, —O—CF₃, —O—CHF₂ and —O—CH₂F.

12. A compound as claimed in claim 1, wherein:
R¹ denotes
an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or substituted with 1, 2 or 3 substituents independently selected from the group consisting of —CN, —OH, —N(CH₃)₂, —N(C₂H₅)₂, —C(=O)—O—CH₃, —C(=O)—O—C₂H₅, —C(=O)—O—CH₂-phenyl, —C(=O)—NH-naphthyl, —N(CH₃)-phenyl, —N(C₂H₅)-(m-toluyl) and —N(C₂H₅)-(p-toluyl);
a heteroalkyl residue selected from the group consisting of —CH₂—O—CH₃, —CH₂—O—C₂H₅, —CH₂—CH₂—O—CH₃, —CH₂—CH₂—O—C₂H₅, —CH₂—CH₂—CH₂—O—CH₃ and —CH₂—CH₂—CH₂—O—C₂H₅;
a residue selected from the group consisting of cyclopropyl, cyclobutyl, cyclopentyl, cyclohexyl, cycloheptyl, pyrrolidinyl, tetrahydrofuranyl, piperidinyl, morpholinyl, piperazinyl, azepanyl, dihydrofuran-2(3H)-only, indanyl and (1,2,3,4)-tetrahydronaphthyl, which is in each case unsubstituted or optionally substituted with 1, 2, 3, 4 or 5 substituents independently selected from the group consisting of methyl, ethyl, n-propyl, isopropyl, n-butyl, 2-butyl, isobutyl, tert.-butyl, —CH₂-naphthyl, —O-phenyl, —O—CH₂-phenyl, benzyl and phenyl and/or in each case via a —CH₂, —CH(CH₃)—, —CH₂—CH₂—, —CH(CH₃)—CH₂—, —CH₂—CH(CH₃)— or —CH₂—CH₂—CH₂— group;
phenyl, which may optionally be attached via a —CH₂—CH₂—O—, —CH₂—O—, —CH₂—CH₂—CH₂—O—, —CH[C(=O)—O—CH₃]—CH₂—, —CH[C(=O)—O—C₂H₅]—CH₂—, —CH₂—, —CH(CH₃)—, —CH₂—CH₂—, —CH(CH₃)—CH₂—, —CH₂—CH(CH₃)— or —CH₂—CH₂—CH₂— group and/or in each case may be unsubstituted or optionally substituted with 1, 2, 3, 4 or 5 substituents independently selected from the group consisting of F, Cl, Br, I, —CH₂—CN, methyl, ethyl, n-propyl, isopropyl, n-butyl, isobutyl, 2-butyl, tert.-butyl, n-pentyl, neopentyl, —O-phenyl, —O—CH₃, —O—C₂H₅, —O—C₃H₇, —O—C(CH₃)₃, —CF₃, —CHF₂, —CH₂F, —O—CF₃, —O—CHF₂, —O—CH₂F, —N(CH₃)₂, —N(C₂H₅)₂, —S(=O)—NH₂ and [1,2,3]-thiadiazolyl;
a residue selected from the group consisting of thienyl, furyl, pyrrolyl, pyrazolyl, pyridinyl, imidazolyl, indolyl and isoindolyl, which may in each case be attached via a —CH₂, —CH(CH₃)—, —CH₂—CH₂—, —CH(CH₃)—CH₂—, —CH₂—CH(CH₃)— or —CH₂—CH₂—CH₂ group and/or is unsubstituted or optionally substituted with 1, 2 or 3 substituents independently selected from the group consisting of —NO₂, —OH, methyl, ethyl, n-propyl, isopropyl, n-butyl, isobutyl, 2-butyl, tert.-butyl, n-pentyl, and neopentyl; or
—NH—C(=O)—R⁵;
R² denotes
H;
an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or
a residue selected from the group consisting of phenyl and naphthyl, which may in each case be attached via a —CH₂—, —CH(CH₃)—, —CH₂—CH₂—, —CH(CH₃)—CH₂—, —CH₂—CH(CH₃)— or —CH₂—CH₂—CH₂— group and/or in each case is unsubstituted or optionally substituted with 1, 2 or 3 substituents independently selected from the group consisting of —O—CH₃, —O—C₂H₅, —O—C₃H₇ and —O—C(CH₃)₃; or
R¹ and R², together with the nitrogen atom to which they are bound, form a residue selected from the group consisting of

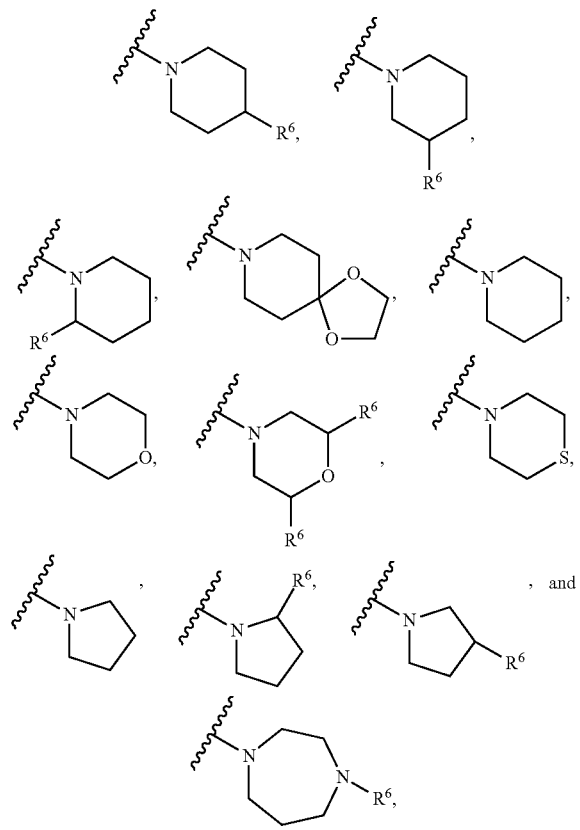

R³ denotes
an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted; or
a phenyl residue, which optionally may be attached via a —CH₂, —CH(CH₃)—, —CH₂—CH₂—, —CH(CH₃)—CH₂—, —CH₂—CH(CH₃)— or —CH₂—

CH$_2$—CH$_2$ group and/or may be unsubstituted or optionally substituted with 1, 2, 3, 4 or 5 substituents independently selected from the group consisting of F, Cl, Br, I, —CN, —CH$_2$—CN, —NO$_2$, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F;

R$^4$ denotes phenyl, which may be unsubstituted or substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, n-pentyl, —O—CH$_3$, —O—C$_2$H$_5$, —O—C$_3$H$_7$, —O—C(CH$_3$)$_3$, —O—CF$_3$, —O—CHF$_2$ and —O—CH$_2$F; or a residue selected from the group consisting of thienyl, furyl and pyrrolyl, which is in each case unsubstituted or optionally substituted with 1, 2, 3, 4 or 5 substituents independently selected from the group consisting of F, Cl, Br, I, methyl, ethyl, n-propyl, isopropyl, n-butyl, isobutyl, 2-butyl, —O—CH$_3$, —O—C$_2$H$_5$, —O—C$_3$H$_7$ and —O—C(CH$_3$)$_3$;

R$^5$ denotes a residue selected from the group consisting of phenyl and naphthyl, which in each case may be unsubstituted or substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, —NH$_2$, —O—CH$_3$, —O—C$_2$H$_5$, —O—C$_3$H$_7$, —O—C(CH$_3$)$_3$, —N(CH$_3$)$_2$, —N(C$_2$H$_5$)$_2$, —NH—CH$_3$ and —NH—C$_2$H$_5$;

R$^6$ denotes

—OH; —NH—C(=O)—O—R$^7$; —C(=O)—O—R$^8$; —C(=O)—R$^9$;

an alkyl residue selected from the group consisting of methyl, ethyl, n-propyl, isopropyl, n-butyl, 2-butyl, isobutyl, tert.-butyl, n-pentyl, sec.-pentyl, neopentyl, (3,3)-dimethylbutyl, 4-methyl-2-pentyl and n-hexyl, which is in each case unsubstituted or substituted with 1, 2 or 3 substituents independently selected from the group consisting of —OH, —N(CH$_3$)$_2$, —N(C$_2$H$_5$)$_2$, —C(=O)-pyrrolidinyl, —C(=O)—N(CH$_3$)-phenyl and —C(=O)—NH—CH(CH$_3$)$_2$;

a residue selected from the group consisting of cyclopropyl, cyclobutyl, cyclopentyl, cyclohexyl, cycloheptyl, pyrrolidinyl, piperidinyl and azepanyl, which is in each case unsubstituted and/or may in each case be attached via a —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group; or a residue selected from the group consisting of phenyl, naphthyl, thienyl, furyl, pyrazinyl, pyridinyl, pyridazinyl and thieno[2,3-d]pyrimidinyl, which may in each case be attached via a —CH$_2$, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$ group and/or in each case is unsubstituted or optionally substituted with 1, 2, 3, 4 or 5 substituents independently selected from the group consisting of F, Cl, Br, I, —CN, methyl, tert.-butyl, —O—CH$_3$, —O—C$_2$H$_5$, —CF$_3$, —C(=O)—CH$_3$ and —C(=O)—C$_2$H$_5$;

R$^7$, R$^8$ and R$^9$ each independently denote an alkyl residue selected from the group consisting of methyl, ethyl, n-propyl, isopropyl, n-butyl, 2-butyl, isobutyl, tert.-butyl, and n-pentyl, which is in each case unsubstituted;

a residue selected from the group consisting of (2,3)-dihydrobenzo[1.4]dioxinyl and benzo[1.3]dioxolyl, which is in each case unsubstituted; or a residue selected from the group consisting of phenyl, thienyl, furyl and pyrazinyl, which may in each case be attached via a —CH$_2$, —CH(CH$_3$)—, —CH(CH$_3$)—CH$_2$—, —CH$_2$—CH(CH$_3$)— or —CH$_2$—CH$_2$ group and/or in each case unsubstituted or optionally substituted with 1, 2, 3, 4 or 5 substituents independently selected from the group consisting of F, Cl, Br, I, methyl, ethyl, n-propyl, isopropyl, n-butyl, isobutyl, 2-butyl, tert.-butyl, n-pentyl, neopentyl, —O—CH$_3$, —O—C$_2$H$_5$, —O—C$_3$H$_7$ and —O—C(CH$_3$)$_3$.

13. A compound as claimed in claim 1, wherein:

R$^1$ denotes a residue selected from the group consisting of —CH$_2$—CH$_2$—N(C$_2$H$_5$)-(m-toluyl), —CH$_2$—CH$_2$—N(C$_2$H$_5$)-(p-toluyl), —CH$_2$—CH$_2$—CH$_2$—N(CH$_3$)-phenyl, —CH$_2$—CH$_2$—CH$_2$—N(CH$_3$)$_2$, —CH$_2$—CH$_2$—CH$_2$—N(C$_2$H$_5$)$_2$, —CH(CH$_3$)—CH$_2$—CH$_2$—CH(CH$_3$)$_2$, —CH$_2$—CH$_2$—CN, —CH$_2$—CH$_2$—OH, —CH$_2$—CH$_2$—N(CH$_3$)$_2$, —CH$_2$—CH$_2$—N(C$_2$H$_5$)$_2$, —CH$_2$—CH$_2$—C(CH$_3$)$_3$, n-pentyl, n-butyl, methyl, ethyl, n-propyl, —CH(CH$_3$)—C(=O)—O—CH$_2$-phenyl, —CH$_2$—C(=O)—O—CH$_2$-phenyl, —CH$_2$—CH$_2$—C(=O)—O—C$_2$H$_5$, —CH$_2$—C(=O)—NH-naphthyl and —CH$_2$—CH$_2$—CH$_2$—O—CH$_3$;

a residue selected from the group consisting of cyclopropyl, cyclobutyl, cyclopentyl, cyclohexyl, cycloheptyl, pyrrolidinyl, tetrahydrofuranyl, piperidinyl, morpholinyl, piperazinyl, azepanyl, dihydrofuran-2(3H)-only, indanyl and (1,2,3,4)-tetrahydro-naphthyl, which in each case may be unsubstituted or optionally substituted with 1, 2, 3, 4 or 5 substituents independently selected from the group consisting of methyl, ethyl, —CH$_2$-naphthyl, —O-phenyl, —O—CH$_2$-phenyl, and benzyl and/or may in each case be attached via a —CH$_2$, —CH$_2$—CH$_2$— or —CH$_2$—CH$_2$—CH$_2$ group;

phenyl, which optionally may be attached via a —CH$_2$—CH$_2$—O—, —CH[C(=O)—O—CH$_3$]—CH$_2$—, —CH[C(=O)—O—C$_2$H$_5$]—CH$_2$—, —CH$_2$—, —CH(CH$_3$)—, —CH$_2$—CH$_2$—, —CH(CH$_3$)—CH$_2$—, —CH$_2$—CH(CH$_3$)— or —CH$_2$—CH$_2$—CH$_2$— group and/or which may be unsubstituted or optionally substituted with 1, 2, 3, 4 or 5 substituents independently selected from the group consisting of F, Cl, Br, I, —CH$_2$—CN, methyl, ethyl, n-propyl, isopropyl, n-butyl, isobutyl, 2-butyl, tert.-butyl, —O-phenyl, —O—CH$_3$, —O—C$_2$H$_5$, —CF$_3$, —O—CF$_3$, —N(CH$_3$)$_2$, —N(C$_2$H$_5$)$_2$, —S(=O)—NH$_2$ and [1,2,3]-thiadiazolyl;

a residue selected from the group consisting of thienyl, furyl, pyridinyl, imidazolyl, indolyl and isoindolyl, which in each case optionally may be attached via a —CH$_2$, —CH$_2$—CH$_2$— or —CH$_2$—CH$_2$—CH$_2$ group and/or which may be unsubstituted or optionally substituted with 1, 2 or 3 substituents independently selected from the group consisting of —NO$_2$, —OH, methyl, ethyl and n-propyl; or

—NH—C(=O)—R$^5$;

R² denotes
  H;
  an alkyl residue selected from the group consisting of methyl, ethyl and n-propyl, which is in each case unsubstituted; or
  a residue selected from the group consisting of phenyl and naphthyl, which may in each case be attached via a —CH₂ group and/or may in each case be unsubstituted or substituted with 1, 2 or 3 substituents independently selected from the group consisting of —O—CH₃, —O—C₂H₅, —O—C₃H₇ and —O—C(CH₃)₃; or
R¹ and R², together with the nitrogen atom to which they are bound, form a residue selected from the group consisting of

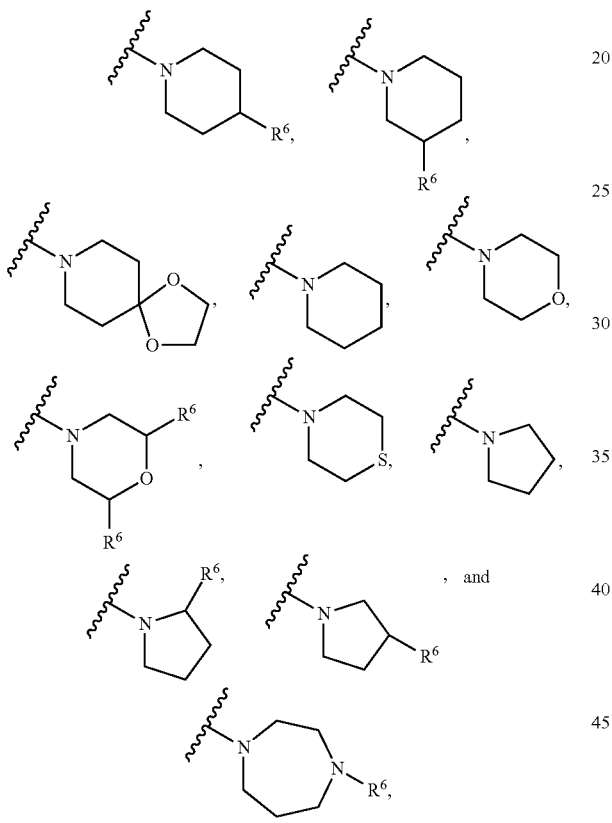

R³ denotes
  an alkyl residue selected from the group consisting of methyl, ethyl, n-propyl, isopropyl, n-butyl, 2-butyl, isobutyl and tert.-butyl, which is in each case unsubstituted; or
  a phenyl residue, which is in each case attached via a —CH₂ group and/or is in each case unsubstituted or optionally substituted with 1, 2, 3, 4 or 5 substituents independently selected from the group consisting of F, Cl, Br, methyl, ethyl, n-propyl, —O—CH₃, —O—C₂H₅, and —CF₃;
R⁴ denotes
  phenyl, which is in each case unsubstituted or substituted with 1, 2, 3, 4 or 5 substituents independently selected from the group consisting of F, Cl, Br, methyl, ethyl, n-propyl, —O—CH₃ and —O—C₂H₅; or
  a residue selected from the group consisting of thienyl, furyl and pyrrolyl, which is in each case unsubstituted;
R⁵ denotes a residue selected from the group consisting of phenyl and naphthyl, which in each case may be unsubstituted or substituted with 1, 2, 3, 4 or 5 substituents independently selected from the group consisting of F, Cl, Br, methyl, ethyl, —O—CH₃, —O—C₂H₅, —N(CH₃)₂, —N(C₂H₅)₂, —NH—CH₃ and —NH—C₂H₅;
R⁶ denotes
  —OH; —NH—C(=O)—O—R⁷; —C(=O)—O—R⁸; —C(=O)—R⁹;
  a residue selected from the group consisting of methyl, ethyl, n-propyl, isopropyl, n-butyl, —CH₃—CH(CH₃)₂, —CH₂—CH₂—OH, —CH₂—CH₂—N(CH₃)₂, —CH₂—CH₂—N(C₂H₅), —CH₂—C(=O)-pyrrolidinyl, —CH₂—C(=O)—NH—CH(CH₃)₂ and —CH₂—C(=O)—N(CH₃)-phenyl;
  a residue selected from the group consisting of cyclopropyl, cyclobutyl, cyclopentyl, cyclohexyl, cycloheptyl, pyrrolidinyl, piperidinyl and azepanyl, which is in each case unsubstituted and/or may in each case be attached via a —CH₂— group; or
  a residue selected from the group consisting of phenyl, naphthyl, thienyl, pyrazinyl, pyridinyl and thieno[2,3-d]pyrimidinyl, which may in each case be attached via a —CH₂—, —CH₂—CH₂— or —CH₂—CH₂—CH₂ group and/or is in each case unsubstituted or optionally substituted with 1, 2, 3, 4 or 5 substituents independently selected from the group consisting of F, Cl, Br, —CN, methyl, tert.-butyl, —O—CH₃, —O—C₂H₅, —CF₃, —C(=O)—CH₃ and —C(=O)—C₂H₅;
R⁷ denotes an alkyl residue selected from the group consisting of methyl, ethyl, n-propyl, isopropyl, n-butyl, 2-butyl, isobutyl, tert.-butyl, and n-pentyl, which is in each case unsubstituted;
R⁸ denotes an alkyl residue selected from the group consisting of methyl, ethyl, n-propyl, isopropyl, n-butyl, 2-butyl, isobutyl, tert.-butyl, and n-pentyl, which is in each case unsubstituted; or a phenyl or benzyl residue; and
R⁹ denotes
  a residue selected from the group consisting of (2,3)-dihydrobenzo[1.4]dioxinyl and benzo[1.3]dioxolyl, which is in each case unsubstituted; or
  a residue selected from the group consisting of phenyl, thienyl, furyl and pyrazinyl, which in each case may optionally be attached via a —CH₂—, —CH₂—CH₂— or —CH₂—CH₂—CH₂— group and/or in each case may be unsubstituted or optionally substituted with 1, 2, 3, 4 or 5 substituents independently selected from the group consisting of F, Cl, Br, methyl, ethyl, —O—CH₃ and —O—C₂H₅.

14. A compound as claimed in claim 1, selected from the group consisting of:
[1] 1-benzyl-4-methyl-3-p-tolyl-1H-pyrrole-2-carboxylic acid 4-[1,2,3]thiadiazol-4-ylbenzylamide,
[2] 3-furan-2-yl-1,4-dimethyl-1H-pyrrole-2-carboxylic acid 4-sulfamoylbenzylamide,
[3] 1-(4-fluorobenzyl)-3-furan-2-yl-4-methyl-1H-pyrrole-2-carboxylic acid 2,4-dimethoxybenzylamide,
[4] 1-butyl-4-methyl-3-p-tolyl-1H-pyrrole-2-carboxylic acid (2-pyridin-2-ylethyl)-amide,

[5] 1-(4-fluorobenzyl)-3-(4-methoxyphenyl)-4-methyl-1H-pyrrole-2-carboxylic acid [2-(5-hydroxy-1H-indol-3-yl)-ethyl]-amide,

[6] (1,4-dimethyl-3-p-tolyl-1H-pyrrole-2-yl)-(4-pyrrolidin-1-ylpiperidin-1-yl)-methanone,

[7] 1-benzyl-3-furan-2-yl-4-methyl-1H-pyrrole-2-carboxylic acid 4-bromo-2-fluorobenzylamide,

[9] 1,4-dimethyl-3-phenyl-1H-pyrrole-2-carboxylic acid (3-dimethylamino-propyl)-amide,

[10] 1,4-dimethyl-3-p-tolyl-1H-pyrrole-2-carboxylic acid (2-pyrrolidin-1-ylethyl)-amide,

[11] 1-(4-fluorobenzyl)-3-furan-2-yl-4-methyl-1H-pyrrole-2-carboxylic acid 4-dimethylaminobenzylamide,

[13] 1-benzyl-3-furan-2-yl-4-methyl-1H-pyrrole-2-carboxylic acid 2,5-difluorobenzylamide,

[14] 1-(2,6-dichlorobenzyl)-4-methyl-3-p-tolyl-1H-pyrrole-2-carboxylic acid 3,5-difluorobenzylamide,

[15] 1-(2-bromobenzyl)-3-(4-chlorophenyl)-4-methyl-1H-pyrrole-2-carboxylic acid (2-methylcyclohexyl)-amide,

[16] 1,4-dimethyl-3-p-tolyl-1H-pyrrole-2-carboxylic acid (3-morpholin-4-ylpropyl)-amide,

[17] 1-butyl-4-methyl-3-p-tolyl-1H-pyrrole-2-carboxylic acid (1,3-dimethylbutyl)-amide,

[19] 1-(2,6-dichlorobenzyl)-4-methyl-3-p-tolyl-1H-pyrrole-2-carboxylic acid methyl-(2-pyridin-2-ylethyl)-amide,

[20] 1,4-dimethyl-3-phenyl-1H-pyrrole-2-carboxylic acid (2-cyano-ethyl)-methylamide,

[21] 1-(2,6-dichlorobenzyl)-4-methyl-3-p-tolyl-1H-pyrrole-2-carboxylic acid (3-imidazol-1-ylpropyl)-amide,

[22] 1-(4-fluorobenzyl)-3-(4-methoxyphenyl)-4-methyl-1H-pyrrole-2-carboxylic acid (1,3-dimethylbutyl)-amide,

[23] 3-(4-methoxyphenyl)-1,4-dimethyl-1H-pyrrole-2-carboxylic acid 2-ethoxybenzylamide,

[25] 1-(4-fluorobenzyl)-3-(4-methoxyphenyl)-4-methyl-1H-pyrrole-2-carboxylic acid (2-dimethylamino-ethyl)-amide,

[26] 1-benzyl-4-methyl-3-phenyl-1H-pyrrole-2-carboxylic acid (pyridin-2-ylmethyl)-amide,

[27] 3-(4-chlorophenyl)-1-ethyl-4-methyl-1H-pyrrole-2-carboxylic acid [2-(4-chlorophenyl)-propyl]-amide,

[28] 3-(4-chlorophenyl)-1-(2-fluorobenzyl)-4-methyl-1H-pyrrole-2-carboxylic acid 3,5-difluorobenzylamide,

[29] 2-{[1-(4-fluorobenzyl)-3-(4-methoxyphenyl)-4-methyl-1H-pyrrole-2-carbonyl]-amino}-propionic acid benzyl ester,

[31] 3-furan-2-yl-1-(4-methoxybenzyl)-4-methyl-1H-pyrrole-2-carboxylic acid (3,3-dimethylbutyl)-amide,

[32] 3-(4-chlorophenyl)-1-isobutyl-4-methyl-1H-pyrrole-2-carboxylic acid 4-dimethylaminobenzylamide,

[33] 3-(4-chlorophenyl)-1-ethyl-4-methyl-1H-pyrrole-2-carboxylic acid (2-pyridin-2-ylethyl)-amide,

[34] 3-(4-chlorophenyl)-1-ethyl-4-methyl-1H-pyrrole-2-carboxylic acid 2,3-dimethoxybenzylamide,

[35] 1-(4-fluorobenzyl)-3-(4-methoxyphenyl)-4-methyl-1H-pyrrole-2-carboxylic acid (2-thiophen-2-ylethyl)-amide,

[37] 3-furan-2-yl-1-(4-methoxybenzyl)-4-methyl-1H-pyrrole-2-carboxylic acid (1,2,3,4-tetrahydro-naphthalen-1-yl)-amide,

[38] 3-furan-2-yl-4-methyl-1-(4-trifluoromethylbenzyl)-1H-pyrrole-2-carboxylic acid (2-pyrrolidin-1-ylethyl)-amide,

[39] {[1-(4-methoxybenzyl)-4-methyl-3-p-tolyl-1H-pyrrole-2-carbonyl]-methylamino}-acetic acid benzyl ester,

[40] 3-furan-2-yl-1-(4-methoxybenzyl)-4-methyl-1H-pyrrole-2-carboxylic acid [2-(1-methylpyrrolidin-2-yl)-ethyl]-amide,

[44] 1-benzyl-4-methyl-3-phenyl-1H-pyrrole-2-carboxylic acid 3-methoxybenzylamide,

[47] 1-(4-fluorobenzyl)-3-(4-methoxyphenyl)-4-methyl-1H-pyrrole-2-carboxylic acid [2-(4-ethoxyphenyl)-ethyl]-amide,

[48] [1-(2,6-dichlorobenzyl)-4-methyl-3-p-tolyl-1H-pyrrol-2-yl]-(4-hydroxypiperidin-1-yl)-methanone,

[50] 1-(4-fluorobenzyl)-3-furan-2-yl-4-methyl-1H-pyrrole-2-carboxylic acid (2-morpholin-4-ylethyl)-amide,

[51] 1-benzyl-3-(4-chlorophenyl)-4-methyl-1H-pyrrole-2-carboxylic acid [2-(4-fluorophenyl)-ethyl]-amide,

[53] 3-(4-methoxyphenyl)-1,4-dimethyl-1H-pyrrole-2-carboxylic acid (3-imidazol-1-ylpropyl)-amide,

[54] 1-(4-fluorobenzyl)-3-(4-methoxyphenyl)-4-methyl-1H-pyrrole-2-carboxylic acid [2-(3-trifluoromethylphenyl)-ethyl]-amide,

[56] 3-(4-chlorophenyl)-1-isobutyl-4-methyl-1H-pyrrole-2-carboxylic acid 3-fluoro-5-trifluoromethylbenzylamide,

[58] 3-(4-chlorophenyl)-1-(2-fluorobenzyl)-4-methyl-1H-pyrrole-2-carboxylic acid (3-imidazol-1-ylpropyl)-amide,

[60] 1-benzyl-3-furan-2-yl-4-methyl-1H-pyrrole-2-carboxylic acid [2-(4-bromophenyl)-ethyl]-amide,

[62] 1-benzyl-4-methyl-3-phenyl-1H-pyrrole-2-carboxylic acid [2-(4-methoxyphenoxy)-ethyl]-amide,

[63] 1-(4-fluorobenzyl)-3-furan-2-yl-4-methyl-1H-pyrrole-2-carboxylic acid (3-dimethylamino-propyl)-amide,

[64] [1-(4-fluorobenzyl)-3-(4-methoxyphenyl)-4-methyl-1H-pyrrol-2-yl]-(2-pyrrolidin-1-ylmethylpyrrolidin-1-yl)-methanone,

[65] 3-(4-chlorophenyl)-1-isobutyl-4-methyl-1H-pyrrole-2-carboxylic acid (3-diethylamino-propyl)-amide,

[67] 3-(4-methoxyphenyl)-1,4-dimethyl-1H-pyrrole-2-carboxylic acid pentylamide,

[73] 3-(4-chlorophenyl)-1-(2-fluorobenzyl)-4-methyl-1H-pyrrole-2-carboxylic acid 2,4-dimethoxybenzylamide,

[74] 1-benzyl-4-methyl-3-p-tolyl-1H-pyrrole-2-carboxylic acid (2-pyrrolidin-1-ylethyl)-amide,

[76] 3-(4-methoxyphenyl)-1,4-dimethyl-1H-pyrrole-2-carboxylic acid 2,4-dimethoxybenzylamide,

[77] 1-benzyl-4-methyl-3-phenyl-1H-pyrrole-2-carboxylic acid (2-pyrrolidin-1-ylethyl)-amide,

[78] 3-(4-chlorophenyl)-1,4-dimethyl-1H-pyrrole-2-carboxylic acid [3-(2-methylpiperidin-1-yl)-propyl]-amide,

[79] 1-(4-fluorobenzyl)-3-furan-2-yl-4-methyl-1H-pyrrole-2-carboxylic acid cyclohexylamide,

[80] 3-furan-2-yl-1,4-dimethyl-1H-pyrrole-2-carboxylic acid 4-fluoro-2-trifluoromethylbenzylamide,

[81] 1-benzyl-3-furan-2-yl-4-methyl-1H-pyrrole-2-carboxylic acid (1-naphthalen-2-ylethyl)-amide,

[82] 3-(4-chlorophenyl)-1-ethyl-4-methyl-1H-pyrrole-2-carboxylic acid (furan-2-ylmethyl)-amide,

[83] 1-benzyl-4-methyl-3-phenyl-1H-pyrrole-2-carboxylic acid (3-dimethylamino-propyl)-methylamide,

[85] 1-(4-methoxybenzyl)-4-methyl-3-p-tolyl-1H-pyrrole-2-carboxylic acid (thiophen-2-ylmethyl)-amide,

[86] 4-methyl-1-(4-methylbenzyl)-3-p-tolyl-1H-pyrrole-2-carboxylic acid phenethylamide,
[87] 1,4-dimethyl-3-p-tolyl-1H-pyrrole-2-carboxylic acid 3,5-difluorobenzylamide,
[88] 3-(4-methoxyphenyl)-1,4-dimethyl-1H-pyrrole-2-carboxylic acid indan-1-ylamide,
[89] 1-benzyl-4-methyl-3-phenyl-1H-pyrrole-2-carboxylic acid 4-dimethylaminobenzylamide,
[90] 1-(4-fluorobenzyl)-3-furan-2-yl-4-methyl-1H-pyrrole-2-carboxylic acid (1-naphthalen-2-ylmethylpyrrolidin-3-yl)-amide,
[91] [3-furan-2-yl-4-methyl-1-(4-trifluoromethylbenzyl)-1H-pyrrol-2-yl]-(4-methyl-[1,4]diazepan-1-yl)-methanone,
[94] 1,4-dimethyl-3-p-tolyl-1H-pyrrole-2-carboxylic acid (2-benzyloxy-cyclohexyl)-amide,
[96] (2,6-dimethylmorpholin-4-yl)-[3-(4-methoxyphenyl)-1,4-dimethyl-1H-pyrrol-2-yl]-methanone,
[97] 3-furan-2-yl-1-(4-methoxybenzyl)-4-methyl-1H-pyrrole-2-carboxylic acid (thiophen-2-ylmethyl)-amide,
[98] 1,4-dimethyl-3-p-tolyl-1H-pyrrole-2-carboxylic acid (furan-2-ylmethyl)-amide,
[99] 4-methyl-1-(4-methylbenzyl)-3-p-tolyl-1H-pyrrole-2-carboxylic acid (3-dimethylamino-propyl)-amide,
[100] 1-(4-fluorobenzyl)-3-(4-methoxyphenyl)-4-methyl-1H-pyrrole-2-carboxylic acid (2-oxo-tetrahydro-furan-3-yl)-amide,
[101] 3-(4-chlorophenyl)-1,4-dimethyl-1H-pyrrole-2-carboxylic acid (2-phenoxy-ethyl)-amide,
[103] 2-{[3-(4-methoxyphenyl)-1,4-dimethyl-1H-pyrrole-2-carbonyl]-amino}-3-phenylpropionic acid methyl ester,
[104] 3-(4-chlorophenyl)-1,4-dimethyl-1H-pyrrole-2-carboxylic acid (2-morpholin-4-ylethyl)-amide,
[105] 3-furan-2-yl-1,4-dimethyl-1H-pyrrole-2-carboxylic acid indan-2-ylamide,
[109] 3-(4-chlorophenyl)-1-isobutyl-4-methyl-1H-pyrrole-2-carboxylic acid p-tolylamide,
[111] 1-butyl-4-methyl-3-p-tolyl-1H-pyrrole-2-carboxylic acid [2-(2,5-dimethoxyphenyl)-ethyl]-amide,
[112] 1-butyl-4-methyl-3-p-tolyl-1H-pyrrole-2-carboxylic acid (3-imidazol-1-ylpropyl)-amide,
[113] 1-benzyl-3-(4-chlorophenyl)-4-methyl-1H-pyrrole-2-carboxylic acid [2-(3,4-dimethoxyphenyl)-ethyl]-methylamide,
[114] 4-methyl-1-(4-methylbenzyl)-3-p-tolyl-1H-pyrrole-2-carboxylic acid (3-morpholin-4-ylpropyl)-amide,
[115] 4-methyl-1-(4-methylbenzyl)-3-p-tolyl-1H-pyrrole-2-carboxylic acid 4-fluoro-2-trifluoromethylbenzylamide,
[116] 2-{[1-benzyl-3-(4-chlorophenyl)-4-methyl-1H-pyrrole-2-carbonyl]-amino}-3-(4-chlorophenyl)-propionic acid ethyl ester,
[117] 1-benzyl-4-methyl-3-phenyl-1H-pyrrole-2-carboxylic acid 3-fluoro-4-trifluoromethylbenzylamide,
[118] 1-(4-bromobenzyl)-4-methyl-3-p-tolyl-1H-pyrrole-2-carboxylic acid (2-pyridin-2-ylethyl)-amide,
[119] 1-(4-fluorobenzyl)-3-furan-2-yl-4-methyl-1H-pyrrole-2-carboxylic acid benzyl-(2-hydroxy-ethyl)-amide,
[122] 1-benzyl-4-methyl-3-phenyl-1H-pyrrole-2-carboxylic acid (1-benzylpyrrolidin-3-yl)-amide,
[124] 1-(4-methoxybenzyl)-4-methyl-3-p-tolyl-1H-pyrrole-2-carboxylic acid butylamide,
[125] 1-benzyl-4-methyl-3-p-tolyl-1H-pyrrole-2-carboxylic acid [2-(2-fluorophenyl)-ethyl]-amide,
[126] 4-methyl-1-(4-methylbenzyl)-3-p-tolyl-1H-pyrrole-2-carboxylic acid 3,4-dimethoxybenzylamide,
[127] 3-(4-chlorophenyl)-1-isobutyl-4-methyl-1H-pyrrole-2-carboxylic acid (2-diethylamino-ethyl)-amide,
[129] 1-(4-fluorobenzyl)-4-methyl-3-p-tolyl-1H-pyrrole-2-carboxylic acid 3-trifluoromethoxybenzylamide,
[130] [1-benzyl-3-(4-chlorophenyl)-4-methyl-1H-pyrrol-2-yl]-(3-methylpiperidin-1-yl)-methanone,
[131] 1-(4-fluorobenzyl)-4-methyl-3-p-tolyl-1H-pyrrole-2-carboxylic acid (2-p-tolylethyl)-amide,
[132] 1-(4-methoxybenzyl)-4-methyl-3-p-tolyl-1H-pyrrole-2-carboxylic acid [2-(2-methyl-5-nitro-imidazol-1-yl)-ethyl]-amide,
[133] 1,4-dimethyl-3-p-tolyl-1H-pyrrole-2-carboxylic acid 2,3-dimethoxybenzylamide,
[134] 1-(2-bromobenzyl)-3-(4-chlorophenyl)-4-methyl-1H-pyrrole-2-carboxylic acid [2-(ethyl-m-tolylamino)-ethyl]-amide,
[135] 1-(4-fluorobenzyl)-3-furan-2-yl-4-methyl-1H-pyrrole-2-carboxylic acid (4-isopropylphenyl)-amide,
[136] 5-chloro-2-methoxybenzoic acid N'-[1-(4-fluorobenzyl)-3-(4-methoxyphenyl)-4-methyl-1H-pyrrole-2-carbonyl]-hydrazide,
[137] (1-benzyl-4-methyl-3-p-tolyl-1H-pyrrol-2-yl)-[1,4]bipiperidinyl-1'-ylmethanone,
[138] 3-furan-2-yl-1,4-dimethyl-1H-pyrrole-2-carboxylic acid (4-butylphenyl)-amide,
[139] 1-benzyl-4-methyl-3-phenyl-1H-pyrrole-2-carboxylic acid [2-(1H-indol-3-yl)-ethyl]-amide,
[141] [1-(4-fluorobenzyl)-4-methyl-3-p-tolyl-1H-pyrrol-2-yl]-morpholin-4-ylmethanone,
[142] 3-[(1-benzyl-3-furan-2-yl-4-methyl-1H-pyrrole-2-carbonyl)-amino]-propionic acid ethyl ester,
[143] 1,4-dimethyl-3-phenyl-1H-pyrrole-2-carboxylic acid (naphthalen-2-ylcarbamoylmethyl)-amide,
[145] 1-(4-fluorobenzyl)-3-furan-2-yl-4-methyl-1H-pyrrole-2-carboxylic acid (4-cyanomethylphenyl)-amide,
[147] (1,4-dioxa-8-aza-spiro[4.5]dec-8-yl)-[1-(4-fluorobenzyl)-3-furan-2-yl-4-methyl-1H-pyrrol-2-yl]-methanone,
[148] 3-furan-2-yl-4-methyl-1-(4-trifluoromethylbenzyl)-1H-pyrrole-2-carboxylic acid pentylamide,
[149] 3-furan-2-yl-1-(4-methoxybenzyl)-4-methyl-1H-pyrrole-2-carboxylic acid [3-(methylphenylamino)-propyl]-amide,
[150] 1-(2,6-dichlorobenzyl)-4-methyl-3-p-tolyl-1H-pyrrole-2-carboxylic acid (2-azepan-1-ylethyl)-amide,
[151] 1-(4-bromobenzyl)-4-methyl-3-p-tolyl-1H-pyrrole-2-carboxylic acid cyclopentylamide,
[153] 3-(4-chlorophenyl)-1-(2-fluorobenzyl)-4-methyl-1H-pyrrole-2-carboxylic acid [2-(2-chlorophenoxy)-ethyl]-amide,
[154] 1-(2,6-dichlorobenzyl)-4-methyl-3-p-tolyl-1H-pyrrole-2-carboxylic acid (3,3-dimethylbutyl)-amide,
[155] 1,4-dimethyl-3-p-tolyl-1H-pyrrole-2-carboxylic acid (2-benzyloxy-cyclohexyl)-amide,
[156] [4-methyl-1-(4-methylbenzyl)-3-p-tolyl-1H-pyrrol-2-yl]-thiomorpholin-4-ylmethanone,
[157] 3-(4-chlorophenyl)-1-isobutyl-4-methyl-1H-pyrrole-2-carboxylic acid (3-dimethylamino-propyl)-methylamide,
[159] 5-chloro-2-methoxybenzoic acid N'-[3-(4-methoxyphenyl)-1,4-dimethyl-1H-pyrrole-2-carbonyl]-hydrazide,
[162] 3-furan-2-yl-4-methyl-1-(4-trifluoromethylbenzyl)-1H-pyrrole-2-carboxylic acid [1-(3-methoxyphenyl)-ethyl]amide,

[163] 2-[(1-benzyl-3-furan-2-yl-4-methyl-1H-pyrrole-2-carbonyl)-amino]-3-(4-chlorophenyl)-propionic acid methyl ester,
[165] 1,4-dimethyl-3-phenyl-1H-pyrrole-2-carboxylic acid (1-benzylpyrrolidin-3-yl)-amide,
[167] 4-methyl-1-(4-methylbenzyl)-3-p-tolyl-1H-pyrrole-2-carboxylic acid (3-methoxy-propyl)-amide,
[169] 1-(4-bromobenzyl)-4-methyl-3-p-tolyl-1H-pyrrole-2-carboxylic acid (3-morpholin-4-ylpropyl)-amide,
[170] 1,4-dimethyl-3-p-tolyl-1H-pyrrole-2-carboxylic acid [2-(2,3-dimethoxyphenyl)-ethyl]-amide,
[174] 1-(4-bromobenzyl)-4-methyl-3-p-tolyl-1H-pyrrole-2-carboxylic acid (1-ethylpyrrolidin-2-ylmethyl)-amide,
[175] 3-(4-chlorophenyl)-1-isobutyl-4-methyl-1H-pyrrole-2-carboxylic acid [2-(2-chlorophenoxy)-ethyl]-amide,
[176] 3-(4-chlorophenyl)-1,4-dimethyl-1H-pyrrole-2-carboxylic acid [2-(1H-indol-3-yl)-ethyl]-amide,
[177] 1-(4-fluorobenzyl)-4-methyl-3-p-tolyl-1H-pyrrole-2-carboxylic acid (naphthalen-2-ylcarbamoylmethyl)-amide,
[179] 1,4-dimethyl-3-phenyl-1H-pyrrole-2-carboxylic acid (1-benzylpyrrolidin-3-yl)-amide,
[184] (4-benzoylpiperidin-1-yl)-[1-(4-methoxybenzyl)-4-methyl-3-p-tolyl-1H-pyrrol-2-yl]-methanone,
[185] 3-furan-2-yl-1,4-dimethyl-1H-pyrrole-2-carboxylic acid ethylpyridin-4-ylmethylamide,
[186] 1-(4-bromobenzyl)-4-methyl-3-p-tolyl-1H-pyrrole-2-carboxylic acid (2-pyrrolidin-1-ylethyl)-amide,
[189] 1-(1,4-dimethyl-3-phenyl-1H-pyrrole-2-carbonyl)-hydroxypiperidine-3-carboxylic acid ethyl ester,
[190] 4-dimethyl-3-phenyl-1H-pyrrole-2-carboxylic acid (1-phenylethyl)-amide,
[191] [3-furan-2-yl-1-(4-methoxybenzyl)-4-methyl-1H-pyrrol-2-yl]-(1,3,4,9-tetrahydro-b-carbolin-2-yl)-methanone,
[194] 1-(2-bromobenzyl)-3-(4-chlorophenyl)-4-methyl-1H-pyrrole-2-carboxylic acid [2-(1H-indol-3-yl)-ethyl]-methylamide,
[196] 1,4-dimethyl-3-phenyl-1H-pyrrole-2-carboxylic acid 4-fluoro-2-trifluoromethylbenzylamide,
[197] 4-methyl-1-(4-methylbenzyl)-3-p-tolyl-1H-pyrrole-2-carboxylic acid (4-phenoxyphenyl)-amide,
[198] (4-hydroxy-piperidin-1-yl)-[1-(4-methoxybenzyl)-4-methyl-3-p-tolyl-1H-pyrrol-2-yl]-methanone,
[199] 4-diethylaminobenzoic acid N'-(1-benzyl-4-methyl-3-p-tolyl-1H-pyrrole-2-carbonyl)-hydrazide,
[201] 1-(4-bromobenzyl)-4-methyl-3-p-tolyl-1H-pyrrole-2-carboxylic acid [2-(3,4-dichlorophenyl)-ethyl]-amide,
[202] 3-(4-chlorophenyl)-1-ethyl-4-methyl-1H-pyrrole-2-carboxylic acid [2-(1H-indol-3-yl)-ethyl]-amide,
[204] 1,4-dimethyl-3-phenyl-1H-pyrrole-2-carboxylic acid 3-trifluoromethoxybenzylamide,
[207] 3-(4-chlorophenyl)-1-ethyl-4-methyl-1H-pyrrole-2-carboxylic acid 2,6-dimethoxybenzylamide,
[208] 4-methyl-1-(4-methylbenzyl)-3-p-tolyl-1H-pyrrole-2-carboxylic acid [2-(3,4-dimethoxyphenyl)-ethyl]-amide,
[210] [1-(4-fluorobenzyl)-4-methyl-3-p-tolyl-1H-pyrrol-2-yl]-[4-(2-methoxyphenyl)-piperidin-1-yl]-methanone,
[211] [3-furan-2-yl-4-methyl-1-(4-trifluoromethylbenzyl)-1H-pyrrol-2-yl]-thiomorpholin-4-ylmethanone,
[212] 1,4-dimethyl-3-phenyl-1H-pyrrole-2-carboxylic acid (2-thiophen-2-ylethyl)-amide,
[213] 4-diethylaminobenzoic acid N'-(1-butyl-4-methyl-3-p-tolyl-1H-pyrrole-2-carbonyl)-hydrazide,
[214] {1-[1-(4-fluorobenzyl)-3-(4-methoxyphenyl)-4-methyl-1H-pyrrole-2-carbonyl]-pyrrolidin-3-yl}-carbamic acid tert.-butyl ester,
[217] 3-furan-2-yl-1,4-dimethyl-1H-pyrrole-2-carboxylic acid 3,4-dimethoxybenzylamide,
[220] 3-furan-2-yl-4-methyl-1-(4-trifluoromethylbenzyl)-1H-pyrrole-2-carboxylic acid (4-tert.-butylphenyl)-amide,
[223] 1,4-dimethyl-3-phenyl-1H-pyrrole-2-carboxylic acid 3,5-difluorobenzylamide,
[224] 1,4-dimethyl-3-phenyl-1H-pyrrole-2-carboxylic acid (pyridin-4-ylmethyl)-amide,
[226] 3-furan-2-yl-1,4-dimethyl-1H-pyrrole-2-carboxylic acid methyl-(2-pyridin-2-ylethyl)-amide,
[227] 3-furan-2-yl-1,4-dimethyl-1H-pyrrole-2-carboxylic acid (3-methoxybenzyl)-(tetrahydro-furan-2-ylmethyl)-amide,
[228] 3-furan-2-yl-1,4-dimethyl-1H-pyrrole-2-carboxylic acid (4-phenoxyphenyl)-amide,
[229] 3-furan-2-yl-1,4-dimethyl-1H-pyrrole-2-carboxylic acid pentylamide,
[231] 3-furan-2-yl-1,4-dimethyl-1H-pyrrole-2-carboxylic acid phenylamide,
[233] 3-furan-2-yl-1,4-dimethyl-1H-pyrrole-2-carboxylic acid [2-(3,4-dichlorophenyl)-ethyl]-amide,
[234] 3-furan-2-yl-1,4-dimethyl-1H-pyrrole-2-carboxylic acid [2-(2-chlorophenoxy)-ethyl]-amide,
[235] 3-furan-2-yl-1,4-dimethyl-1H-pyrrole-2-carboxylic acid 3-methoxybenzylamide,
[236] 3-furan-2-yl-4-methyl-1-(4-trifluoromethylbenzyl)-1H-pyrrole-2-carboxylic acid phenethylamide,
[237] 3-furan-2-yl-1,4-dimethyl-1H-pyrrole-2-carboxylic acid cyclopentylamide,
[238] 3-furan-2-yl-1,4-dimethyl-1H-pyrrole-2-carboxylic acid (pyridin-2-ylmethyl)-amide,
[239] 3-furan-2-yl-4-methyl-1-(4-trifluoromethylbenzyl)-1H-pyrrole-2-carboxylic acid [2-(3,4-dimethoxyphenyl)-ethyl]-amide,
[240] [1-(4-bromobenzyl)-4-methyl-3-p-tolyl-1H-pyrrol-2-yl]-(2,6-dimethylmorpholin-4-yl)-methanone,
[241] 1,4-dimethyl-3-phenyl-1H-pyrrole-2-carboxylic acid (2-p-tolylethyl)-amide,
[243] 4-methyl-1-(4-methylbenzyl)-3-p-tolyl-1H-pyrrole-2-carboxylic acid [2-(1H-indol-3-yl)-ethyl]-methylamide,
or a pharmaceutically acceptable salt thereof.

15. A method for preparing a 1,3-disubstituted 4-methyl-1H-pyrrole-2-carboxamide compound as claimed in claim 1, comprising: reacting a compound corresponding to formula II,

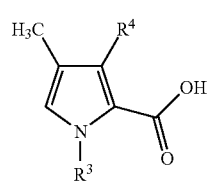

wherein $R^3$ and $R^4$ have the meanings given in claim 1,
optionally in a reaction medium, and optionally in the presence of a coupling agent, and optionally in the presence of a base, and at a temperature of −70° C. to 100° C., with a compound corresponding to the formula HNR¹R²,
wherein R¹ and R² have the meanings given in claim 1, to obtain a compound corresponding to formula I

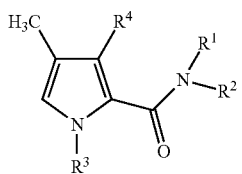

wherein R¹, R², R³ and R⁴ have the above-stated meanings, and optionally isolating or purifying the compound of formula I, and optionally converting the compound of formula I into a pharmaceutically acceptable salt.

16. A pharmaceutical composition comprising a compound as claimed in claim 1 and at least one pharmaceutically acceptable carrier or pharmaceutical auxiliary substance.

17. A method of inhibiting noradrenaline reuptake or 5-hydroxy-tryptophan reuptake or both in a subject in need thereof, said method comprising administering to said subject an effective receptor inhibiting amount of a compound as claimed in claim 1.

18. A method of treating pain in a subject in need thereof, said method comprising administering to said subject an analgesically effective amount of a compound as claimed in claim 1.

19. A method as claimed in claim 18, wherein said pain is selected from the group consisting of acute pain, chronic pain and neuropathic pain.

* * * * *